(12) United States Patent
Bower et al.

(10) Patent No.: US 8,138,321 B2
(45) Date of Patent: Mar. 20, 2012

(54) **ACETOLACTATE SYNTHASE (ALS) SELECTABLE MARKER FROM *TRICHODERMA REESEI***

(75) Inventors: Benjamin S. Bower, Palo Alto, CA (US); Nigel Dunn-Coleman, El Sauzal (ES); Nicholas Leiva, San Francisco, CA (US)

(73) Assignee: Danisco US Inc., Palo Alto, CA (US)

( * ) Notice: Subject to any disclaimer, the term of this patent is extended or adjusted under 35 U.S.C. 154(b) by 71 days.

(21) Appl. No.: 12/441,574

(22) PCT Filed: Sep. 21, 2007

(86) PCT No.: PCT/US2007/020484
§ 371 (c)(1),
(2), (4) Date: May 28, 2010

(87) PCT Pub. No.: WO2008/039370
PCT Pub. Date: Apr. 3, 2008

(65) Prior Publication Data
US 2010/0273201 A1   Oct. 28, 2010

Related U.S. Application Data

(60) Provisional application No. 60/846,656, filed on Sep. 22, 2006, provisional application No. 60/846,804, filed on Sep. 22, 2006.

(51) Int. Cl.
*C07H 21/04* (2006.01)
*C12N 9/10* (2006.01)
*C12N 5/10* (2006.01)
*C12N 1/15* (2006.01)
*C12Q 1/68* (2006.01)
*C12Q 1/48* (2006.01)
*C12Q 1/02* (2006.01)

(52) U.S. Cl. .. 536/23.2; 435/193; 435/419; 435/254.11; 435/254.6; 435/6.18; 435/6.15; 435/15; 435/29

(58) Field of Classification Search ................ 536/23.2; 435/193, 419, 254.6, 6.18, 6.15, 15, 29, 254.11
See application file for complete search history.

(56) References Cited

U.S. PATENT DOCUMENTS

| | | |
|---|---|---|
| 4,127,405 A | 11/1978 | Levitt |
| 4,581,059 A | 4/1986 | Adams, Jr. et al. |
| 4,678,500 A | 7/1987 | Hay et al. |

(Continued)

FOREIGN PATENT DOCUMENTS

DE   40 00 503 A1   7/1991

(Continued)

OTHER PUBLICATIONS

Alignment of instant Seq Id No:2 with Seq Id Nos:3 and 6 of Hammer et al. (US 7,538,262 B2), search of database of issued U.S. patents, Nov. 14, 2011.*

(Continued)

*Primary Examiner* — Rosanne Kosson
(74) *Attorney, Agent, or Firm* — Danisco US Inc.

(57) ABSTRACT

A nucleic acid encoding an acetolactate synthase (ALS) protein that provides resistance to ALS inhibitors, e.g., sulphonylurea and imidazolinone compounds, is provided. The nucleic acid may be used as a selectable marker for expression of a protein of interest in host cells.

24 Claims, 15 Drawing Sheets

U.S. PATENT DOCUMENTS

| | | | |
|---|---|---|---|
| 4,797,361 | A | 1/1989 | Montenecourt |
| 5,364,770 | A | 11/1994 | Berka et al. |
| 5,874,276 | A | 2/1999 | Fowler et al. |
| 6,022,725 | A | 2/2000 | Fowler et al. |
| 6,103,490 | A | 8/2000 | Berka et al. |
| 6,268,328 | B1 | 7/2001 | Mitchinson et al. |
| 6,509,171 | B1 | 1/2003 | Berka et al. |
| 7,262,041 | B2 | 8/2007 | Baldwin et al. |
| 7,354,752 | B2 | 4/2008 | Dunn-Coleman et al. |
| 7,538,262 | B2 * | 5/2009 | Hammer et al. ............ 800/300 |
| 2005/0204436 | A1 | 9/2005 | Hammer et al. |
| 2006/0040353 | A1 | 2/2006 | Davidson et al. |
| 2006/0041113 | A1 | 2/2006 | Stafford et al. |

FOREIGN PATENT DOCUMENTS

| | | |
|---|---|---|
| EP | 0 004 163 A1 | 9/1979 |
| EP | 0 079 683 A2 | 5/1983 |
| EP | 0 113 956 A1 | 7/1984 |
| EP | 0 131 258 A2 | 1/1985 |
| EP | 0 282 613 A1 | 9/1988 |
| EP | 0 342 569 A1 | 11/1989 |
| WO | WO 91/10660 A1 | 7/1991 |
| WO | WO 96/00787 A1 | 1/1996 |
| WO | WO 2005/001036 A2 | 1/2005 |

OTHER PUBLICATIONS

Altschul, S.F. et al. "Basic local alignment search tool." *J. Mol. Biol.* 215(3):403-410, 1990.

Berka, R.M. et al. "Molecular cloning and deletion of the gene encoding aspergillopepsin A from *Aspergillus awamori*." *Gene* 86(2):153-162, 1990.

Campbell, E.I. et al. "Improved transformation efficiency of *Aspergillus niger* using the homologous niaD gene for nitrate reductase." *Current Genetics* 16(1):53-56, 1989.

Chipman, D. et al. "Biosynthesis of 2-aceto-2-hydroxy acids: acetolactate synthases and acetohydroxyacid synthases." *Biochimica et Biophysica Acta (BBA)—Protein Structure and Molecular Enzymology* 1385(2):401-419, 1998.

Chipman, D.M. et al. "Mechanisms of acetohydroxyacid synthases." *Current Opinion in Chemical Biology* 9(5):475-481, 2005.

Davis, R.H. et al. "Genetic and microbiological research techniques for *Neurospora crassa*." *Methods Enzymol.* 17A:79-143, 1970.

Doig, R.I. et al. "DPX T6376—A new broad spectrum cereal herbicide." In *Proc. 10th Int. Congr. Plant Prot.*, vol. 1. Brighton, UK, pp. 324-333, 1983.

Duggleby, R.G. et al. "Systematic characterization of mutations in yeast acetohydroxyacid synthase." *European Journal of Biochemistry* 270(13):2895-2904, 2003.

Foreman, P.K. et al. "Transcriptional Regulation of Biomass-degrading Enzymes in the Filamentous Fungus *Trichoderma reesei*." *J Biol. Chem.* 278(34):31988-31997, 2003.

Hacker, E. et al. "Hoe 75032, ein neues, selektives Nachauflauf-Herbizid zur Bekämpfung von Galium spp. und anderen Unkräutern vornehmlich in Getreide." *Zeitschrift für Pflanzenkrankheiten und Pflanzenschutz Sonderheft* 12:489-97, 1990.

Hartley, J.L. et al. "DNA cloning using in vitro site-specific recombination." *Genome Research* 10(11):1788-1795, 2000.

Hill, C.M. et al. "Mutagenesis of *Escherichia coli* acetohydroxyacid synthase isoenzyme II and characterization of three herbicide-insensitive forms." *Biochemical Journal* 335 (Pt 3):653-661, 1998.

Ibdah, M. et al. "Homology Modeling of the Structure of Bacterial Acetohydroxy Acid Synthase and Examination of the Active Site by Site-Directed Mutagenesis." *Biochemistry* 35(50):16282-16291, 1996.

Ilmen, M. et al. "Regulation of cellulase gene expression in the filamentous fungus *Trichoderma reesei*." *Appl. Environ. Microbiol.* 63(4):1298-1306, 1997.

Innis, M. A. et al. "Expression, Glycosylation, and Secretion of an *Aspergillus* Glucoamylase by *Saccharomyces cerevisiae*." *Science* 228(4695):21-26, 1985.

Jung, S.-M. et al. "Amino acid residues conferring herbicide resistance in tobacco acetohydroxy acid synthase." *Biochemical Journal* 383(Pt 1):53-61, 2004.

Karlin, S. et al. "Applications and statistics for multiple high-scoring segments in molecular sequences." *Proc. Natl. Acad. Sci. USA* 90(12):5873-7, 1993.

Kimura, F. et al. "SL-950, a novel sulfonylurea herbicide for corn." In *Proceedings of the Brighton Crop Protection Conference, Weeds*, Brighton, UK, pp. 29-34, 1989.

Machida, M. et al. "Genome sequencing and analysis of *Aspergillus oryzae*." *Nature* 438(7071):1157-61, 2005.

Maurer, W. et al. "CGA 136'872: A new post emergence herbicide for the selective control of Sorghum spp. and Elymus repens in maize." In *Proceedings of the Brighton Crop Protection Conference, Weeds*, Brighton, UK, pp. 41-48, 1987.

Mendel, S. et al. "Acetohydroxyacid synthase: A proposed structure for regulatory subunits supported by evidence from mutagenesis." *Journal of Molecular Biology* 307(1):465-477, 2001.

Needleman, S.B. et al. "A general method applicable to the search for similarities in the amino acid sequence of two proteins." *J. Mol. Biol.* 48(3):443-53, 1970.

Nevalainen, K.M.H. et al. "The Molecular Biology of Trichoderma and its Application to the Expression of Both Homologous and Heterologous Genes." In *Molecular Industrial Mycology*, eds. S.A. Leong et al. New York: Marcel Dekker, pp. 129-148, 1991.

Palm, H.L. et al. "New lowrate sulfonylureas for post-emergence weed control in corn." In *Proceedings of the Brighton Crop Protection Conference, Weeds*, vol. 1. Brighton, UK, pp. 23-28, 1989.

Paloheimo, M. et al. "High-Yield Production of a Bacterial Xylanase in the Filamentous Fungus *Trichoderma reesei* Requires a Carrier Polypeptide with an Intact Domain Structure." *Appl. Environ. Microbiol.* 69(12):7073-7082, 2003.

Pang, S.S. et al. "Crystal structure of yeast acetohydroxyacid synthase: a target for herbicidal inhibitors." *Journal of Molecular Biology* 317(2):249-262, 2002.

Pang, S.S. et al. "Molecular Basis of Sulfonylurea Herbicide Inhibition of Acetohydroxyacid Synthase." *Journal of Biological Chemistry* 278(9):7639-7644, 2003.

Pang, S.S. et al. "The Crystal Structures of Klebsiella pneumoniae Acetolactate Synthase with Enzyme-bound Cofactor and with an Unusual Intermediate." *Journal of Biological Chemistry* 279(3):2242-2253, 2004.

Pearson, W.R. et al. "Improved Tools for Biological Sequence Comparison." *Proc. Natl. Acad. Sci. USA* 85(8):2444-2448, 1988.

Pourquié, J. et al. "Scale up of cellulase production and utilization." In *Biochemistry and Genetics of Cellulose Degradation*, eds. J.P. Aubert et al. London: Academic Press, pp. 71-86, 1988.

Saarelainen, R. et al. "Expression of Barley Endopeptidase B in *Trichoderma reesei*." *Appl. Environ. Microbiol.* 63(12):4938-4940, 1997.

Sheir-Neiss, G. et al. "Characterization of the secreted cellulases of *Trichoderma reesei* wild type and mutants during controlled fermentations." *Applied Microbiology and Biotechnology* 20(1):46-53, 1984.

Smith, T.F. et al. "Comparison of biosequences." *Adv. Appl. Math* 2:482-489, 1981.

Thomson, W.T. In *Agricultural Chemicals: Book II, Herbicides*, Fresno, CA: Thomson Publications, pp. 152 and 155, 1990.

Wixson, M.B. et al. "Differential Response of Soybean (Glycine max) Cultivars to AC 263,222." *Weed Technology* 5(2):430-433, 1991.

Wixson, M.B. et al. "Use of AC 263,222 for Sicklepod (*Cassia obtusifolia*) Control in Soybean (Glycine max)." *Weed Technology* 5(2):434-438, 1991.

Worthing, C.R. et al., eds. In *The pesticide manual : a world compendium*, 9th ed. Farnham, England: British Crop Protection Council, pp. 735, 774, 837, and 840, 1991.

Worthing, C.R. et al., eds. In *The pesticide manual : a world compendium*, 8th ed. Farnham, England: British Crop Protection Council, pp. 473-474, 1987.

Yadav, N. et al. "Single amino acid substitutions in the enzyme acetolactate synthase confer resistance to the herbicide sulfometuron methyl." *Proceedings of the National Academy of Sciences of the United States of America* 83(12):4418-4422, 1986.

* cited by examiner

MLRSRQVTARAVRALGQARAFTSTTKPVMIQSSQRKQANASAAPQVRPVP
SPAFNAEDKDRSHVQPLVNPSKPDMDESFIGKTGGEIFHEMMLRQGVKHI
FGYPGGAILPVFDAIYNSKHFDFILPRHEQGAGHMAEGYARASGKPGVVL
VTSGPGATNVITPMQDALSDGTPLVVFCGQVPTTAIGSD<u>A</u>FQEADVVGIS
RACTKWNVMVKSVAELPRRINEAFEIATSGRPGPVLVDLP<u>K</u>DVTAGILRR
AIPTETALPSLPSAASRAAMELSSKQLNASIKRAADLINIAKKPVIYAGQ
GVIQSEGGVELLKQLADKASIPVTTTLHGLGAFDELDEKSLHMLGMHGSA
YANMAMQQADLIIALGSRFDD<u>R</u>VTLNVSKFAPAARQAAAEGRGGIIHFEI
MPKNINKVIQATEAVEGDVAT<u>N</u>LKHLIPQIAEKSMADRGEWFGLINEWKK
KWPLSNYQRAERAGLIKPQTVMEEISNLTANRKDKTYIATGVGQHQMWVA
QHFRWRHPRSMITSGGLGTMGYGLPAAIGAKVAQPDALVIDVDGDASFNM
TLTELSTAAQFNIGVKVVVLNNEEQGMVTQWQNLFYEDRYAHTHQKNPDF
MKLADAMGVQHQRVTEPEKLVDALTWLINTDGPALLEVVTDKKVPVLPMV
PAGSALHEFLVFEPEKDKQRRELMKERTKGVHS

Fig. 1

ATGCTCCGAAGTCGCCAAGTCACAGCCAGGGCCGTCCGGGCTCTGGGCCAGGCGCG
CGCCTTTACCTCGACGACCAAGCCTGTCATGATCCAGAGCAGCCAGAGGAAACAGG
CCAACGCCAGCGCTGCTCCACAAGTCCGCCCTGTACCGAGCCCTGCTTTCAACGCT
GAAGACAAAGACCGCAGCCATGTGCAGCCTCTGGTCAACCCGTCGAAGCCCGACAT
GGATGAATCATTCATTGGCAAAACCGGAGGCGAAATCTTCCACGAGATGATGCTGC
GACAGGGTGTCAAGCACATTTTCGGATACCCTGGCGGCGCTATCCTGCCCGTCTTC
GACGCCATCTACAACTCAAAACACTTCGACTTCATCCTGCCCCGTCATGAGCAGGG
AGCTGGCCATATGGCCGAGGGCTATGCCCGTGCCTCGGGCAAACCCGGTGTCGTCC
TGGTGACTTCCGGCCCCGGTGCTACCAATGTCATCACGCCCATGCAGGATGCCCTG
TCGGACGGAACGCCCTTGGTCGTCTTCTGCGGCCAGGTCCCCACCACGGCCATCGG
CAGCGATGCCTTCCAAGAGGCCGACGTCGTGGGCATCTCGCGGGCCTGCACCAAGT
GGAACGTCATGGTCAAGAGCGTTGCTGAGCTGCCGCGGAGAATCAACGAGGCCTTT
GAGATTGCCACCAGCGGCCGCCCTGGCCCCGTCCTCGTCGACCTGCCCAAGGATGT
CACGGCTGGTATCCTGAGGAGAGCCATCCCTACGGAGACTGCTCTGCCGTCTCTGC
CCAGTGCCGCCTCCCGCGCCGCCATGGAGCTGAGCTCCAAGCAGCTCAACGCCTCC
ATCAAGCGTGCCGCCGACCTCATCAACATCGCCAAGAAGCCCGTCATCTACGCCGG
TCAGGGTGTCATCCAGTCCGAGGGCGGCGTTGAGCTCCTGAAGCAGCTGGCGGACA
AGGCCTCCATCCCCGTCACCACCACCCTCCATGGCCTGGGTGCCTTTGATGAGCTG
GACGAGAAGTCGCTGCACATGCTGGGCATGCACGGCTCGGCGTATGCCAACATGGC
CATGCAGCAGGCCGACCTCATCATCGCCCTCGGCAGCCGATTCGACGACCGTGTTA
CTCTGAATGTCTCCAAATTTGCGCCTGCAGCCAGGCAAGCTGCTGCCGAGGGCCGC
GGCGGCATCATTCACTTTGAGATCATGCCCAAGAACATCAACAAGGTCATCCAGGC
GACCGAGGCCGTCGAGGGCGACGTCGCCACCAACCTGAAGCACCTCATTCCCCAGA
TTGCCGAAAAGTCCATGGCGGACCGAGGAGAGTGGTTCGGCCTCATCAATGAGTGG
AAGAAGAAGTGGCCCCTGTCAAACTACCAGCGCGCGGAGCGGGCTGGCCTCATCAA
GCCGCAGACGGTCATGGAGGAGATTAGCAACCTGACGGCCAACCGAAAGGACAAGA
CGTACATTGCCACGGGTGTCGGCCAGCACCAGATGTGGGTTGCCCAGCACTTCCGC
TGGAGGCACCCTCGATCCATGATTACCTCTGGTGGTCTGGGCACCATGGGCTACGG
TCTCCCCGCGGCCATTGGCGCCAAGGTGGCCCAGCCCGACGCTCTCGTAATTGACG
TTGATGGCGATGCCTCGTTTAACATGACGCTGACGGAGCTGTCGACTGCTGCACAG
TTCAACATTGGCGTCAAGGTGGTTGTGCTCAACAACGAGGAGCAGGGCATGGTGAC
GCAGTGGCAGAACCTCTTTTACGAGGACCGATATGCCCACACGCACCAGAAGAACC
CCGACTTCATGAAGCTGGCCGACGCCATGGGCGTTCAGCACCAGCGCGTGACGGAG
CCGGAGAAGCTGGTCGATGCCCTGACGTGGCTGATCAACACCGATGGCCCGGCCCT
GTTGGAGGTTGTCACGGACAAGAAGGTGCCTGTCCTGCCCATGGTGCCCGCCGGAT
CGGCCCTGCACGAGTTCCTCGTCTTTGAACCTGAAAAGGATAAGCAGCGCCGTGAG
CTGATGAAGGAGAGAACAAAGGGTGTGCACTCCTAA

Fig. 2

```
TGAGACAATGGCCGGCAATGGTAAAAAGGACCAAGATGTACTAGGTAGTTGCAATGTGGCTTAT
TACCTACCTACTACCTGGTAGGCACCTACTAGGTACTTGGGTAGACGGACAATGAAATTTGAAG
TCGGGGTTGCAGGAAAGCAGGGCGCTGGACACATTGTGCTTCAGGCGGTACCCGTCGTCATCGT
CAGCCAATGTCGAGGCCCGGCAGCCCGAGGAGCGAGACAACCTTGGCCGGAGGAGCCCGCAGGT
ACCTGCCAAAGCGCGGCTGGTACCTCTCAACCCTCTCAGGCCTGTTGGATGCCCTATGACATGC
CCTGGGGGATGCAGCTGTTGCCCCGGCCCCGCACTTTCGGGTGACCGCGAGGCTGCTGATTGGC
TGGTTGCCACGGGCTGGGCGGTCCCTGAAGTTGTTGCCATCTGAACTCTGTCGGCGCTGGCGTC
GGCTGCGCCCAATGGGAGGCGAGACAACTCAGGGTACTAGAATCACTGACAGAAGAAGAGAATC
GAAAGTAGGTAGACAGCCAATTCGTTGCATGGCAGGCAACCGCACAGGAGAAAAATTGACTACC
CCACAATCAGGCACAGTAAGTAGGGCACAGTACGTATGTACAGACAAGGCGCAAGCGATACTGC
GCGACCCGGTACCTCGCCGGCTTGACACGTGCGACAGGCTACTTTACTAGTATTCGCAGCGGCG
GGTCGCGCATTATTACATGTACTGTGCCGCCATTTGATGACTGGGCTGCTGCAGTATTAGTAGA
TCTGCCCGGCATCGCCCTTCCATGGGCGCGACCCGGGACTGGACCCTCTGACTCTACCTACATG
TACCTAGGCCGGGCCGGGCTTGGTGACTTTTGTCCGATCAGGTCGTTCGCCTGGCTACCTATTA
TTTCTCTTTCTTCTTCTCCATCCTGCTTCTGGCCTTGCAATTCTTCTTCGCCACTCCTCCCTCT
TCCCCCCGCGATACCCTTGAATTCGTCAGAGAGGAAAAGACGAGAAAAAAAGGGCAGCAGAGA
CGTCGGTCTGGCTCACGTGCTGCATCTCTGCGCACTCTCATTTTTTTATTGTCCGACCCCTCC
CTCAACCTTCTCCTTCGTTGACAGGCTAAGCCTTGCTTCGACGCTCTCTCTTTGAATTTTTCTA
CTTCTACCTTCTTTTCTTGCGTGTTACCCACCATAGCTCGATTCACGATGCTCCGAAGTCGCCA
AGTCACAGCCAGGGCCGTCCGGGCTCTGGGCCAGGCGCGCGCCTTTACCTCGACGACCAAGCCT
GTCATGATCCAGAGCAGCCAGAGGAAACAGGCCAACGCCAGCGCTGCTCCGTAAGTCGCCCATT
GCCATTGCATCTTCTGTTTGATATATACTTCCTGCTGCTTGCGTGGCGTCGTCTCTCGGTTATG
CGTGTCAAGGACCAGGTGTGTTCGCATCGTGGTTTTCCAGCGCCGATTACCGGGGGACGAATTT
TTGGCTGCTCAACTCGCGCGCGCATTCTGATTCTTCGTTTTCAATCTTGAGCGACAACTGGC
TAACATAATGGCCATTGGCAATTGCTTCACACAGACAAGTCCGCCCTGTACCGAGCCCTGCTTT
CAACGCTGAAGACAAAGACCGCAGCCATGTGCAGCCTCTGGTCAACCCGTCGAAGCCCGACATG
GATGAATCGTATGTCCACGTCCCCTCGTCCCGCCCTACAAAATGAACACGATTACACCAGAATT
TTTGCAACAATCGACACTTCTATAACAGACCAATTGAGCTTTGTTCTGACCAATCATGTTGCTC
TAGATTCATTGGCAAAACCGGAGGCGAAATCTTCCACGAGATGATGCTGCGACAGGGTGTCAAG
CACATTTGTAGGTTCCGATGCCGGCCGCCCACACGGGCTCCATCCTTGCTCCATCTCTCCAGCT
AGGCAAATCTCGCTAACCTTGAGTCACCATCCAGTCGGATACCCTGGCGGCGCTATCCTGCCCG
TCTTCGACGCCATCTACAACTCAAAACACTTCGACTTCATCCTGCCCCGTCATGAGCAGGGAGC
TGGCCATATGGCCGAGGGCTATGCCCGTGCCTCGGGCAAACCCGGTGTCGTCCTGGTGACTTCC
GGCCCCGGTGCTACCAATGTCATCACGCCCATGCAGGATGCCCTGTCGGACGGAACGCCCTTGG
TCGTCTTCTGCGGCCAGGTCCCCACCACGGCCATCGGCAGCGATGCCTTCCAAGAGGCCGACGT
CGTGGGCATCTCGCGGGCCTGCACCAAGTGGAACGTCATGGTCAAGAGCGTTGCTGAGCTGCCG
CGGAGAATCAACGAGGCCTTTGAGATTGCCACCAGCGGCCGCCCTGGCCCCGTCCTCGTCGACC
TGCCCAAGGATGTCACGGCTGGTATCCTGAGGAGAGCCATCCCTACGGAGACTGCTCTGCCGTC
TCTGCCCAGTGCCGCCTCCCGCGCCGCCATGGAGCTGAGCTCCAAGCAGCTCAACGCCTCCATC
AAGCGTGCCGCCGACCTCATCAACATCGCCAAGAAGCCCGTCATCTACGCCGGTCAGGGTGTCA
TCCAGTCCGAGGGCGGCGTTGAGCTCCTGAAGCAGCTGGCGGACAAGGCCTCCATCCCCGTCAC
CACCACCCTCCATGGCCTGGGTGCCTTTGATGAGCTGGACGAGAAGTCGCTGCACATGCTGGGC
ATGCACGGCTCGGCGTATGCCAACATGGCCATGCAGCAGGCCGACCTCATCATCGCCCTCGGCA
```

Fig. 3 page 1 of 2

```
GCCGATTCGACGACCGTGTTACTCTGAATGTCTCCAAATTTGCGCCTGCAGCCAGGCAAGCTGC
TGCCGAGGGCCGCGGCGGCATCATTCACTTTGAGATCATGCCCAAGAACATCAACAAGGTCATC
CAGGCGACCGAGGCCGTCGAGGGCGACGTCGCCACCAACCTGAAGCACCTCATTCCCCAGATTG
CCGAAAAGTCCATGGCGGACCGAGGAGAGTGGTTCGGCCTCATCAATGAGTGGAAGAAGAAGTG
GCCCCTGTCAAACTACCAGCGCGCGGAGCGGGCTGGCCTCATCAAGCCGCAGACGGTCATGGAG
GAGATTAGCAACCTGACGGCCAACCGAAAGGACAAGACGTACATTGCCACGGGTGTCGGCCAGC
ACCAGATGTGGGTTGCCCAGCACTTCCGCTGGAGGCACCCTCGATCCATGATTACCTCTGGTGG
TCTGGGCACCATGGGCTACGGTCTCCCCGCGGCCATTGGCGCCAAGGTGGCCCAGCCCGACGCT
CTCGTAATTGACGTTGATGGCGATGCCTCGTTTAACATGACGCTGACGGAGCTGTCGACTGCTG
CACAGTTCAACATTGGCGTCAAGGTGGTTGTGCTCAACAACGAGGAGCAGGGCATGGTGACGCA
GTGGCAGAACCTCTTTTACGAGGACCGATATGCCCACACGCACCAGAAGAACCCCGACTTCATG
AAGCTGGCCGACGCCATGGGCGTTCAGCACCAGCGCGTGACGGAGCCGGAGAAGCTGGTCGATG
CCCTGACGTGGCTGATCAACACCGATGGCCCGGCCCTGTTGGAGGTTGTCACGGACAAGAAGGT
GCCTGTCCTGCCCATGGTGCCCGCCGGATCGGCCCTGCACGAGTTCCTCGTCTTTGAACCTGGT
GAGTCTACTTCAGACATATTGCTTGCGCATTGCAGATACTAACACTCTCACAGAAAAGGATAAG
CAGCGCCGTGAGCTGATGAAGGAGAGAACAAAGGGTGTGCACTCCTAAAGCGATGATGTCTGCG
AGGGGTTCTTCGTTGAACCCTAGTTCAGGCACCATCTTACCCTCTTATTTTTTCCCGTGGGCTT
TCATTTTGTGTCATCCGAGCATGACGTTGTAGGGTTGGAGTTTCTTCCTTTTTATCTTGTCATT
TACTGGTACCCATAGGCGCGAGACTAGGCTTCCATGTTTTGTTTTGCGACTTTCAAAAAGTACT
TTTAGTGGTTTGGGGCACGACGAGGGGGGGCAACCTCTTCTGTCGAAAAAGGTGGCTGGATGGA
TGAGATGAGATGAGATGAGGGTGAAGATAGATACCTGCAGTGTTTTGACGCGACGGGATG
```

Fig. 3 page 2 of 2

Fig. 5A contig1818 A version promoter (868 base pairs):
TAGGCTGGCGGGTTGGTGCTTTTGCCCTTTGTCTGCCGCGACCTCTTGGTGACGCTGCATCGTGTTGGCTGTAGCTGCAC
GCCCGGCCTCTTTTCTGGCATCTCGCACAGACTGTACGCAGAACATGTGTAAGTGACTTTCTATTGTAGGACTTGGATGG
ATGGGAGATGGCTATAGACAACAAGAGCGACAACAAGGATTATAGACAGTTCCATTACCTGGGCGACCACCATCGCACTT
CACCTTGCTCGCCCGGCAGGACTGGCAGGCGTTGGCAATCTTGAGTCGCTCCCTGTACAGCGACAAGGGCGCCTGAGCCT
GCACCTGAGCCTGGGCCTGAGTCTGAGCCTGAAGCCGTTGATCCTCGTCTTGACGGGCGGACATGACGCTTTACGTGAGC
TGAGTCCAGGGCTGTCGTCGGCAAGTGATTCGGCAGCCGGCAGGCACAGACGAAAGATAAGAAGCGGCTCGTTCACCAGA
TCCGAAGGCGGAATGCAAGAATGTCCGATGATGTCGGGGAAGAGAAGGCGATGCCTCGTCTATCTGGGAGGCGAGGGAAG
AAGGGAAAGCAACTCCCGCCTCGGCACAGCTACTCATTGGTCAGAGCGGACTTCGGAGTATAACCACACGGCTGACAAAC
CTGCATCGACCGTGATGGCGTTCTTTTGGTCCAATCATGGCTGAATGCGACGTTGGTTGTGTCGGCCCTGCAGCCAATG
AGAAGCTGGTCCGATCCTGGGGACGAGGGAGAGGCAAGCATATCGTATAAGTCCAAGCTCAAGCTTGGCGGCAGGTACCG
GTTGATGTGGTCGCTGTATATAAGTAAAAGAACTCGATTCCGCTTCGGAGTTTTCTCTGTCACCCTTC

Fig. 5B contig1818 B version promoter (928 base pairs):
TAGGCTGGCGGGTTGGTGCTTTTGCCCTTTGTCTGCCGCGACCTCTTGGTGACGCTGCATCGTGTTGGCTGTAGCTGCAC
GCCCGGCCTCTTTTCTGGCATCTCGCACAGACTGTACGCAGAACATGTGTAAGTGACTTTCTATTGTAGGACTTGGATGG
ATGGGAGATGGCTATAGACAACAAGAGCGACAACAAGGATTATAGACAGTTCCATTACCTGGGCGACCACCATCGCACTT
CACCTTGCTCGCCCGGCAGGACTGGCAGGCGTTGGCAATCTTGAGTCGCTCCCTGTACAGCGACAAGGGCGCCTGAGCCT
GCACCTGAGCCTGGGCCTGAGTCTGAGCCTGAAGCCGTTGATCCTCGTCTTGACGGGCGGACATGACGCTTTACGTGAGC
TGAGTCCAGGGCTGTCGTCGGCAAGTGATTCGGCAGCCGGCAGGCACAGACGAAAGATAAGAAGCGGCTCGTTCACCAGA
TCCGAAGGCGGAATGCAAGAATGTCCGATGATGTCGGGGAAGAGAAGGCGATGCCTCGTCTATCTGGGAGGCGAGGGAAG
AAGGGAAAGCAACTCCCGCCTCGGCACAGCTACTCATTGGTCAGAGCGGACTTCGGAGTATAACCACACGGCTGACAAAC
CTGCATCGACCGTGATGGCGTTCTTTTGGTCCAATCATGGCTGAATGCGACGTTGGTTGTGTCGGCCCTGCAGCCAATG
AGAAGCTGGTCCGATCCTGGGGACGAGGGAGAGGCAAGCATATCGTATAAGTCCAAGCTCAAGCTTGGCGGCAGGTACCG
GTTGATGTGGTCGCTGTATATAAGTAAAAGAACTCGATTCCGCTTCGGAGTTTTCTCTGTCACCCTTCATGGACGAAGAG
CTATTGAGCCGCATCTTTGCTTCGTTGTCCAGCGTGAATTCTCCTACA FIGS. 5A and 5B

```
AAGCTTACTAGTACTTCTCGAGCTCTGTACATGTCCGGTCGCGACGTACGCGTATCGATGGCGCCAGCT
GCAGGCGGCCGCCTGCAGCCACTTGCAGTCCCGTGGAATTCTCACGGTGAATGTAGGCCTTTTGTAGGG
TAGGAATTGTCACTCAAGCACCCCCAACCTCCATTACGCCTCCCCCATAGAGTTCCCAATCAGTGAGTC
ATGGCACTGTTCTCAAATAGATTGGGGAGAAGTTGACTTCCGCCCAGAGCTGAAGGTCGCACAACCGCA
TGATATAGGGTCGGCAACGGCAAAAAAGCACGTGGCTCACCGAAAAGCAAGATGTTTGCGATCTAACAT
CCAGGAACCTGGATACATCCATCATCACGCACGACCACTTTGATCTGCTGGTAAACTCGTATTCGCCCT
AAACCGAAGTGCGTGGTAAATCTACACGTGGGCCCCTTTCGGTATACTGCGTGTGTCTTCTAGGTGC
CATTCTTTTCCCTTCCTCTAGTGTTGAATTGTTTGTGTTGGAGTCCGAGCTGTAACTACCTCTGAATCT
CTGGAGAATGGTGGACTAACGACTACCGTGCACCTGCATCATGTATATAATAGTGATCCTGAGAAGGGG
GGTTTGGAGCAATGTGGGACTTTGATGGTCATCAAACAAAGAACGAAGACGCCTCTTTTGCAAAGTTTT
GTTTCGGCTACGGTGAAGAACTGGATACTTGTTGTGTCTTCTGTGTATTTTTGTGGCAACAAGAGGCCA
GAGACAATCTATTCAAACACCAAGCTTGCTCTTTTGAGCTACAAGAACCTGTGGGGTATATATCTAGAG
TTGTGAAGTCGGTAATCCCGCTGTATAGTAATACGAGTCGCATCTAAATACTCCGAAGCTGCTGCGAAC
CCGGAGAATCGAGATGTGCTGGAAAGCTTCTAGCGAGCGGCTAAATTAGCATGAAAGGCTATGAGAAAT
TCTGGAGACGGCTTGTTGAATCATGGCGTTCCATTCTTCGACAAGCAAAGCGTTCCGTCGCAGTAGCAG
GCACTCATTCCCGAAAAAACTCGGAGATTCCTAAGTAGCGATGGAACCGGAATAATATAATAGGCAATA
CATTGAGTTGCCTCGACGGTTGCAATGCAGGGGTACTGAGCTTGGACATAACTGTTCCGTACCCCACCT
CTTCTCAACCTTTGGCGTTTCCCTGATTCAGCGTACCCGTACAAGTCGTAATCACTATTAACCCAGACT
GACCGGACGTGTTTTGCCCTTCATTTGGAGAAATAATGTCATTGCGATGTGTAATTTGCCTGCTTGACC
GACTGGGGCTGTTCGAAGCCCGAATGTAGGATTGTTATCCGAACTCTGCTCGTAGAGGCATGTTGTGAA
TCTGTGTCGGGCAGGACACGCCTCGAAGGTTCACGGCAAGGGAAACCACCGATAGCAGTGTCTAGTAGC
AACCTGTAAAGCCGCAATGCAGCATCACTGGAAAATACAAACCAATGGCTAAAAGTACATAAGTTAATG
CCTAAAGAAGTCATATACCAGCGGCTAATAATTGTACAATCAAGTGGCTAAACGTACCGTAATTTGCCA
ACGGCTTGTGGGGTTGCAGAAGCAACGGCAAAGCCCCACTTCCCCACGTTTGTTTCTTCACTCAGTCCA
ATCTCAGCTGGTGATCCCCCAATTGGGTCGCTTGTTTGTTCCGGTGAAGTGAAAGAAGACAGAGGTAAG
AATGTCTGACTCGGAGCGTTTTGCATACAACCAAGGGCAGTGATGGAAGACAGTGAAATGTTGACATTC
AAGGAGTATTTAGCCAGGGATGCTTGAGTGTATCGTGTAAGGAGGTTTGTCTGCCGATACGACGAATAC
TGTATAGTCACTTCTGATGAAGTGGTCCATATTGAAATGTAAAGTCGGCACTGAACAGGCAAAAGATTG
AGTTGAAACTGCCTAAGATCTCGGGCCCTCGGGCCTTCGGCCTTTGGGTGTACATGTTTGTGCTCCGGG
CAAATGCAAAGTGTGGTAGGATCGAACACACTGCTGCCTTTACCAAGCAGCTGAGGGTATGTGATAGGC
AAATGTTCAGGGGCCACTGCATGGTTTCGAATAGAAAGAGAAGCTTAGCCAAGAACAATAGCCGATAAA
GATAGCCTCATTAAACGGAATGAGCTAGTAGGCAAAGTCAGCGAATGTGTATATATAAAGGTTCGAGGT
CCGTGCCTCCCTCATGCTCTCCCCATCTACTCATCAACTCAGATCCTCCAGGAGACTTGTACACCATCT
TTTGAGGCACAGAAACCCAATAGTCAACCATCACAAGTTTGTACAAAAAAGCAGGCTATGCACGTCCTG
TCGACTGCGGTGCTGCTCGGCTCCGTTGCCGTTCAAAAGGTCCTGGGAAGACCAGGATCAAGCGGTCTG
TCCGACGTCACCAAGAGGTCTGTTGACGACTTCATCAGCACCGAGACGCCTATTGCACTGAACAATCTT
CTTTGCAATGTTGGTCCTGATGGATGCCGTGCATTCGGCACATCAGCTGGTGCGGTGATTGCATCTCCC
AGCACAATTGACCCGGACTGTAAGTTGGCCTTGATGAACCATATCATATATCGCCGAGAAGTGGACCGC
GTGCTGAGACTGAGACAGACTATTACATGTGGACGCGAGATAGCGCTCTTGTCTTCAAGAACCTCATCG
ACCGCTTCACCGAAACGTACGATGCGGGCCTGCAGCGCCGCATCGAGCAGTACATTACTGCCCAGGTCA
CTCTCCAGGGCCTCTCTAACCCCTCGGGCTCCCTCGCGGACGGCTCTGGTCTCGGCGAGCCCAAGTTTG
AGTTGACCCTGAAGCCTTTCACCGGCAACTGGGGTCGACCGCAGCGGGATGGCCCAGCTCTGCGAGCCA
TTGCCTTGATTGGATACTCAAAGTGGCTCATCAACAACAACTATCAGTCGACTGTGTCCAACGTCATCT
GGCCTATTGTGCGCAACGACCTCAACTATGTTGCCCAGTACTGGTCAGTGCTTGCTTGCTCTTGAATTA
CGTCTTTGCTTGTGTGTCTAATGCCTCCACCACAGGAACCAAACCGGCTTTGACCTCTGGGAAGAAGTC
AATGGGAGCTCATTCTTTACTGTTGCCAACCAGCACCGAGGTATGAAGCAAATCCTCGACATTCGCTGC
TACTGCACATG
```

FIG. 6 page 1 of 4

```
AGCATTGTTACTGACCAGCTCTACAGCACTTGTCGAGGGCGCCACTCTTGCTGCCACTCTTGGCCAGTC
GGGAAGCGCTTATTCATCTGTTGCTCCCCAGGTTTTGTGCTTTCTCCAACGATTCTGGGTGTCGTCTGG
TGGATACGTCGACTCCAACAGTATGTCTTTTCACTGTTTATATGAGATTGGCCAATACTGATAGCTCGC
CTCTAGTCAACACCAACGAGGGCAGGACTGGCAAGGATGTCAACTCCGTCCTGACTTCCATCCACACCT
TCGATCCCAACCTTGGCTGTGACGCAGGCACCTTCCAGCCATGCAGTGACAAAGCGCTCTCCAACCTCA
AGGTTGTTGTCGACTCCTTCCGCTCCATCTACGGCGTGAACAAGGGCATTCCTGCCGGTGCTGCCGTCG
CCATTGGCCGGTATGCAGAGGATGTGTACTACAACGGCAACCCTTGGTATCTTGCTACATTTGCTGCTG
CCGAGCAGCTGTACGATGCCATCTACGTCTGGAAGAAGACGGGCTCCATCACGGTGACCGCCACCTCCC
TGGCCTTCTTCCAGGAGCTTGTTCCTGGCGTGACGGCCGGGACCTACTCCAGCAGCTCTTCGACCTTTA
CCAACATCATCAACGCCGTCTCGACATACGCCGATGGCTTCCTCAGCGAGGCTGCCAAGTACGTCCCCG
CCGACGGTTCGCTGGCCGAGCAGTTTGACCGCAACAGCGGCACTCCGCTGTCTGCGCTTCACCTGACGT
GGTCGTACGCCTCGTTCTTGACAGCCACGGCCCGTCGGGCTGGCATCGTGCCCCCCTCGTGGGCCAACA
GCAGCGCTAGCACGATCCCCTCGACGTGCTCCGGCGCGTCCGTGGTCGGATCCTACTCGCGTCCCACCG
CCACGTCATTCCCTCCGTCGCAGACGCCCAAGCCTGGCGTGCCTTCCGGTACTCCCTACACGCCCTGC
CCTGCGCGACCCCAACCTCCGTGGCCGTCACCTTCCACGAGCTCGTGTCGACACAGTTTGGCCAGACGG
TCAAGGTGGCGGGCAACGCCGCGGCCCTGGGCAACTGGAGCACGAGCGCCGCCGTGGCTCTGGACGCCG
TCAACTATGCCGATAACCACCCCCTGTGGATTGGGACGTCAACCTCGAGGCTGGAGACGTCGTGGAGT
ACAAGTACATCAATGTGGGCCAAGATGGCTCCGTGACCTGGGAGAGTGATCCCAACCACACTTACACGG
TTCCTGCGGTGGCTTGTGTGACGCAGGTTGTCAAGGAGGACACCTGGCAGTCGTAAACCCAGCTTTCTT
GTACAAAGTGGTGATCGCGCCAGCTCCGTGCGAAAGCCTGACGCACCGGTAGATTCTTGGTGAGCCCGT
ATCATGACGGCGGCGGGAGCTACATGGCCCCGGGTGATTTATTTTTTTTGTATCTACTTCTGACCCTTT
TCAAATATACGGTCAACTCATCTTTCACTGGAGATGCGGCCTGCTTGGTATTGCGATGTTGTCAGCTTG
GCAAATTGTGGCTTTCGAAAACACAAAACGATTCCTTAGTAGCCATGCATTTTAAGATAACGGAATAGA
AGAAAGAGGAAATTAAAAAAAAAAAAAAAAACAAACATCCCGTTCATAACCCGTAGAATCGCCGCTGGCG
CGCCTGAGACAATGGCCGGCAATGGTAAAAAGGACCAAGATGTACTAGGTAGTTGCAATGTGGCTTATT
ACCTACCTACTACCTGGTAGGCACCTACTAGGTACTTGGGTAGACGGACAATGAAATTTGAAGTCGGGG
TTGCAGGAAAGCAGGGCGCTGGACACATTGTGCTTCAGGCGGTACCCGTCGTCATCGTCAGCCAATGTC
GAGGCCCGGCAGCCCGAGGAGCGAGACAACCTTGGCCGGAGGAGCCCGCAGGTACCTGCCAAAGCGCGG
CTGGTACCTCTCAACCCTCTCAGGCCTGTTGGATGCCCTATGACATGCCCTGGGGATGCAGCTGTTGC
CCCGGCCCCGCACTTTCGGGTGACCGCGAGGCTGCTGATTGGCTGGTTGCCACGGGCTGGGCGGTCCCT
GAAGTTGTTGCCATCTGAACTCTGTCGGCGCTGGCGTCGGCTGCGCCCAATGGGAGGCGAGACAACTCA
GGGTACTAGAATCACTGACAGAAGAAGAGAATCGAAAGTAGGTAGACAGCCAATTCGTTGCATGGCAGG
CAACCGCACAGGAGAAAAATTGACTACCCCACAATCAGGCACAGTAAGTAGGGCACAGTACGTATGTAC
AGACAAGGCGCAAGCGATACTGCGCGACCCGGTACCTCGCCGGCTTGACACGTGCGACAGGCTACTTTA
CTAGTATTCGCAGCGGCGGGTCGCGCATTATTACATGTACTGTGCCGCCATTTGATGACTGGGCTGCTG
CAGTATTAGTAGATCTGCCCGGCATCGCCCTTCCATGGGCGCGACCCGGGACTGGACCCTCTGACTCTA
CCTACATGTACCTAGGCCGGGCCGGGCTTGGTGACTTTTGTCCGATCAGGTCGTTCGCCTGGCTACCTA
TTATTTCTCTTTCTTCTTCTCCATCCTGCTTCTGGCCTTGCAATTCTTCTTCGCCACTCCTCCCTCTTC
CCCCCGCGATACCCTTGAATTCGTCAGAGAGGAAAAGACGAGAAAAAAAGGGCAGCAGAGACGTCGGT
CTGGCTCACGTGCTGCATCTCTGCGCACTCTCATTTTTTTTTATTGTCCGACCCCTCCCTCAACCTTCTC
CTTCGTTGACAGGCTAAGCCTTGCTTCGACGCTCTCTCTTTGAATTTTTCTACTTCTACCTTCTTTTCT
TGCGTGTTACCCACCATAGCTCGATTCACGATGCTCCGAAGTCGCCAAGTCACAGCCAGGGCCGTCCGG
GCTCTGGGCCAGGCGCGCGCCTTTACCTCGACGACCAAGCCTGTCATGATCCAGAGCAGCCAGAGGAAA
CAGGCCAACGCCAGCGCTGCTCCGTAAGTCGCCCATTGCCATTGCATCTTCTGTTTGATATATACTTCC
TGCTGCTTGCGTGGCGTCG
```

FIG. 6 page 2 of 4

```
TCTCTCGGTTATGCGTGTCAAGGACCAGGTGTGTTCGCATCGTGGTTTTCCAGCGCCGATTACCGGG
GGACGAATTTTTGGCTGCTCAACTCGCGCGCGCATTCTGATTCTTCGTTTTCAATCTTGAGCGAC
AACTGGCTAACATAATGGCCATTGGCAATTGCTTCACACAGACAAGTCCGCCCTGTACCGAGCCCTG
CTTTCAACGCTGAAGACAAAGACCGCAGCCATGTGCAGCCTCTGGTCAACCCGTCGAAGCCCGACAT
GGATGAATCGTATGTCCACGTCCCCTCGTCCCGCCCTACAAAATGAACACGATTACACCAGAATTTT
TGCAACAATCGACACTTCTATAACAGACCAATTGAGCTTTGTTCTGACCAATCATGTTGCTCTAGAT
TCATTGGCAAAACCGGAGGCGAAATCTTCCACGAGATGATGCTGCGACAGGGTGTCAAGCACATTTG
TAGGTTCCGATGCCGGCCGCCCACACGGGCTCCATCCTTGCTCCATCTCTCCAGCTAGGCAAATCTC
GCTAACCTTGAGTCACCATCCAGTCGGATACCCTGGCGGCGCTATCCTGCCCGTCTTCGACGCCATC
TACAACTCAAAACACTTCGACTTCATCCTGCCCCGTCATGAGCAGGGAGCTGGCCATATGGCCGAGG
GCTATGCCCGTGCCTCGGGCAAACCCGGTGTCGTCCTGGTGACTTCCGGCCCCGGTGCTACCAATGT
CATCACGCCCATGCAGGATGCCCTGTCGGACGGAACGCCCTTGGTCGTCTTCTGCGGCCAGGTCCCC
ACCACGGCCATCGGCAGCGATGACTTCCAAGAGGCCGACGTCGTGGGCATCTCGCGGGCCTGCACCA
AGTGGAACGTCATGGTCAAGAGCGTTGCTGAGCTGCCGCGGAGAATCAACGAGGCCTTTGAGATTGC
CACCAGCGGCCGCCCTGGCCCCGTCCTCGTCGACCTGCCCAAGGATGTCACGGCTGGTATCCTGAGG
AGAGCCATCCCTACGGAGACTGCTCTGCCGTCTCTGCCCAGTGCCGCCTCCCGCGCCGCCATGGAGC
TGAGCTCCAAGCAGCTCAACGCCTCCATCAAGCGTGCCGCCGACCTCATCAACATCGCCAAGAAGCC
CGTCATCTACGCCGGTCAGGGTGTCATCCAGTCCGAGGGCGGCGTTGAGCTCCTGAAGCAGCTGGCG
GACAAGGCCTCCATCCCCGTCACCACCACCCTCCATGGCCTGGGTGCCTTTGATGAGCTGGACGAGA
AGTCGCTGCACATGCTGGGCATGCACGGCTCGGCGTATGCCAACATGGCCATGCAGCAGGCCGACCT
CATCATCGCCCTCGGCAGCCGATTCGACGACCGTGTTACTCTGAATGTCTCCAAATTTGCGCCTGCA
GCCAGGCAAGCTGCTGCCGAGGGCCGCGGCGGCATCATTCACTTTGAGATCATGCCCAAGAACATCA
ACAAGGTCATCCAGGCGACCGAGGCCGTCGAGGGCGACGTCGCCACCAACCTGAAGCACCTCATTCC
CCAGATTGCCGAAAAGTCCATGGCGGACCGAGGAGAGTGGTTCGGCCTCATCAATGAGTGGAAGAAG
AAGTGGCCCCTGTCAAACTACCAGCGCGCGGAGCGGGCTGGCCTCATCAAGCCGCAGACGGTCATGG
AGGAGATTAGCAACCTGACGGCCAACCGAAAGGACAAGACGTACATTGCCACGGGTGTCGGCCAGCA
CCAGATGTGGGTTGCCCAGCACTTCCGCTGGAGGCACCCTCGATCCATGATTACCTCTGGTGGTCTG
GGCACCATGGGCTACGGTCTCCCCGCGGCCATTGGCGCCAAGGTGGCCCAGCCCGACGCTCTCGTAA
TTGACGTTGATGGCGATGCCTCGTTTAACATGACGCTGACGGAGCTGTCGACTGCTGCACAGTTCAA
CATTGGCGTCAAGGTGGTTGTGCTCAACAACGAGGAGCAGGGCATGGTGACGCAGTGGCAGAACCTC
TTTTACGAGGACCGATATGCCCACACGCACCAGAAGAACCCCGACTTCATGAAGCTGGCCGACGCCA
TGGGCGTTCAGCACCAGCGCGTGACGGAGCCGGAGAAGCTGGTCGATGCCCTGACGTGGCTGATCAA
CACCGATGGCCCGGCCCTGTTGGAGGTTGTCACGGACAAGAAGGTGCCTGTCCTGCCCATGGTGCCC
GCCGGATCGGCCCTGCACGAGTTCCTCGTCTTTGAACCTGGTGAGTCTACTTCAGACATATTGCTTG
CGCATTGCAGATACTAACACTCTCACAGAAAAGGATAAGCAGCGCCGTGAGCTGATGAAGGAGAGAA
CAAAGGGTGTGCACTCCTAAAGCGATGATGTCTGCGAGGGGTTCTTCGTTGAACCCTAGTTCAGGCA
CCATCTTACCCTCTTATTTTTTCCCGTGGGCTTTCATTTTGTGTCATCCGAGCATGACGTTGTAGGG
TTGGAGTTTCTTCCTTTTTATCTTGTCATTTACTGGTACCCATAGGCGCGAGACTAGGCTTCCATGT
TTTGTTTTGCGACTTTCAAAAAGTACTTTTAGTGGTTTGGGGCACGACGAGGGGGGCAACCTCTTC
TGTCGAAAAAGGTGGCTGGATGGATGAGATGAGATGAGATGAGGGTGAAGATAGATACCTGCAGTGT
TTTTGACGCGACGGGATGGCGATCGCTCAGGGTTGCGTTTCCAGTCTAGACACGTATAACGGCACAA
GTGTCTCTCACCAAATGGGTTATATCTCAAATGTGATCTAAGGATGGAAAGCCCAGAATATCGATCG
CGCGCAGATCCATATATAGGGCCCGGGTTATAATTACCTCAGGTCGACGTCCCATGGCCATTCGAAT
TCGTAATCATGGTCATAGCTGTTTCCTGTGTGAAATTGTTATCCGCTCACAATTCCACACAACATAC
GAGCCGGAAGCATAAAGTGTAAAGCCTGGGGTGCCTAATGAG
```

FIG. 6 page 3 of 4

```
TGAGCTAACTCACATTAATTGCGTTGCGCTCACTGCCCGCTTTCCAGTCGGGAAACCTGTCGTGCCAG
CTGCATTAATGAATCGGCCAACGCGCGGGGAGAGGCGGTTTGCGTATTGGGCGCTCTTCCGCTTCCTC
GCTCACTGACTCGCTGCGCTCGGTCGTTCGGCTGCGGCGAGCGGTATCAGCTCACTCAAAGGCGGTAA
TACGGTTATCCACAGAATCAGGGGATAACGCAGGAAAGAACATGTGAGCAAAAGGCCAGCAAAAGGCC
AGGAACCGTAAAAAGGCCGCGTTGCTGGCGTTTTTTCCATAGGCTCCGCCCCCCTGACGAGCATCACAA
AAATCGACGCTCAAGTCAGAGGTGGCGAAACCCGACAGGACTATAAAGATACCAGGCGTTTCCCCCTG
GAAGCTCCCTCGTGCGCTCTCCTGTTCCGACCCTGCCGCTTACCGGATACCTGTCCGCCTTTCTCCCT
TCGGGAAGCGTGGCGCTTTCTCATAGCTCACGCTGTAGGTATCTCAGTTCGGTGTAGGTCGTTCGCTC
CAAGCTGGGCTGTGTGCACGAACCCCCCGTTCAGCCCGACCGCTGCGCCTTATCCGGTAACTATCGTC
TTGAGTCCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAGAAGAAC
AGTATTTGGTATCTGCGCTCTGCTGAAGCCAGTTACCTTCGGAAAAAGAGTTGGTAGCTCTTGATCCG
GCAAACAAACCACCGCTGGTAGCGGTGGTTTTTTTGTTTGCAAGCAGCAGATTACGCGCAGAAAAAAA
GGATCTCAAGAAGATCCTTTGATCTTTTCTACGGGGTCTGACGCTCAGTGGAACGAAAACTCACGTTA
AGGGATTTTGGTCATGAGATTATCAAAAAGGATCTTCACCTAGATCCTTTTAAATTAAAAATGAAGTT
TTAAATCAATCTAAAGTATATATGAGTAAACTTGGTCTGACAGTTACCAATGCTTAATCAGTGAGGCA
CCTATCTCAGCGATCTGTCTATTTCGTTCATCCATAGTTGCCTGACTCCCCGTCGTGTAGATAACTAC
GATACGGGAGGGCTTACCATCTGGCCCCAGTGCTGCAATGATACCGCGAGACCCACGCTCACCGGCTC
CAGATTTATCAGCAATAAACCAGCCAGCCGGAAGGGCCGAGCGCAGAAGTGGTCCTGCAACTTTATCC
GCCTCCATCCAGTCTATTAATTGTTGCCGGGAAGCTAGAGTAAGTAGTTCGCCAGTTAATAGTTTGCG
CAACGTTGTTGCCATTGCTACAGGCATCGTGGTGTCACGCTCGTCGTTTGGTATGGCTTCATTCAGCT
CCGGTTCCCAACGATCAAGGCGAGTTACATGATCCCCATGTTGTGCAAAAAAGCGGTTAGCTCCTTC
GGTCCTCCGATCGTTGTCAGAAGTAAGTTGGCCGCAGTGTTATCACTCATGGTTATGGCAGCACTGCA
TAATTCTCTTACTGTCATGCCATCCGTAAGATGCTTTTCTGTGACTGGTGAGTACTCAACCAAGTCAT
TCTGAGAATAGTGTATGCGGCGACCGAGTTGCTCTTGCCCGGCGTCAATACGGGATAATACCGCGCCA
CATAGCAGAACTTTAAAAGTGCTCATCATTGGAAAACGTTCTTCGGGGCGAAAACTCTCAAGGATCTT
ACCGCTGTTGAGATCCAGTTCGATGTAACCCACTCGTGCACCCAACTGATCTTCAGCATCTTTTACTT
TCACCAGCGTTTCTGGGTGAGCAAAAACAGGAAGGCAAAATGCCGCAAAAAAGGGAATAAGGGCGACA
CGGAAATGTTGAATACTCATACTCTTCCTTTTTCAATATTATTGAAGCATTTATCAGGGTTATTGTCT
CATGAGCGGATACATATTTGAATGTATTTAGAAAAATAAACAAATAGGGGTTCCGCGCACATTTCCCC
GAAAAGTGCCACCTGACGTCTAAGAAACCATTATTATCATGACATTAACCTATAAAAATAGGCGTATC
ACGAGGCCCTTTCGTCTCGCGCGTTTCGGTGATGACGGTGAAAACCTCTGACACATGCAGCTCCCGGA
GACGGTCACAGCTTGTCTGTAAGCGGATGCCGGGAGCAGACAAGCCCGTCAGGGCGCGTCAGCGGGTG
TTGGCGGGTGTCGGGGCTGGCTTAACTATGCGGCATCAGAGCAGATTGTACTGAGAGTGCACCATAAA
ATTGTAAACGTTAATATTTTGTTAAAATTCGCGTTAAATTTTTGTTAAATCAGCTCATTTTTTAACCA
ATAGGCCGAAATCGGCAAAATCCCTTATAAATCAAAAGAATAGCCCGAGATAGGGTTGAGTGTTGTTC
CAGTTTGGAACAAGAGTCCACTATTAAAGAACGTGGACTCCAACGTCAAAGGGCGAAAAACCGTCTAT
CAGGGCGATGGCCCACTACGTGAACCATCACCCAAATCAAGTTTTTTGGGGTCGAGGTGCCGTAAAGC
ACTAAATCGGAACCCTAAAGGGAGCCCCCGATTTAGAGCTTGACGGGGAAAGCCGGCGAACGTGGCGA
GAAAGGAAGGGAAGAAAGCGAAAGGAGCGGGCGCTAGGGCGCTGGCAAGTGTAGCGGTCACGCTGCGC
GTAACCACCACACCCGCCGCGCTTAATGCGCCGCTACAGGGCGCGTACTATGGTTGCTTTGACGTATG
CGGTGTGAAATACCGCACAGATGCGTAAGGAGAAAATACCGCATCAGGCGCCATTCGCCATTCAGGCT
GCGCAACTGTTGGGAAGGGCGATCGGTGCGGGCCTCTTCGCTATTACGCCAGCTGGCGAAAGGGGGAT
GTGCTGCAAGGCGATTAAGTTGGGTAACGCCAGGGTTTTCCCAGTCACGACGTTGTAAAACGACGGCC
AGTGCCC
```

FIG. 6 page 4 of 4

```
CATTACGCCTCCCCCATAGATAGGTCTAGGCTGGCGGGTTGGTGCTTTTGCCCTTTGTCTGCCGCGACC
TCTTGGTGACGCTGCATCGTGTTGGCTGTAGCTGCACGCCCGGCCTCTTTTCTGGCATCTCGCACAGAC
TGTACGCAGAACATGTGTAAGTGACTTTCTATTGTAGGACTTGGATGGATGGGAGATGGCTATAGACAA
CAAGAGCGACAACAAGGATTATAGACAGTTCCATTACCTGGGCGACCACCATCGCACTTCACCTTGCTC
GCCCGGCAGGACTGGCAGGCGTTGGCAATCTTGAGTCGCTCCCTGTACAGCGACAAGGGCGCCTGAGCC
TGCACCTGAGCCTGGGCCTGAGTCTGAGCCTGAAGCCGTTGATCCTCGTCTTGACGGGCGGACATGACG
CTTTACGTGAGCTGAGTCCAGGGCTGTCGTCGGCAAGTGATTCGGCAGCCGGCAGGCACAGACGAAAGA
TAAGAAGCGGCTCGTTCACCAGATCCGAAGGCGGAATGCAAGAATGTCCGATGATGTCGGGGAAGAGAA
GGCGATGCCTCGTCTATCTGGGAGGCGAGGGAAGAAGGGAAAGCAACTCCCGCCTCGGCACAGCTACTC
ATTGGTCAGAGCGGACTTCGGAGTATAACCACACGGCTGACAAACCTGCATCGACCGTGATGGCGTTCT
TTTGGTCCAATCATGGCTGAATGCGACGTTGGTTGTGTCGGCCCCTGCAGCCAATGAGAAGCTGGTCCG
ATCCTGGGGACGAGGGAGAGGCAAGCATATCGTATAAGTCCAAGCTCAAGCTTGGCGGCAGGTACCGGT
TGATGTGGTCGCTGTATATAAGTAAAAGAACTCGATTCCGCTTCGGAGTTTTCTCTGTCACCCTTCACA
AGTTTGTACAAAAAAGCAGGCTATGCACGTCCTGTCGACTGCGGTGCTGCTCGGCTCCGTTGCCGTTCA
AAAGGTCCTGGGAAGACCAGGATCAAGCGGTCTGTCCGACGTCACCAAGAGGTCTGTTGACGACTTCAT
CAGCACCGAGACGCCTATTGCACTGAACAATCTTCTTTGCAATGTTGGTCCTGATGGATGCCGTGCATT
CGGCACATCAGCTGGTGCGGTGATTGCATCTCCAGCACAATTGACCCGGACTGTAAGTTGGCCTTGAT
GAACCATATCATATATCGCCGAGAAGTGGACCGCGTGCTGAGACTGAGACAGACTATTACATGTGGACG
CGAGATAGCGCTCTTGTCTTCAAGAACCTCATCGACCGCTTCACCGAAACGTACGATGCGGGCCTGCAG
CGCCGCATCGAGCAGTACATTACTGCCCAGGTCACTCTCCAGGGCCTCTCTAACCCCTCGGGCTCCCTC
GCGGACGGCTCTGGTCTCGGCGAGCCCAAGTTTGAGTTGACCCTGAAGCCTTTCACCGGCAACTGGGGT
CGACCGCAGCGGGATGGCCCAGCTCTGCGAGCCATTGCCTTGATTGGATACTCAAAGTGGCTCATCAAC
AACAACTATCAGTCGACTGTGTCCAACGTCATCTGGCCTATTGTGCGCAACGACCTCAACTATGTTGCC
CAGTACTGGTCAGTGCTTGCTTGCTCTTGAATTACGTCTTTGCTTGTGTGTCTAATGCCTCCACCACAG
GAACCAAACCGGCTTTGACCTCTGGGAAGAAGTCAATGGGAGCTCATTCTTTACTGTTGCCAACCAGCA
CCGAGGTATGAAGCAAATCCTCGACATTCGCTGCTACTGCACATGAGCATTGTTACTGACCAGCTCTAC
AGCACTTGTCGAGGGCGCCACTCTTGCTGCCACTCTTGGCCAGTCGGGAAGCGCTTATTCATCTGTTGC
TCCCCAGGTTTTGTGCTTTCTCCAACGATTCTGGGTGTCGTCTGGTGGATACGTCGACTCCAACAGTAT
GTCTTTTCACTGTTTATATGAGATTGGCCAATACTGATAGCTCGCCTCTAGTCAACACCAACGAGGGCA
GGACTGGCAAGGATGTCAACTCCGTCCTGACTTCCATCCACACCTTCGATCCCAACCTTGGCTGTGACG
CAGGCACCTTCCAGCCATGCAGTGACAAAGCGCTCTCCAACCTCAAGGTTGTTGTCGACTCCTTCCGCT
CCATCTACGGCGTGAACAAGGGCATTCCTGCCGGTGCTGCCGTCGCCATTGCCGGTATGCAGAGGATG
TGTACTACAACGGCAACCCTTGGTATCTTGCTACATTTGCTGCTGCCGAGCAGCTGTACGATGCCATCT
ACGTCTGGAAGAAGACGGGCTCCATCACGGTGACCGCCACCTCCCTGGCCTTCTTCCAGGAGCTTGTTC
CTGGCGTGACGGCCGGGACCTACTCCAGCAGCTCTTCGACCTTTACCAACATCATCAACGCCGTCTCGA
CATACGCCGATGGCTTCCTCAGCGAGGCTGCCAAGTACGTCCCCGCCGACGGTTCGCTGGCCGAGCAGT
TTGACCGCAACAGCGGCACTCCGCTGTCTGCGCTTCACCTGACGTGGTCGTACGCCTCGTTCTTGACAG
CCACGGCCCGTCGGGCTGGCATCGTGCCCCCTCGTGGGCCAACAGCAGCGCTAGCACGATCCCCTCGA
CGTGCTCCGGCGCGTCCGTGGTCGGATCCTACTCGCGTCCCACCGCCACGTCATTCCTCCGTCGCAGA
CGCCCAAGCCTGGCGTGCCTTCCGGTACTCCCTACACGCCCCTGCCCTGCGCGACCCCAACCTCCGTGG
CCGTCACCTTCCACGAGCTCGTGTCGACACAGTTTGGCCAGACGGTCAAGGTGGCGGGCAACGCCGCGG
CCCTGGGCAACTGGAGCACGAGCGCCGCCGTGGCTCTGGACGCCGTCAACTATGCCGATAACCACCCCC
TGTGGATTGGGACGGTCAACCTCGAGGCTGGAGACGTCG
```

Fig. 9A

```
TGGAGTACAAGTACATCAATGTGGGCCAAGATGGCTCCGTGACCTGGGAGAGTGATCCCAACCACACT
TACACGGTTCCTGCGGTGGCTTGTGTGACGCAGGTTGTCAAGGAGGACACCTGGCAGTCGTAAACCCA
GCTTTCTTGTACAAAGTGGTGATCGCGCCAGCTCCGTGCGAAAGCCTGACGCACCGGTAGATTCTTGG
TGAGCCCGTATCATGACGGCGGCGGGAGCTACATGGCCCCGGGTGATTTATTTTTTTGTATCTACTT
CTGACCCTTTTCAAATATACGGTCAACTCATCTTTCACTGGAGATGCGGCCTGCTTGGTATTGCGATG
TTGTCAGCTTGGCAAATTGTGGCTTTCGAAAACACAAAACGATTCCTTAGTAGCCATGCATTTTAAGA
TAACGGAATAGAAGAAAGAGGAAATTAAAAAAAAAAAAAAAACAAACATCCCGTTCATAACCCGTAGA
ATCGCCGCTGGCGCGCCTGAGACAATGGCCGGCAATGGTAAAAAGGACCAAGATGTACTAGGTAGTTG
CAATGTGGCTTATTACCTACCTACTACCTGGTAGGCACCTACTAGGTACTTGGGTAGACGGACAATGA
AATTTGAAGTCGGGGTTGCAGGAAAGCAGGGCGCTGGACACATTGTGCTTCAGGCGGTACCCGTCGTC
ATCGTCAGCCAATGTCGAGGCCCGGCAGCCCGAGGAGCGAGACAACCTTGGCCGGAGGAGCCCGCAGG
TACCTGCCAAAGCGCGGCTGGTACCTCTCAACCCTCTCAGGCCTGTTGGATGCCCTATGACATGCCCT
GGGGGATGCAGCTGTTGCCCCGGCCCCGCACTTTCGGGTGACCGCGAGGCTGCTGATTGGCTGGTTGC
CACGGGCTGGGCGGTCCCTGAAGTTGTTGCCATCTGAACTCTGTCGGCGCTGGCGTCGGCTGCGCCCA
ATGGGAGGCGAGACAACTCAGGGTACTAGAATCACTGACAGAAGAAGAGAATCGAAAGTAGGTAGACA
GCCAATTCGTTGCATGGCAGGCAACCGCACAGGAGAAAAATTGACTACCCCACAATCAGGCACAGTAA
GTAGGGCACAGTACGTATGTACAGACAAGGCGCAAGCGATACTGCGCGACCCGGTACCTCGCCGGCTT
GACACGTGCGACAGGCTACTTTACTAGTATTCGCAGCGGCGGGTCGCGCATTATTACATGTACTGTGC
CGCCATTTGATGACTGGGCTGCTGCAGTATTAGTAGATCTGCCCGGCATCGCCCTTCCATGGGCGCGA
CCCGGGACTGGACCCTCTGACTCTACCTACATGTACCTAGGCCGGGCCGGGCTTGGTGACTTTGTCC
GATCAGGTCGTTCGCCTGGCTACCTATTATTTCTCTTTCTTCTTCTCCATCCTGCTTCTGGCCTTGCA
ATTCTTCTTCGCCACTCCTCCCTCTTCCCCCCGCGATACCCTTGAATTCGTCAGAGAGGAAAAGACGA
GAAAAAAAGGGCAGCAGAGACGTCGGTCTGGCTCACGTGCTGCATCTCTGCGCACTCTCATTTTTTT
TATTGTCCGACCCCTCCCTCAACCTTCTCCTTCGTTGACAGGCTAAGCCTTGCTTCGACGCTCTCTCT
TTGAATTTTTCTACTTCTACCTTCTTTCTTGCGTGTTACCCACCATAGCTCGATTCACGATGCTCCG
AAGTCGCCAAGTCACAGCCAGGGCCGTCCGGGCTCTGGGCCAGGCGCGCGCCTTTACCTCGACGACCA
AGCCTGTCATGATCCAGAGCAGCCAGAGGAAACAGGCCAACGCCAGCGCTGCTCCGTAAGTCGCCCAT
TGCCATTGCATCTTCTGTTTGATATATACTTCCTGCTGCTTGCGTGGCGTCGTCTCTCGGTTATGCGT
GTCAAGGACCAGGTGTGTTCGCATCGTGGTTTTCCAGCGCCGATTACCGGGGACGAATTTTTGGCTG
CTCAACTCGCGCGCGCGCATTCTGATTCTTCGTTTTCAATCTTGAGCGACAACTGGCTAACATAATGG
CCATTGGCAATTGCTTCACACAGACAAGTCCGCCCTGTACCGAGCCCTGCTTTCAACGCTGAAGACAA
AGACCGCAGCCATGTGCAGCCTCTGGTCAACCCGTCGAAGCCCGACATGGATGAATCGTATGTCCACG
TCCCCTCGTCCGCCCTACAAAATGAACACGATTACACCAGAATTTTTGCAACAATCGACACTTCTAT
AACAGACCAATTGAGCTT
```

Fig. 9B

```
TGTTCTGACCAATCATGTTGCTCTAGATTCATTGGCAAAACCGGAGGCGAAATCTTCCACGAGATGA
TGCTGCGACAGGGTGTCAAGCACATTTGTAGGTTCCGATGCCGGCCGCCCACACGGGCTCCATCCTT
GCTCCATCTCTCCAGCTAGGCAAATCTCGCTAACCTTGAGTCACCATCCAGTCGGATACCCTGGCGG
CGCTATCCTGCCCGTCTTCGACGCCATCTACAACTCAAAACACTTCGACTTCATCCTGCCCCGTCAT
GAGCAGGGAGCTGGCCATATGGCCGAGGGCTATGCCCGTGCCTCGGGCAAACCGGTGTCGTCCTGG
TGACTTCCGGCCCCGGTGCTACCAATGTCATCACGCCCATGCAGGATGCCCTGTCGGACGGAACGCC
CTTGGTCGTCTTCTGCGGCCAGGTCCCCACCACGGCCATCGGCAGCGATGACTTCCAAGAGGCCGAC
GTCGTGGGCATCTCGCGGGCCTGCACCAAGTGGAACGTCATGGTCAAGAGCGTTGCTGAGCTGCCGC
GGAGAATCAACGAGGCCTTTGAGATTGCCACCAGCGGCCGCCCTGGCCCCGTCCTCGTCGACCTGCC
CAAGGATGTCACGGCTGGTATCCTGAGGAGAGCCATCCCTACGGAGACTGCTCTGCCGTCTCTGCCC
AGTGCCGCCTCCCGCGCCGCCATGGAGCTGAGCTCCAAGCAGCTCAACGCCTCCATCAAGCGTGCCG
CCGACCTCATCAACATCGCCAAGAAGCCCGTCATCTACGCCGGTCAGGGTGTCATCCAGTCCGAGGG
CGGCGTTGAGCTCCTGAAGCAGCTGGCGGACAAGGCCTCCATCCCCGTCACCACCACCCTCCATGGC
CTGGGTGCCTTTGATGAGCTGGACGAGAAGTCGCTGCACATGCTGGGCATGCACGGCTCGGCGTATG
CCAACATGGCCATGCAGCAGGCCGACCTCATCATCGCCCTCGGCAGCCGATTCGACGACCGTGTTAC
TCTGAATGTCTCCAAATTTGCGCCTGCAGCCAGGCAAGCTGCTGCCGAGGGCCGCGGCGGCATCATT
CACTTTGAGATCATGCCCAAGAACATCAACAAGGTCATCCAGGCGACCGAGGCCGTCGAGGGCGACG
TCGCCACCAACCTGAAGCACCTCATTCCCCAGATTGCCGAAAAGTCCATGGCGGACCGAGGAGAGTG
GTTCGGCCTCATCAATGAGTGGAAGAAGAAGTGGCCCCTGTCAAACTACCAGCGCGCGGAGCGGGCT
GGCCTCATCAAGCCGCAGACGGTCATGGAGGAGATTAGCAACCTGACGGCCAACCGAAAGGACAAGA
CGTACATTGCCACGGGTGTCGGCCAGCACCAGATGTGGGTTGCCCAGCACTTCCGCTGGAGGCACCC
TCGATCCATGATTACCTCTGGTGGTCTGGGCACCATGGGCTACGGTCTCCCCGCGGCCATTGGCGCC
AAGGTGGCCCAGCCCGACGCTCTCGTAATTGACGTTGATGGCGATGCCTCGTTTAACATGACGCTGA
CGGAGCTGTCGACTGCTGCACAGTTCAACATTGGCGTCAAGGTGGTTGTGCTCAACAACGAGGAGCA
GGGCATGGTGACGCAGTGGCAGAACCTCTTTTACGAGGACCGATATGCCCACACGCACCAGAAGAAC
CCCGACTTCATGAAGCTGGCCGACGCCATGGGCGTTCAGCACCAGCGCGTGACGGAGCCGGAGAAGC
TGGTCGATGCCCTGACGTGGCTGATCAACACCGATGGCCCGGCCCTGTTGGAGGTTGTCACGGACAA
GAAGGTGCCTGTCCTGCCCATGGTGCCCGCCGGATCGGCCCTGCACGAGTTCCTCGTCTTTGAACCT
GGTGAGTCTACTTCAGACATATTGCTTGCGCATTGCAGATACTAACACTCTCACAGAAAAGGATAAG
CAGCGCCGTGAGCTGATGAAGGAGAGAACAAAGGGTGTGCACTCCTAAAGCGATGATGTCTGCGAGG
GGTTCTTCGTTGAACCCTAGTTCAGGCACCATCTTACCCTCTTATTTTTCCCGTGGGCTTTCATTT
TGTGTCATCCGAGCATGACGTTGTAGGGTTGGAGTTTCTTCCTTTTTATCTTGTCATTTACTGGTAC
CCATAGGCGCGAGACTAGGCTTCCATGTTTTGTTTTGCGACTTTCAAAAAGTACTTTTAGTGGTTTG
GGGCACGACGAGGGGGGGCAACCTCTTCTGTCGAAAAAGGTGGCTGGATGGATGAGATGAGATGAGA
TGAGGGTGAAGATAGATACCTGCAGTGTTTTGACGCGACGGGATGGCGATCGC
```

Fig. 9C

ACETOLACTATE SYNTHASE (ALS) SELECTABLE MARKER FROM *TRICHODERMA REESEI*

CROSS-REFERENCE TO RELATED APPLICATIONS

This application claims priority to U.S. provisional application 60/846,804, filed Sep. 22, 2006, and U.S. No. 60/846,656, filed on Sep. 22, 2006, both of which are herein incorporated by reference in entirety.

BACKGROUND

Plants, fungi and bacteria synthesize the amino acids valine, leucine and isoleucine via a common pathway. One of the enzymes in this pathway is acetolactate synthase (ALS) (otherwise known as acetohydroxyacid synthase or AHAS), which converts pyruvate into 2-acetolactate as the first step in the synthesis of valine and leucine, and also converts pyruvate and 2-ketobutyrate into 2-aceto-2-hydroxybutyrate, the precursor of isoleucine. The activity of wild-type acetolactate synthase is sensitive to the action of several known classes of toxic compounds, including sulphonylurea and imidazolinone compounds. As such, such toxic compounds may be employed to kill cells containing acetolactate synthase proteins that are sensitive to those compounds.

This disclosure relates to acetolactate synthase enzymes that provide resistance to toxic compounds, and hence are useful selectable markers for recombinant cells.

SUMMARY OF THE INVENTION

An acetolactate synthase protein that provides resistance to ALS inhibitors, e.g., sulphonylurea and imidazolinone compounds, is provided, as well as a polynucleotide encoding the same. In certain embodiments, the amino acid sequence of the acetolactate protein is at least 80% identical to SEQ ID NO:1, the wild-type acetolactate protein of *Trichoderma reesei*. In particular embodiments, the ALS protein may contain an acidic amino acid at position 190, an acidic amino acid at position 241, or a histidine at position 372. In some embodiments, the ALS gene or polypeptide may be employed as a selectable marker in a wide variety of species. In certain cases, the protein may be non-naturally occurring.

In certain embodiments, a polynucleotide encoding ALS may be operably linked to a promoter and a terminator to provide for expression of the ALS inhibitor resistance-conferring protein in a host cell. The promoter and terminator may be endogenous to the host cell in which the polynucleotide is to be employed, and, in certain cases, the promoter and terminator may be the promoter and terminator of an ALS gene of the cell. The polynucleotide may, in certain embodiments, contain a single open reading frame encoding the acetolactate synthase protein, in which case the polynucleotide may be at least 70% identical to or may hybridize with SEQ ID NO:2. In other embodiments, the polynucleotide may comprise introns, in which case the polynucleotide may have a nucleotide sequence which is at least 70% identical to or may hybridize with SEQ ID NO:4. In other embodiments, the polynucleotide may be codon-optimized for expression of the acetolactate synthase protein in a particular host cell.

A vector comprising the polynucleotide is also provided. In addition to the to polynucleotide, the subject vector may contain an expression cassette for expression of a recombinant protein, e.g., an enzyme or therapeutic protein, in the cell.

A host cell comprising the subject polynucleotide is also provided. In certain embodiments, the host cell is resistant to an ALS inhibitor, e.g., a toxic sulphonylurea or imidazolinone compound. The host cell may be any cell that is sensitive to the ALS inhibitor in the absence of the polynucleotide. In certain embodiments, the host cell may be a plant cell, e.g., a corn, soybean or *Arabidopsis* cell, a fungal cell, e.g., a filamentous fungal cell such as a *Trichoderma* sp. or *Aspergillus* sp. cell or a bacterial cell, e.g. a *Bacillus* sp. In particular embodiments, the host cell is a filamentous fungal. The cell may be present in vitro, or in a multicellular organism (e.g., a plant). The polynucleotide may be present in a genome of the host cell, or may be present in a vector that autonomously replicates in the host cell.

Also provided is a method of selecting a cell. In certain embodiments, the method includes: introducing a subject polynucleotide which encodes an ALS into a plurality of cells, contacting the plurality of cells with an ALS inhibitor, and culturing the cells to provide for selection of the cell. In certain embodiments, the cell is a fungal cell. The cell may be cultured in a liquid medium containing the ALS inhibitor, or on a solid medium containing the ALS inhibitor. These methods may also include introducing a second polynucleotide into the host cell, where the second polynucleotide encodes a polypeptide that is to be produced by the host cell. The subject polynucleotide and the second polynucleotide may be present on the same or different nucleic acid, e.g., the same vector or different vectors. If different vectors are employed, they may be co-transformed into the same cells.

Also provided are embodiments relating to relating to the 1818A and 1818B promoters

BRIEF DESCRIPTION OF THE FIGURES

FIG. 1 shows the amino acid sequence of the wild type acetolactate synthase protein from *T. reesei* (SEQ ID NO:1).

FIG. 2 shows the nucleotide sequence of a *T. reesei* deduced cDNA (SEQ ID NO:2) encoding the wild type acetolactate protein of FIG. 1.

FIG. 3 shows the nucleotide sequence of a *T. reesei* gene (SEQ ID NO:3) encoding the wild type acetolactate synthase protein of FIG. 1, wherein the promoter is in italics, the sequence encoding ALS is underlined (SEQ ID NO:4), and the terminator sequence is in italics and underlined.

FIGS. 5A and 5B show the nucleotide sequence of the promoters 1818A (SEQ ID NO:7) and 1818B (SEQ ID NO:8), respectively.

FIG. 6 shows the nucleotide sequence (SEQ ID NO:9) of the pTrex-glucoamylase vector used to test the ALS marker which comprises the *Trichoderma reesei* cbh1 promoter, attB1, a polynucleotide encoding a *Trichoderma reesei* glucoamylase, attB2, the *Trichoderma reesei* cbh1 terminator and an ALS marker (A190D) in the *E. coli* vector pSL1180.

FIGS. 9A-9C show the nucleotide sequence of a construct used to test the 1818A and 1818B promoters (SEQ ID NO:10).

DETAILED DESCRIPTION

Definitions

Figure 4:
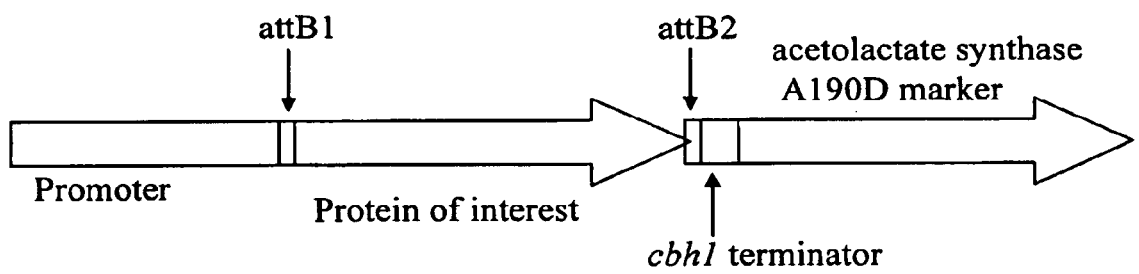
FIG. 4 is a general diagram of a vector that may be used to test the ALS marker, wherein the vector includes two genes. The first gene corresponds to a polynucleotide encoding a protein of interest (e.g. a glucoamylase enzyme) and the second gene corresponds to a polynucleotide coding for the ALS marker.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with general dictionaries of many of the terms used in this invention. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

As used herein, the term "selectable marker" refers to a gene or polynucleotide whose expression allows identification of cells that have been transformed with a DNA construct or vector containing the gene or polynucleotide. Selectable markers may provide resistance to toxic compounds such as antibiotics, herbicides, and the like.

The term "acetolactate synthase (ALS)" refers to an enzyme that has an activity defined as EC 2.2.1.6, according to IUBMB Enzyme Nomenclature. The enzyme catalyses a reaction between two pyruvate molecules to produce 2-acetolactate and $CO_2$. The enzyme requires thiamine diphosphate, and may be referred to as acetohydroxyacid synthase (AHAS) elsewhere.

The term "ALS inhibitor" refers to a compound that inhibits wild-type ALS protein and is toxic to cells that contain wild-type ALS. Such compounds include known herbicides, and include the sulfonylurea, imidazolinone, triazolopyrimidine, pyrimidinylthiobenzoate, or sulfonylamino-carbonyl-triazolinone compounds discussed below.

The term "promoter" is defined herein as a nucleic acid that directs transcription of a downstream polynucleotide in a cell. In certain cases, the polynucleotide may contain a coding sequence and the promoter may direct the transcription of the coding sequence into translatable RNA.

The term "isolated" as defined herein means a compound, a protein, cell, nucleic acid sequence or amino acid that is removed from at least one component with which it is naturally associated.

The term "coding sequence" is defined herein as a nucleic acid that, when placed under the control of appropriate control sequences including a promoter, is transcribed into mRNA which can be translated into a polypeptide. A coding sequence may contain a single open reading frame, or several open reading frames separated by introns, for example. A coding sequence may be cDNA, genomic DNA, synthetic DNA or recombinant DNA, for example. A coding sequence generally starts at a start codon (e.g., ATG) and ends at a stop codon (e.g., UAA, UAG and UGA).

The term "recombinant" refers to a polynucleotide or polypeptide that does not naturally occur in a host cell. A recombinant molecule may contain two or more naturally occurring sequences that are linked together in a way that does not occur naturally.

The term "heterologous" refers to elements that are not normally associated with each other. For example, a heterologous protein is a protein that is not produced in a wild-type host cell, a heterologous promoter is a promoter that is not present in nucleic acid that is endogenous to a wild type host cell, and a promoter operably linked to a heterologous coding sequence is a promoter that is operably linked to a coding sequence that it is not usually operably linked to in a wild-type host cell.

The term "operably linked" refers to an arrangement of elements that allow them to be functionally related. For example, a promoter is operably linked to a coding sequence if it controls the transcription of the sequence, and a signal sequence is operably linked to a protein if the signal sequence directs the protein through the secretion system of a host cell.

The term "nucleic acid" encompasses DNA, RNA, single or doubled stranded and modification thereof. The terms "nucleic acid" and "polynucleotide" may be used interchangeability herein.

The term "DNA construct" as used herein means a nucleic acid sequence that comprises at least two DNA polynucleotide fragments.

The term "signal sequence" or "signal peptide" refers to a sequence of amino acids at the N-terminal portion of a protein, which facilitates the secretion of the mature form of the protein outside the cell. The mature form of the extracellular protein lacks the signal sequence which is cleaved off during the secretion process.

The term "vector" is defined herein as a polynucleotide designed to carry nucleic acid sequences to be introduced into one or more cell types. Vectors include cloning vectors, expression vectors, shuttle vectors, plasmids, phage or virus particles, DNA constructs, cassettes and the like. Expression vectors may include regulatory sequences such as promoters, signal sequences, a coding sequences and transcription terminators.

An "expression vector" as used herein means a DNA construct comprising a coding sequence that is operably linked to suitable control sequences capable of effecting expression of a protein in a suitable host. Such control sequences may include a promoter to effect transcription, an optional operator sequence to control transcription, a sequence encoding suitable ribosome binding sites on the mRNA, enhancers and sequences which control termination of transcription and translation.

As used herein, the terms "polypeptide" and "protein" are used interchangeably and include reference to a polymer of any number of amino acid residues. The terms apply to amino acid polymers in which one or more amino acid residue is an artificial chemical analog of a corresponding naturally occurring amino acid, as well as to naturally occurring amino acid polymers. The terms also apply to polymers containing conservative amino acid substitutions such that the polypeptide remains functional. "Peptides" are polypeptides having less than 50 amino acid residues.

A "host cell" is a cell which that contains a subject recombinant nucleic acid, either in the genome of the host cell or in an extrachromosomal vector that replicates autonomously from the genome of the host cell. A host cell may be any cell type.

The term "filamentous fungi" refers to all filamentous forms of the subdivision Eumycotina (See, Alexopoulos, C. J. (1962), INTRODUCTORY MYCOLOGY, Wiley, New York). These fungi are characterized by a vegetative mycelium with a cell wall composed of chitin, glucans, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic.

A "non-pathogenic" cell is a strain that is not pathogenic to humans.

"Transformation" means introducing DNA into a cell so that the DNA is maintained in the cell either as an extrachromosomal element or chromosomal integrant.

Unless otherwise indicated, all amino acid positions in an acetolactate synthase protein are relative to SEQ ID NO:1, after alignment of that protein with SEQ ID NO:1 using the BLASTP program (Altschul, Nucl. Acids Res. 1997 25:3389-3402; Schäffer, Bioinformatics 1999 15:1000-1011) under default conditions, as available from the world wide website of the so National Center of Biotechnology Information (NCBI).

Polynucleotides

Provided herein is a polynucleotide that encodes an acetolactate synthase protein that provides resistance to ALS inhibitors. In certain embodiments, the acetolactate synthase protein is a non-naturally occurring protein. In general terms, the polynucleotide encodes a protein that: a) possesses acetolactate synthase activity (i.e., can catalyze a reaction between two pyruvate molecules to produce 2-acetolactate), b) confers resistance to ALS inhibitors, e.g., sulphonylurea and imidazolinone compounds, and c) has an amino acid sequence that is at least 85% identical (e.g., at least 90% identical, at least 93% identical, at least 95% identical, at least 96% identical, at least 97% identical, at least 98% identical, at least 98.5% identical, at least 99% identical or at least 99.5% identical) to SEQ ID NO:1, where SEQ ID NO:1 sets forth the amino acid sequence of a wild-type acetolactate synthase from *Trichoderma reesei*.

In certain embodiments, the polynucleotide may encode a protein having one or more of: a) an acidic amino acid (e.g., Asp or Glu) at position 190, b) an acidic amino acid (e.g., Asp or Glu) at position 241, or a His at position 372. Positions 190, 241 and 372 in the wild-type *T. reesei* ALS protein are underlined in FIG. 1. As noted above, positions 190, 241 and 372 in a different ALS protein (e.g., an ALS protein that is, for example, shorter, longer or contains deletions and/or insertions relative to the wild-type *T. reesei* ALS protein), are defined herein as being the positions in that protein that correspond to (i.e., align with or lie across from) positions 190, 241 and 372 of the wild-type *T. reesei* ALS protein when the wild-type *T. reesei* ALS protein and the other protein are aligned using standard sequence alignment methods, e.g., BLASTP (Altschul, Nucl. Acids Res. 1997 25:3389-3402; Schäffer, Bioinformatics 1999 15:1000-1011) using default parameters. ALS proteins, in general, are well characterized enzymes and have been investigated in great detail functionally and structurally. ALS proteins have been reviewed in several publications (see, e.g., Chipman, Biochim. Biophys. Acta 1998 1385:401-19; Chipman, Curr. Opin. Chem. Biol. 2005 9:475-81), and have been crystallized (see, e.g., Pang, J. Biol. Chem. 2004 279:2242-53; Pang, J. Mol. Biol. 2002 317:249-62), as well as subjected to mutagenesis to identify essential and non-essential residues (see, e.g., Ibdah, Biochemistry 1996 35:16282-91; Mendel J. Mol. Biol. 2001 307:465-771; Hill, Biochem. J. 1998 335:653-61). Other herbicide resistance-conferring mutations are also known (see, e.g., Jung, Biochem. J. 2004 383:53-61; Duggelby, Eur. J. Biochem. 2003 270:2895-904). Further, the amino acid sequences of several hundred ALS proteins are known, and publicly available via NCBI's Genbank database. As such, a wide variety of amino acid changes that could be made to a subject ALS protein, some of which may confer resistance to ALS inhibitors, without abolishing its activity would be readily apparent.

In certain cases, the amino acid changes described herein may be transferred into any other ALS protein, from any species, to render that protein herbicide resistant. In other words, an amino acid at position 190, 241 or 372 (relative to SEQ ID NO:1) of any other ALS protein may be substituted by an acidic amino acid (e.g., Asp or Glu), an acidic amino acid (e.g., Asp or Glu), or a His, respectively, to provide an ALS protein that confers resistant to an ALS inhibitor.

For example, the amino acid sequence of the ALS proteins of several fungal species are known and are deposited into NCBI's Genbank database. In certain embodiments, the above-described amino acid alterations can be transferred to the ALS proteins of those fungi in order to provide other ALS inhibitor-resistant proteins. In other embodiments, the amino acid sequence other fungal ALS proteins may be employed to make further changes in the subject *T. reesei*-based ALS proteins that do not abolish the ALS activity of those proteins. For example, a fusion between two ALS proteins from different species, or a protein containing amino acid substitutions, deletions or insertions could be made. Exemplary ALS amino acid sequences from other fungal species, including other filamentous fungal species, are deposited at NCBI's Genbank database as GIDS: 39977967 and 2547090 (*Magnaporthe grisea*), GID: 85108881 (*Neurospora crassa*), GID: 46108408 (*Gibberella zeae*), GID: 90302929 (*Coccidioides immitis*) GID: 67537572 (*Aspergillus nidulans*); GID: 70999742 (*Aspergillus fumigatus*); GIDs: 83767597 and 83771596 (*Aspergillus oryzae*); GID: 111063308 (*Phaeosphaeria nodorum*), GID: 50547615 (*Yarrowia lipolytica*), GID: 49657303 (*Debaryomyces hansenii*), GID: 68468265 (*Candida albicans*), GID: 21615550 (*Saccharomycopsis fibuligera*), GID: 49641223 (*Kluyveromyces lactis*); GID: 49527687 (*Candida glabrata*) and GID: 817866 (*Saccharomyces cerevisiae*). The above-referenced Genbank accessions are incorporated by reference in their entirety, including the nucleic acid and protein sequences therein, and the annotation of those sequences, as of the earliest filing date of this patent application.

Because of the redundancy of the genetic code, a subject polynucleotide may comprise any one of a number of nucleotide sequences. In particular embodiments, the subject polynucleotide may have a nucleotide sequence that is: a) at least 70% identical to (e.g., at least 80%, at least 90%, at least 95%, at least 98% or at least 99% identical to), or b) hybridizes with under stringent hybridization conditions to SEQ ID NO:2 or SEQ ID NO:4, which sequences set forth the nucleotide sequence of a wild-type cDNA and gene of *T. reesei*, respectively. As such, the encoding polypeptide may contain introns, or may contain a single open reading frame encoding the protein.

As would be apparent, in certain embodiments, the polynucleotide may have a nucleotide sequence that encodes a protein having one or more of: a) an acidic amino acid (e.g., Asp or Glu) at position 190, b) an acidic amino acid (e.g., Asp or Glu) at position 241, or a His at position 372.

The term "identity" in the context of two nucleic acid sequences refers to nucleotides residues in the two sequences that are the same when aligned for maximum correspondence, as measured using any of the following sequence comparison algorithms. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

An example of an algorithm that is suitable for determining sequence similarity is the BLAST algorithm, which is described in Altschul, et al., *J. Mol. Biol.* 215:403-410 (1990). Software for performing BLAST analyses is publicly available through the National Center for Biotechnology Information available on the world wide web (www) ncbi.nlm.nih.gov. The BLAST algorithm performs a statistical analysis of the similarity between two sequences (see, e.g., Karlin & Altschul, *Proc. Nat'l. Acad. Sci. USA* 90:5873-5787 (1993)). A nucleotide sequence of at least 100, at least 500, at least 1000, up to entire length of the SEQ ID NOS:2 or 4 may be employed in sequence comparisons.

As noted above, the polynucleotide may include a nucleotide sequence that hybridizes under stringent hybridization conditions to a polynucleotide having the nucleotide sequence of SEQ ID NO: 2 or 4, where stringent hybridization conditions encompass low, medium, high and very high stringency hybridization conditions.

"Low-stringency" conditions refer to washing with a solution of 1×SSC/0.1% SDS at 20° C. for 15 minutes. "Medium-stringency" conditions refer to washing with a solution of 1×SSC/0.1% SDS at 65° C. for 60 minutes. "High-stringency" conditions refer to washing with a solution of 0.2× SSC/0.1% SDS at 65° C. for 10 minutes. "Very high-stringency" conditions refer to washing with a solution of 0.2× SSC/0.1% SDS at 65° C. for 60 minutes.

Hybridization methods are described in great detail in Sambrook et al., MOLECULAR CLONING: A LABORATORY MANUAL ($2^{nd}$ Ed., 1989 Cold Spring Harbor, N.Y.). In one exemplary hybridization assay, a DNA sample is electrophoresed through an agarose gel (for example, 0.8% agarose) so that of the DNA fragment can be visualized by ethidium bromide staining. The gel is then briefly rinsed in distilled $H_2O$ and subsequently depurinated in an appropriate solution (such as, for example, 0.25M HCl) with gentle shaking followed by denaturation for 30 minutes (in, for example, 0.4 M NaOH) with gentle shaking. A renaturation step may be included, in which the gel is placed in 1.5 M NaCl, 1M Tris, pH 7.0 with gentle shaking for 30 minutes. The DNA is then transferred onto an appropriate positively charged membrane, for example, Maximum Strength Nytran Plus membrane (Schleicher & Schuell, Keene, N.H.), using a transfer solution (such as, for example, 6×SSC, i.e., 900 mM NaCl, 90 mM trisodium citrate). Once the transfer is complete, generally after about 2 hours, the membrane is rinsed in e.g., 2×SSC (300 mM NaCl, 30 mM trisodium citrate) and air dried at room temperature. The membrane may be prehybridized (for approximately 2 hours or more) in a suitable prehybridization solution (such as, for example, an aqueous solution containing per 100 mL: 20-50 mL formamide, 25 mL of 20×SSPE (1×SSPE=0.18 M NaCl, 1 mM EDTA, 10 mM $NaH_2PO_4$, pH 7.7), 2.5 mL of 20% SDS, and 1 mL of 10 mg/mL sheared herring sperm DNA). As would be known to one of skill in the art, the amount of formamide in the prehybridization solution may be varied depending on the nature of the reaction obtained according to routine methods. Thus, a lower amount of formamide may result in more complete hybridization in terms of identifying hybridizing molecules than the same procedure using a larger amount of formamide. On the other hand, a strong hybridization band may be more easily visually identified by using more formamide.

A DNA probe of at least 100, at least 500, at least 1000, up to entire length of the SEQ ID NOS:2 or 4 may be employed in hybridization assays or in sequence comparisons. The DNA probe may be isolated by electrophoresis in an agarose gel, the fragment excised from the gel, and recovered from the excised agarose. This purified fragment of DNA may be labeled (using, for example, the Megaprime labeling system according to the instructions of the manufacturer) to incorporate $P^{32}$ in the DNA. The labeled probe is denatured by heating to 95° C. for 5 minutes and immediately added to the membrane and prehybridization solution. The hybridization reaction should proceed for an appropriate time and under appropriate conditions, for example, for 18 hours at 37° C. with gentle shaking or rotating. The membrane is rinsed (for example, in 2×SSC/0.3% SDS) and then washed in an appropriate wash solution, as described above, with gentle agitation. Hybridization can be detected by autoradiography.

In particular embodiments, the polynucleotide may be codon optimized for expression in particular host cell. In other embodiments, the polynucleotide may have a nucleotide sequence that contains less than 10 (e.g., 9, 8, 7, 6, 5, 4, 3, 2, or 1) differences compared to the wild type ALS sequence (e.g., either the genomic or cDNA sequence) of the particular host cell in which it the polynucleotide is to be employed.

In certain cases, in addition to a coding sequence, the polynucleotide may further contain other elements that are necessary for expression of the encoded protein in a host cell. For example, in one embodiment, the polynucleotide may be flanked by sequences to form an expression cassette that provides expression of the encoded protein in a host cell. In certain embodiments, the expression cassette may contain a promoter for transcription of the coding sequence, and a transcriptional terminator, and a sequence encoding a 5' untranslated region (UTR) that allows translational initiation, each in operable linkage to the coding sequence. Promoters, enhancers, terminators, UTRs, polyadenylation signals and other regulatory sequences for a wide variety of host cells, particularly those from plants, bacteria and fungi, are well known in the art (see, e.g., Ausubel, et al, Short Protocols in Molecular Biology, 3rd ed., Wiley & Sons, 1995; Sambrook, et al., Molecular Cloning: A Laboratory Manual, Second Edition, 1989 Cold Spring Harbor, N.Y.).

In particular embodiments, the subject expression cassette may contain a promoter and terminator for expression of the subject protein in a filamentous fungal cell. Examples of suitable promoters and terminators for directing the transcription of a subject nucleic acid in a filamentous fungal host cell are promoters and terminators obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase, *Fusarium oxysporum* trypsin-like protease (WO 96/00787), *Trichoderma reesei* cellobiohydrolase I, *Tricho-*

*derma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

The promoter and/or terminator may be native or non-endogenous to the host cell in which the subject ALS protein is to be expressed and, in certain embodiments, the promoter and terminator may be the ALS gene promoter and terminator from the host cell. For example, in one embodiment, an expression cassette for use in *Trichoderma reesei* cells may comprise the *Trichoderma reesei* ALS gene promoter, the *Trichoderma reesei* ALS coding sequence (containing one or more of the nucleotide changes outlined above) and *Trichoderma reesei* ALS terminator, in operable linkage (FIG. 3). The promoter and/or terminator may be from an ALS gene of the host cell in which the polynucleotide is to be employed.

The polynucleotide may be integrated into a genome of the host cell, or may be present on a vector that autonomously replicates in the host cell.

Recombinant Nucleic Acid

A recombinant nucleic acid comprising a subject polynucleotide is also provided. A subject recombinant nucleic acid may comprise a subject polynucleotide, e.g., an expression cassette for production of a resistance-conferring ALS protein in a host cell, as well as a second expression cassette for expression of a protein of interest in the host cell. In a particular embodiment, the subject polynucleotide is employed as a marker for selection of host cells that contain the recombinant nucleic acid over other cells that do not contain the recombinant nucleic acid (i.e., the subject polynucleotide is employed as a "selectable marker" for cells that contain the subject polynucleotide).

The protein of interest encoded by the second expression cassette may be for example an enzyme, a therapeutic protein, a reporter protein, a food additive or a foodstuff or the like.

In one embodiment, the protein of interest encoded by the second expression cassette may be an enzyme such as a carbohydrase, such as an α-amylase, an alkaline α-amylase, a β-amylase, a cellulase; a dextranase, an α-glucosidase, an α-galactosidase, a glucoamylase, a hemicellulase, a pentosanase, a xylanase, an invertase, a lactase, a naringanase, a pectinase or a pullulanase; a protease such as an acid protease, an alkali protease, bromelain, ficin, a neutral protease, papain, pepsin, a peptidase, rennet, rennin, chymosin, subtilisin, thermolysin, an aspartic proteinase, or trypsin; a lipase or esterase, such as a triglyceridase, a phospholipase, a pregastric esterase, a phosphatase, a phytase, an amidase, an iminoacylase, a glutaminase, a lysozyme, or a penicillin acylase; an isomerase such as glucose isomerase; an oxidoreductases, e.g., an amino acid oxidase, a catalase, a chloroperoxidase, a glucose oxidase, a hydroxysteroid dehydrogenase or a peroxidase; a lyase such as a acetolactate decarboxylase, an aspartic β-decarboxylase, a fumarese or a histadase; a transferase such as cyclodextrin glycosyltranferase; or a ligase, for example. In particular embodiments, the protein may be an aminopeptidase, a carboxypeptidase, a chitinase, a cutinase, a deoxyribonuclease, an α-galactosidase, a β-galactosidase, a β-glucosidase, a laccase, a mannosidase, a mutanase, a pectinolytic enzyme, a polyphenoloxidase, ribonuclease or transglutaminase, for example. The enzyme may be a wild-type enzyme or a variant of a wild-type enzyme. In addition the enzyme may be a hybrid enzyme that includes fragments of different enzymes.

In other embodiment, the protein of interest encoded by the second expression cassette may be a therapeutic protein (i.e., a protein having a therapeutic biological activity). Examples of suitable therapeutic proteins include: erythropoietin, cytokines such as interferon-α, interferon-β, interferon-γ, interferon-o, and granulocyte-CSF, GM-CSF, coagulation factors such as factor VIII, factor IX, and human protein C, antithrombin III, thrombin, soluble IgE receptor α-chain, IgG, IgG fragments, IgG fusions, IgM, IgA, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon like protein 1 and IL-2 receptor agonist. Antibody proteins, e.g., monoclonal antibodies that may be humanized, are of particular interest.

In a further embodiment, the protein encoded by the second expression cassette may be a reporter protein. Such reporter proteins may be optically detectable or colorigenic, for example. In this embodiment, the protein may be a β-galactosidase (lacZ), β-glucuronidase (GUS), luciferase, alkaline phosphatase, nopaline synthase (NOS), chloramphenicol acetyltransferase (CAT), horseradish peroxidase (HRP) or a fluorescent protein green, e.g., green fluorescent protein (GFP), or a derivative thereof.

In certain embodiments, particularly those in which the host cell is a filamentous fungal host cell, the coding sequence of the second expression cassette may encode a fusion protein. In some of these embodiments, the fusion protein may provide for secretion of the protein from the host cell in which it is expressed and, as such, may contain a signal sequence operably linked to the N-terminus of the protein, where the signal sequence contains a sequence of amino acids that directs the protein to the secretory system of the host cell, resulting in secretion of the protein from the host cell into the medium in which the host cell is growing. The signal sequence is cleaved from the fusion protein prior to secretion of the protein. The signal sequence employed may be endogenous or non-endogenous to the host cell and, in certain embodiments, may be signal sequence of a protein that is known to be highly secreted from a host cell. In particular embodiments, the signal sequence protein may be any signal sequence that facilitates protein secretion from a filamentous fungal (e.g., *Trichoderma* or *Aspergillus*) host cell. Such signal sequence include, but are not limited to: the signal sequence of cellobiohydrolase I, cellobiohydrolase II, endoglucanases I, endoglucanases II, endoglucanases III, α-amylase, aspartyl proteases, glucoamylase, mannanase, glycosidase and barley endopeptidase B (see Saarelainen, Appl. Environ. Microbiol. 1997 63: 4938-4940), for example. Other of signal sequences are those originating from the fungal amyloglucosidase (AG) gene (glaA), the α factor gene (yeasts e.g. *Saccharomyces, Kluyveromyces* and *Hansenula*) or the α amylase gene (*Bacillus*). In certain embodiments, therefore, the subject recombinant nucleic acid may comprise: a signal sequence-encoding nucleic acid operably linked to a protein-encoding nucleic acid, where translation of the nucleic acid in a host cell produces a fusion protein comprising a protein having an N-terminal signal sequence for secretion of the protein from the host cell.

In particular embodiments, the fusion protein may further contain a "carrier protein", which is a portion of a protein that is endogenous to and highly secreted by the host cell. Suitable carrier proteins include those of *T. reesei* mannanase I (Man5A, or MANI), *T. reesei* cellobiohydrolase II (Cel6A, or CBHII) (see, e.g., Paloheimo et al Appl. Environ. Microbiol. 2003 December; 69(12): 7073-7082) or *T. reesei* cellobiohydrolase I (CBHI). In one embodiment, the carrier protein is a truncated *T. reesei* CBH1 protein that includes the CBH1 core region and part of the CBH1 linker region. A fusion protein containing, from amino-terminus to carboxy-terminus, a signal sequence, a carrier protein and a subject protein in operable linkage is therefore provided, as well as a nucleic acid encoding the same.

In certain embodiments, the polynucleotide may be codon optimized for expression of the protein in a particular host cell. Since codon usage tables listing the usage of each codon in many cells are known in the art (see, e.g., Nakamura et al, Nucl. Acids Res. 2000 28: 292) or readily derivable, such nucleic acids can be readily designed giving the amino acid sequence of a protein to be expressed.

A subject recombinant nucleic acid may be present, e.g., integrated, into a genome (i.e., the nuclear genome) of a host cell, or may be present in a vector, e.g., a phage, plasmid, viral, or retroviral vector, that autonomously replicates in the host cell. In certain embodiments, the vector may be an expression vector for expressing a protein in a host cell and, as such, may further contain the second expression cassette discussed above. In certain embodiments, the vector may be an expression vector for expressing a recombinant polypeptide in a filamentous fungal cell.

Vectors for expression of recombinant proteins are well known in the art (Ausubel, et al, Short Protocols in Molecular Biology, 3rd ed., Wiley & Sons, 1995; Sambrook, et al., Molecular Cloning: A Laboratory Manual, Second Edition, (1989) Cold Spring Harbor, N.Y.).

Selection Methods

A method for selecting host cells that contain a subject polynucleotide is also provided. In certain embodiments, the method includes introducing a subject polynucleotide into a plurality of cells, contacting the plurality of cells with an ALS inhibitor, e.g., a toxic sulphonylurea or imidazolinone compound, and culturing the cells to provide for selection of the cell. The cell may be selected on solid medium, e.g., by plating the plurality of cells onto an agar plate containing the ALS inhibitor, or in liquid medium, e.g., by culturing the plurality of in a liquid medium containing the ALS inhibitor.

In certain embodiments, the subject selection methods may be employed to select for cells containing a second expression cassette that encodes a protein of interest. The second expression cassette may be present in a recombinant nucleic acid that also contains the instant ALS protein-encoding polynucleotide (i.e., in a single recombinant nucleic acid molecule). In these embodiments, the instant selection methods may be employed to select for cells that contain the recombinant nucleic acid. Since the recombinant nucleic acid also contains the second expression cassette, cells that contain the second expression cassette are selected using the ALS inhibitor. In alternative embodiments, the second expression cassette may be present on a recombinant nucleic acid that does not contain the instant ALS protein-encoding polynucleotide (e.g., a different vector). In these embodiments, a subject polynucleotide may be co-transformed with (i.e., transformed at the same time as) a separate and distinct polynucleotide molecule (e.g., a different nucleic acid molecule or vector) that contains the expression cassette. As such, the instant selection methods may be employed to select for cells that contain the second expression cassette, even though the second expression cassette is on a different nucleic acid molecule to the polynucleotide.

As such, the subject selection methods may be employed to select for host cells that express the protein of interest. The protein of interest may be native or non-native to the host cells used.

The exact concentration of ALS inhibitor employed may vary according to the particular ALS inhibitor used and the type of host cell to be selected. In general terms, the ALS inhibitor is used at a concentration that provides selection of the host cell containing the polynucleotide. In certain embodiments, the ALS inhibitor may be employed at a concentration of 0.5 ppm to 10,000 ppm, for example 1 ppm to 10,000 ppm or 10 ppm to 1,000 ppm. For example, in certain cases, the ALS inhibitor may be employed at a concentration in the range of 25 ppm to 100 ppm, e.g., 50 ppm or 100 ppm, or at a concentration in the range of 100 ppm to 500 ppm, e.g., 200 ppm or 500 ppm. For example, in one embodiment, the ALS inhibitor may be employed at a concentration in the range of 1 µg/ml to 1 mg/ml, e.g., 10 µg/ml to 500 µg/ml.

ALS inhibitors include any compounds that: a) kill cells that do not have resistance to the compounds via inhibiting an ALS enzyme and b) do not kill cells having a subject polynucleotide. ALS inhibitors of particular interest include sulfonylurea (SU), imidazolinone (IMI), triazolopyrimidine (TP), pyrimidinylthiobenzoate (PTB), and sulfonylaminocarbonyl-triazolinone (SCT) compounds that are known ALS inhibitors and, in certain cases, may be commonly employed has herbicides. Examples of sulfonylurea compounds that may be employed in the subject methods include: I) phenylsulfonylureas, including a) chlorimuron ethyl (see Agricultural Chemicals Book II "Herbicides" by W. T. Thompson, Thompson Publications, Fresno Calif., U.S.A. 1990, page 152); b) primisulfuron (CGA 136,872, see Brighton Crop Prot. Conf. "Weeds" 1989, p. 41-48), c) 3-(4-ethyl-6-methoxy-1,3,5-triazin-2-yl)-1-(2,3-dihydro-1,1-dioxo-2-methyl benzo[b]thiophen-7-sulfonyl)-urea (see, e.g., EP-A-79,683), d) 3-(4-ethoxy-6-ethyl-1,3,5-triazin-2-yl)-1-(2,3-dihydro-1, 1-dioxo-2-methylbenzo[b]thiophen-7-sulfonyl)urea (see, e.g., EP-A-79,683), e) tribenuron-methyl (see "The Pesticide Manual", British Crop Protection Council 9th Edition (1990/91), page 840), f) metsulfuron-methyl (see Proc. Int. Congr. Plant Prot., 10th, 1983, Vol. 1, 324), g) chlorsulfuron (see U.S. Pat. No. 4,127,405; Weeds Weed Control, 1980, 21st, 24), h) triasulfuron (see "The Pesticide Manual" 9th Ed., p. 837) and i) sulfometuron-methyl (see "The Pesticide Manual" 9th Ed., p. 774); II) thienylsulfonylureas, for example thifensulfuron-methyl (see Agricultural Chemicals Book II "Herbicides" by W. T. Thompson, Thompson Publications, Fresno Calif., U.S.A. 1990, page 155); III) pyrazolylsulfonylureas, for example: a) pyrazosulfuron-ethyl (NC 311, see "The Pesticide Manual" 9th Ed., p. 735) and b) methyl 3-chloro-5-(4,6-dimethoxypyrimidin-2-ylcarbamoylsulfamoyl)-1-methyl-pyrazole-4-carboxylate (see EP 282,613); IV) Sulfonediamide derivatives, for example amidosulfuron and structural analogs (see EP-A-0,131,258 and Z. Pfl.Krankh. Pfl.Schutz, Special Issue XII, 489-497 (1990); V) pyridylsulfonylureas, for example: a) nicosulfuron (SL-950, see Kimura et al., Brighton Crop Protection Conference "Weeds" 1989, p. 29-34); b) DPX-E 9636 (see Brighton Crop Prot. Conf.—Weeds—1989, p. 23 et seq.) and c) pyridylsulfonylureas as are described in German Patent Applications P 4000503.8 (WO-91/10660) and P 4030577.5 and VI) Phenoxysulfonylureas such as those described in, for example, EP-A-0,342,569, EP-A-4,163, EP-A-113,956, U.S. Pat. No. 4,678,500 and U.S. Pat. No. 4,581,059. Examples of imidazolinone compounds that may be employed in the subject methods include: a) imazethapyr (see Ch. R. Worthing's "The Pesticide Manual" 8th Edition 1987, by British Crop Protection Council, page 473), b) imazaquin (see Ch. R. Worthing's "The Pesticide Manual" 8th Edition 1987, by British Crop Protection Council, page 474), and c) imazethamethapyr (chemical name: rac-2-[4,5-dihydro4-methyl-4-(1-methylethyl)-5-oxo-1H-imidazol-2-yl]-5-met hyl-3-pyridine-carboxylic acid; see Weed Techn. 1991 (5), 430-433 and 434-438) and other related compounds.

Host Cells

A host cell comprising a subject recombinant nucleic acid is also provided. The host cell may be any cell type, e.g., bacterial (such as *E. coli, Bacillus* sp. or *Streptomyces* sp.), fungal (such as a non-filamentous or filamentous fungal), or plant (such as an *Arabidopsis*, corn or soybean plant) host cells. In some embodiments, the host cell may be a cell of a species that has a history of use for production of proteins that has GRAS status, i.e., a Generally Recognized as Safe, by the FDA.

In particular embodiments, the subject host cell may be a fungal cell of the following species: *Trichoderma*, (e.g., *Trichoderma reesei* (previously classified as *T. longibrachiatum* and currently also known as *Hypocrea jecorina*), *Trichoderma viride*, *Trichoderma koningii*, and *Trichoderma harzianum*)); *Penicillium* sp., *Humicola* sp. (e.g., *Humicola insolens* and *Humicola grisea*); *Chrysosporium* sp. (e.g., *C. lucknowense*), *Gliocladium* sp., *Aspergillus* sp. (e.g., *Aspergillus oryzae, Aspergillus niger, Aspergillus nidulans, Aspergillus kawachi, Aspergillus aculeatus, Aspergillus japonicus, Aspergillus sojae*, and *Aspergillus awamori*), *Fusarium* sp., *Mucor* sp., *Neurospora* sp., *Hypocrea* sp., or *Emericella* sp. (See also, Innis et al., (1985) Sci. 228:21-26), among others.

Exemplary bacterial host cells include *Bacillus* sp., including, but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*, and *Streptomyces* sp., including, but not limited to: *S. lividans, S. carbophilus* and *S. helvaticus*.

Exemplary plant host cells include monocot and dicot plant cells, including, but not limited to corn (*Zea mays*), *Brassica* sp., rice (*Oryza sativa*), wheat (*Triticum aestivum*), soybean (*Glycine max*), tobacco (*Nicotiana tabacum*) and *Arabidopsis thaliana* and tomato (*Lycopersicon esculentum*) host cells. A host cell may be a host cell cultured in vitro, or a host cell of a multicellular organism, i.e., a plant. Methods of transferring exogenous nucleic acids into such host cells are well known in the art.

In particular embodiments, a subject fungal cell may be a strain of *Trichoderma* and particularly *T. reesei* which include functional equivalents of RL-P37 (Sheir-Neiss et al. (1984) Appl. Microbiol. Biotechnology 20:46-53). Other useful host strains include; NRRL 15709, ATCC 13631, ATCC 26921 (QM 9414) ATCC 32098, ATCC 32086, and ATCC 56765 (RUT-30). In other embodiments, subject fungal host cell may be of a strain of *Aspergillus* sp., including ATCC 22342, ATCC 44733, ATCC 14331, ATCC 11490, NRRL 3112, and strains derived therefrom.

In some embodiments, a host cell may be one wherein native genes have been deleted or inactivated. For example genes corresponding to protease genes (e.g. aspartyl protease) (Berka et al. (1990) Gene 86:153-162 and U.S. Pat. No. 6,509,171) or genes corresponding to cellulase genes may be deleted or inactivated, (e.g. cbh1, cbh2 and egl1, and egl2) such as the quad deleted strain of *T. reesei* disclosed in WO 05/001036 and derivatives thereof.

Introduction of a nucleic acid into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion. General transformation techniques are known in the art (See, e.g., Ausubel et al., (1987), supra, chapter 9; and Sambrook (1989) supra, and Campbell et al., (1989) Curr. Genet. 16:53-56). Reference is also made to WO 05/001036; U.S. Pat. No. 6,022,725; U.S. Pat. No. 6,103,490; U.S. Pat. No. 6,268,328; and published U.S. patent applications 20060041113, 20060040353, 20060040353 and 20050208623, which publications are incorporated herein by reference.

Transformation and protein expression in *Aspergillus* and *Trichoderma* is further described in, for example U.S. Pat. No. 5,364,770; U.S. Pat. No. 6,022,725; and Nevalainen et al., 1992, The Molecular Biology of *Trichoderma* and its Application to the Expression of Both Homologous and Heterologous Genes, in MOLECULAR INDUSTRIAL MYCOLOGY, Eds. Leon and Berka, Marcel Dekker, Inc. pp. 129-148.

As noted above, a subject host cell may further contain a recombinant nucleic acid for expression of a protein of interest in the host cell, in addition to the ALS-encoding nucleic acid. The subject recombinant nucleic acid and the ALS-encoding nucleic acid may be closely linked in cis, either in the genome or in a plasmid, such that the ALS inhibitor selects for the recombinant nucleic, and thereby selects for cells that produce the protein.

Protein Production

Methods of using the above-described host cell are also provided. In certain embodiments, the subject methods include: culturing the cell comprising a recombinant nucleic acid comprising a first expression cassette for producing a subject ALS enzyme, and a second expression cassette for producing a protein, to produce the protein. In certain embodiments and as discussed above, the protein may be secreted into the culture medium. As such, certain embodiments of the method include the step of recovering the protein from the culture medium.

Cells may cultured in a standard medium containing physiological salts and nutrients (See, e.g., Pourquie, J. et al., BIOCHEMISTRY AND GENETICS OF CELLULOSE DEGRADATION, eds. Aubert, J. P. et al., Academic Press, pp. 71-86, 1988 and Ilmen, M. et al., (1997) *Appl. Environ. Microbiol.* 63:1298-1306). Common commercially prepared media (e.g., Yeast Malt Extract (YM) broth, Luria Bertani (LB) broth and Sabouraud Dextrose (SD) broth also find use in the present invention. Preferred culture conditions for a given filamentous fungus are known in the art and may be found in the scientific literature and/or from the source of the fungi such as the American Type Culture Collection (ATCC) and Fungal Genetics Stock Center.

In some embodiments, a subject host cell may be cultured under batch or continuous fermentation conditions. A classical batch fermentation is a closed system, wherein the composition of the medium is set at the beginning of the fermentation and is not subject to artificial alterations during the fermentation. Thus, at the beginning of the fermentation the medium is inoculated with the desired organism(s). In this method, fermentation is permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase and finally to a stationary phase where growth rate is diminished or halted. If untreated, cells in the stationary phase eventually die. In general, cells in log phase are responsible for the bulk of production of end product.

A variation on the standard batch system is the "fed-batch fermentation" system, which also finds use with the present invention. In this variation of a typical batch system, the substrate is added in increments as the fermentation progresses. Fed-batch systems are useful when catabolite repression is apt to inhibit the metabolism of the cells and where it is desirable to have limited amounts of substrate in the medium. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and known in the art.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source or nitrogen source is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are known.

A fungal host cell may be cultured in a standard medium containing physiological salts and nutrients (See, e.g., Pourquie, J. et al., BIOCHEMISTRY AND GENETICS OF CELLULOSE DEGRADATION, eds. Aubert, J. P. et al., Academic Press, pp. 71-86, 1988 and Ilmen, M. et al., (1997) Appl. Environ. Microbiol. 63:1298-1306). Common commercially prepared media (e.g., Yeast Malt Extract (YM) broth, Luria Bertani (LB) broth and Sabouraud Dextrose (SD) broth also find use in the present methods. Preferred culture conditions for fungal host cells are known in the art and may be found in the scientific literature and/or from the source of the fungi such as the American Type Culture Collection (ATCC) and Fungal Genetics Stock Center.

Protein may be recovered from growth media by any convenient method, e.g., by precipitation, centrifugation, affinity, filtration or any other method known in the art. In another embodiment, a culture of cells is provided, where the culture of cells comprises: a) growth medium and b) the above-described host cell.

1818A and 1818B Promoters

A promoter that may be used to express a protein in a host cell is also provided. In one embodiment, the promoter comprises the nucleotide sequence of SEQ ID NOS:7 or 8 (shown in FIGS. 5A and 5B, respectively), or a subsequence or functional equivalent thereof that has promoter activity in a host cell. Also provided are recombinant nucleic acids and vectors containing the promoter and host cells containing a recombinant nucleic acid or vector. Methods of producing a protein using the host cells are also provided.

In certain embodiments, the promoter may comprise the nucleotide sequence of: a) SEQ ID NO: 7 or 8; b) a subsequence of SEQ ID NO: 7 or 8 that retains promoter activity; c) a functionally equivalent sequence of SEQ ID NO: 7 or 8 that retains promoter activity or d) a nucleic acid sequence that hybridizes under stringent hybridization conditions with SEQ ID NO: 7 or 8, or the subsequence thereof. In particular embodiments, the nucleotide sequence may be at least 80% identical to the nucleotide sequence of SEQ ID NO: 7 or 8.

In particular embodiments, a subsequence of a subject promoter may contain at least about 100 nucleotides, at least about 200 nucleotides; at least about 250 nucleotides; at least about 300 nucleotides; at least about 350 nucleotides; at least about 400 nucleotides; at least about 450 nucleotides; least about 500 nucleotides; least about 550 nucleotides; least about 600 nucleotides; at least about 650 nucleotides; at least about 700 nucleotides; at least about 800 nucleotides; at least about 850 nucleotides that are contiguous in SEQ ID NO: 7 or 8, the entire contiguous sequence of SEQ ID NO: 7 or 8, or a functional equivalent thereof that retains promoter activity.

In certain embodiments, a functional equivalent promoter may include one or more changes (e.g., 1, 2, 3, 4, 5, 6, 7, 8, 9, more than 10, up to 20 or 30 or more changes) relative to the nucleotide sequence of SEQ ID NO: 7 or 8, where a change can be a deletion, substitution or insertion, for example. In one exemplary embodiment, the nucleotide sequence of the functional equivalent promoter may include one to five nucleotide differences relative to the nucleotide sequence of the parent promoter such as SEQ ID NO: 7 or 8.

In other embodiments, the promoter may include a nucleotide sequence that hybridizes under stringent hybridization conditions to a polynucleotide having the nucleotide sequence of SEQ ID NO: 7 or 8, where stringent hybridization conditions encompass low, medium, high and very high stringency hybridization conditions, where such conditions are described above.

In another embodiment, a subject promoter may contain a contiguous nucleotide sequence that is at least 80%, at least 85%, at least 90%, at least 95%, at least 96%, at least 97%, at least 98% or at least 99% identical to SEQ ID NO: 7 or 8, or a subsequence thereof. In one embodiment, the subject promoter may contain a contiguous nucleotide sequence that is at least 95% identical to SEQ ID NO: 7 or 8.

As noted in the Examples section below, the nucleic acid of SEQ ID NOS: 7 and 8 were obtained from *Trichoderma reesei*, a filamentous fungi. As would be readily apparent, functional equivalents of SEQ ID NO: 7 and 8 that retain promoter activity can be identified by identifying sequences that are similar to SEQ ID NO: 7 and 8 in other filamentous fungi. Since the most or all of the genome sequences of other filamentous fungi, e.g., *Aspergillus* (e.g., *Aspergillus fumigatus, Aspergillus oryzae* (see, e.g., Machida et al, Nature 2005 438, 1157-1161), *Aspergillus nidulans, Aspergillus fumigatus, Aspergillus niger, Aspergillus flavus, Aspergillus terreus*), *Neurospora* (e.g., *Neurospora crassa*), and *Fusarium* (e.g., *Fusarium graminearum*) are available, functional equivalents of SEQ ID NO: 7 and 8 that have promoter activity are readily identifiable.

As noted above, a subject promoter may have promoter activity in a host cell. Promoter activity may be detected using any suitable assay. In certain embodiments, a subject promoter may be operably linked to a polynucleotide, and transcription of the polynucleotide may be detected using any suitable method, e.g., Northern blotting or RT-PCR, etc. In other embodiments, the promoter may be operably linked to a polynucleotide that encodes a protein, e.g., a reporter protein, and the activity of the promoter can be evaluated by detecting the protein. In these embodiments, if necessary, a 5' untranslated region may be linked to the promoter such that the resultant transcript has a 5' UTR followed by a coding sequence. As would be recognized, the results obtained from such an assay may be compared to results compared to a suitable control, e.g., a negative or positive control, to determine the significance of results obtained. Any host cell, e.g., a bacterial host cell such as *E. coli, Bacillus* or *Streptomyces* host cell, or a filamentous fungal cell, e.g., an *Aspergillus* ssp., *Trichoderma* ssp. or *Fusarium* ssp. host cell may be employed. There is no requirement for a subject promoter to be contained within a particular host cell. In certain cases, the promoter may be tested for promoter activity in a *Trichoderma reesei* host cell.

A recombinant nucleic acid comprising the subject promoter is also provided. In certain cases, the recombinant nucleic acid may comprise a subject promoter and a polynucleotide, where the promoter and the polynucleotide are operably linked such that the promoter causes transcription of the polynucleotide in a cell. In certain cases, the promoter and polynucleotide are not normally linked in nature, i.e., are heterologous to each other. In certain cases, the polynucleotide may contain a coding sequence for a protein. The protein may be an enzyme, a reporter or a therapeutic protein (e.g., an antibody protein), as discussed above, for example. In certain embodiments, the protein may be a fusion protein which may, in certain cases, contain a signal sequence or carrier portion for secretion of the protein.

A nucleic acid vector comprising the subject recombinant nucleic acid is also provided, as well as a host cell containing the same. In certain embodiments, the recombinant nucleic acid may be present in the genome of the host cell. In other embodiments, the recombinant nucleic acid may be present in a vector that replicates in the cell. The host cell may be any of a variety of different host cells, including bacterial, fungal, yeast, plant and mammalian host cells. In one embodiment, the host cell may be a filamentous fungal host cell, and in another embodiment, the host cell may be a bacterial cell.

A culture of cells comprising culture medium and a subject host cell is also provided.

A method of producing a protein is also provided. In general terms, this method includes to maintaining a subject culture of cells under conditions suitable to produce the protein. This method may further include recovering the protein from culture medium.

In order to further illustrate the present invention and advantages thereof, the following specific examples are given with the understanding that they are being offered to illustrate the present invention and should not be construed in any way as limiting its scope.

EXAMPLE 1

Isolation of ALS Genes from Chlorimuron Ethyl-Resistant Cells

Chlorimuron ethyl (Chem Service Inc., West Chester, Pa.), freshly prepared and dissolved in DMF to a concentration of 20 mg/ml, was added at various concentrations to molten Vogels agar immediately prior to pouring the plates to produce media containing 25, 50, 100, 200, 300, 400 or 500 ppm chlorimuron ethyl.

Approximately 25 million spores *T. reesei* strain QM6a (ATCC 13631) were plated onto each plate. After 10 days of growth at 28° C., five colonies were isolated, two from 50 ppm plates and one each from each of the 25, 200 and 300 ppm plates. The colonies were further isolated by restreaking them onto fresh Vogels agar plates containing 200 ppm chlorimuron ethyl.

Genomic DNA was prepared from each of the five chlorimuron ethyl resistant strains in order to amplify and sequence the acetolactate synthase (als) gene from those strains. Herculase DNA polymerase (Stratagene, La Jolla, Calif.) was used for amplification following manufacturers instructions and the following primers: Forward (5'-3') GGCGCGCCTGAGACAATGGCCGGCAATGGTAAAAA (SEQ ID NO:5) and Reverse (5'-3') GCGATCGCCATC-CCGTCGCGTCAAAAACACTGC (SEQ ID NO:6)

Unique restriction sites were added to the 5' ends of the primers for subsequent manipulation. The resulting 4.1 kb fragments were isolated, sequenced and compared to the sequence of the native *T. reesei* acetolactate synthase gene (from the JGI genome website).

Three unique point mutations in the als gene that confer resistance to chlorimuron ethyl were identified.

Compared to the sequence of the wild-type *T. reesei* acetolactate synthase protein (FIG. 1; SEQ ID NO:1), the clorimuron ethyl-resistant acetolactate synthase proteins each had one of the following amino acid substitutions: A190D, K241E or R372H. The amino acids at positions 190, 241 and 372 of the wild-type *T. reesei* acetolactate synthase protein of SEQ ID NO:1 are underlined.

Compared to the sequence of the wild-type *T. reesei* acetolactate synthase deduced cDNA (FIG. 2; SEQ ID NO:2), the clorimuron ethyl-resistant acetolactate synthase cDNAs each had one of the following nucleotide substitutions: C569A (this corresponds to the A190D amino acid substitution), A721G (this corresponds to the K241E amino acid substitution) or G1115A (this corresponds to the R372H amino acid substitution). Each of the altered codons (GCC, which is altered to GAC; AAG, which is altered to GAG; and CGT, which is altered to CAT) is indicated on FIG. 2.

Compared to the sequence of the wild-type *T. reesei* acetolactate synthase gene (FIG. 3; SEQ ID NO:3), the clorimuron ethyl-resistant acetolactate synthase genes each had one of the following nucleotide substitutions: C1023A (this corresponds to the A190D amino acid substitution), A1175G (this corresponds to the K241E amino acid substitution) or G1569A (this corresponds to the R372H amino acid substitution).

Because of the degeneracy of the genetic code, other mutations in the als coding sequence can encode the A190D, K241E or R372H amino acid substitutions.

EXAMPLE 2

Transformation of *T. reesei* with A190D Acetolactate Synthase Gene

The vector pTrex-glucoamylase was created to express a glucoamylase derived from *Trichoderma reesei* in *T. reesei*. FIG. 4 depicts a general diagram of the vector. Three different vector constructs have been made with different promoters; 1818A, 1818B and the *T. reesei* cbh1 promoter. FIG. 5A illustrates the sequences of the promoter designated 1818A and FIG. 5B illustrates the sequences of the promoter 1818B.

The entire nucleotide sequence of the pTrex-glucoamylase including the cbh1 promoter is shown in FIG. 6. The pTrex-glucoamylase vector is based on vector pTrex3g as described in detail in WO 05/001036. In brief, the pTrex3g is based on the *E. coli* vector pSL1180 (Pharmacia, Inc., Piscataway, N.J.) which is a pUC118 phagemid based vector with an extended multiple cloning site containing 64 hexamer restriction enzyme recognition sequences. It was designed as a Gateway destination vector (Hartley, J. L. et al., (2000) Genome Research 10:1788-1795) to allow insertion using Gateway Technology (Invitrogen) of any desired open reading frame between the promoter and terminator regions of the *T. reesei* cbh1 gene.

In the pTrex-glucoamylase vector, the A190D ALS gene is under control of its native promoter and terminator and is used to replace the fungal selectable marker amdS which is used in pTrex3g.

The vector was transformed into the quad deleted (Δchb1, Δcbh2, Δegl1, and Δegl2) *T. reesei* strain (WO 05/001036) originally derived from RL-P37 (Sheir-Neiss et al., (1984) Appl. Microbiol. Biotechnol. 20:46-53; U.S. Pat. No. 4,797,361) using the procedure outlined below.

A suspension of spores (approximately $5 \times 10^8$ spores/ml) from the *Trichoderma* strain was prepared. 100 ul-200 ul of spore suspension was spread onto the center of plates of modified Vogels medium with 200 ppm chlorimuron ethyl and allowed to dry.

Modified Vogels had the following composition: 2.5 g/L $Na_3Citrate*2H_2O$, 5.0 g/L $KH_2PO_4$, 2.0 g/L $NH_4NO_3$, 0.2 g/L $MgSO_4*7H_2O$), 0.1 g/L $CaCl_2*2H_2O$, 5 mL/L Modified Vogels Trace Elements Solution, 2.5 mL/L Modified Vogels Biotin Solution, 20 g/L Agar Modified Vogels trace elements solution contained 50 g/L Citric Acid, 50 g/L $ZnSO_4*7H_2O$, 10 g/L $Fe(NH_4)_2SO_4*6H_2O$, 2.5 g/L $CuSO_4*5H_2O$, 0.5 g/L $MnSO_4*4H_2O$, 0.5 g/L $H_3BO_3$, 0.5 g/L $NaMoO_4*2H_2O$.

Modified Vogels Biotin Solution contained 0.1 g/L d-Biotin. After autoclave the following additions are made prior to pouring plates: 20 mL/L of 50% glucose, 10 mL/L of 20 mg/mL chlorimuron ethyl dissolved DMF.

Transformation of the *Trichoderma* strain by the biolistic transformation method was accomplished using a Biolistic® PDS-1000/he Particle Delivery System from Bio-Rad (Hercules, Calif.) following the manufacturers instructions (see, WO 05/001036 and US 2006/0003408).

Figure 7:
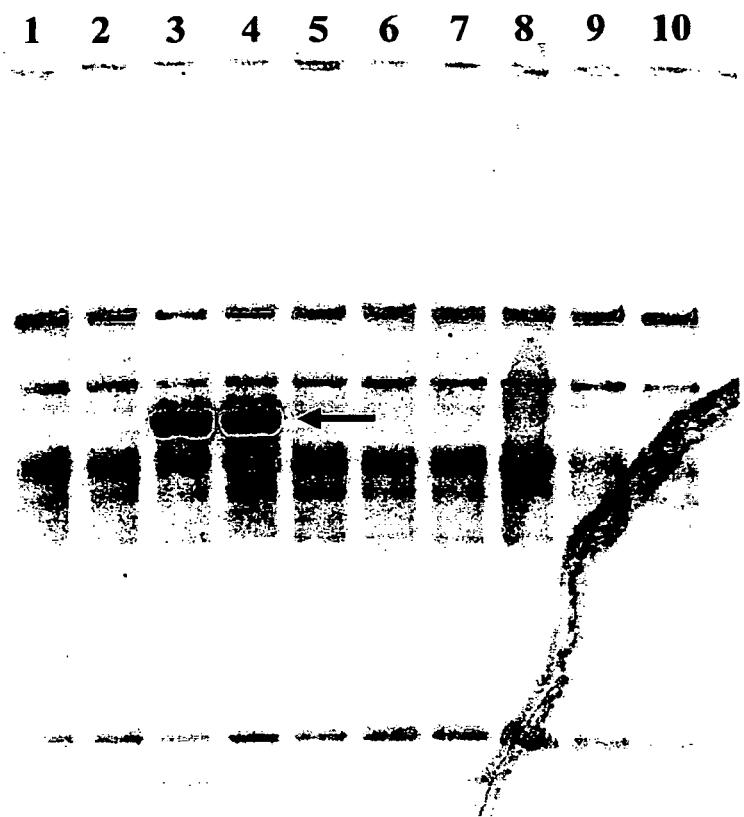
FIG. 7 illustrates an SDS-PAGE gel of supernatant samples from shake flask grown transformant. Lane 1 depicts the untransformed control. Expression of the *T. reesei* glucoamylase is shown in lanes 3 and 4 as highlighted by the arrow.

Transformants were isolated after 3 to 4 days of growth at 28° C. Transformants were serially passed twice on fresh Vogels plates with 200 ppm chlorimuron ethyl in order to isolate stable monokaryons. Transformants were cultured, and culture supernatant was tested by SDS page electrophoresis and using an enzyme assay. An SDS PAGE gel is shown in FIG. 7 illustrating the expression of the *T. reesei* glucoamylase.

EXAMPLE 3

Sequencing and Cloning of the 1818A and 1818B Promoters

The 1818A and 1818B promoters (as shown in FIGS. 5A and 5B, respectively) were identified by mining the US Department of Energy Joint Genome Institute's *Trichoderma reesei* genome sequence database (as found at the world wide website of jgi.doe.gov) for sequences upstream of highly represented ESTs.

Figure 8:
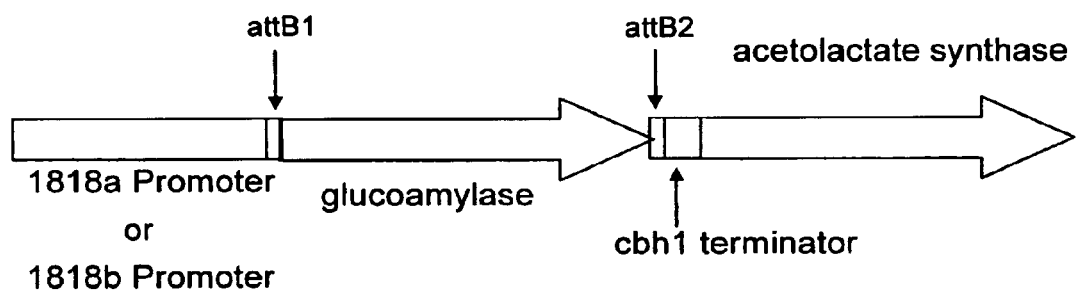
FIG. 8 is a diagram of the vector used to test the 1818A and 1818B promoters.

The promoters were amplified by PCR and cloned behind a glucoamylase coding sequence in accordance with the vector map shown in FIG. 8. The entire nucleotide sequence of this construct is shown in FIG. 9. The vector used is based on the vector pTrex3g, which is described in detail in Example 6 of WO 05/001036. In brief, the pTrex3g is based on the *E. coli* vector pSL1180 (Pharmacia, Inc., Piscataway, N.J.) which is a pUC118 phagemid based vector with an extended multiple cloning site containing 64 hexamer restriction enzyme recognition sequences. It was designed as a Gateway destination vector (Hartley, J. L. et al., (2000) Genome Research 10:1788-1795) to allow insertion using Gateway Technology (Invitrogen) of any desired open reading frame between the promoter and terminator regions of the *T. reesei* cbh1 gene. In the vector used in this example, the cbh1 promoter was replaced with either the 1818A or the 1818B promoter, the amdS selectable marker was replaced with a *Trichoderma reesei* acetolactate synthase marker, driven by its native promoter and terminator.

EXAMPLE 4

Transformation of *T. reesei* Host Cells with Vectors Including the 1818A and 1818B Promoters The vector was transformed into the quad deleted (Δchb1, Δcbh2, Δegl1, and Δegl2) *T. reesei* strain (WO 05/001036) originally derived from RL-P37 (Sheir-Neiss et al., (1984) Appl. Microbiol. Biotechnol. 20:46-53 and U.S. Pat. No. 4,797,361) using the procedure outlined below.

A suspension of spores (approximately $5 \times 10^8$ spores/ml) from the *Trichoderma* strain was prepared. 100 ul-200 ul of spore suspension was spread onto the center of plates of modified Vogels medium with 200 ppm chlorimuron ethyl. Modified Vogels had the following composition: 2.5 g/L $Na_3Citrate*2H_2O$, 5.0 g/L $KH_2PO_4$, 2.0 g/L $NH_4NO_3$, 0.2 g/L $MgSO_4*7H_2O$). 1 g/L $CaCl_2*2H_2O$, 5 mL Modified Vogels Trace Elements Solution, 2.5 mL Modified Vogels Biotin Solution, 20 g/L Agar Modified Vogels trace elements solution contained 50 g/L Citric Acid, 50 g/L $ZnSO_4*7H_2O$, 10 g/L $Fe(NH_4)_2SO_4*6H_2O$, 2.5 g/L $CuSO_4*5H_2O$, 0.5 g/L $MnSO_4*4H_2O$, $0.5H_3BO_3$, 0.5 g/L $NaMoO_4*2H_2O$. Modified Vogels Biotin Solution contained 0.1 g/L d-Biotin. After autoclave the following additions are made prior to pouring plates: 20 mL/L of 50% glucose, 10 mL/L of 20 mg/mL chlorimuron ethyl dissolved DMF. The spore suspension was allowed to dry on the surface of the Modified Vogels plates.

Transformation of the *Trichoderma* strain by the biolistic transformation method was accomplished using a Biolistic® PDS-1000/he Particle Delivery System from Bio-Rad (Hercules, Calif.) following the manufacturers instructions (see, WO 05/001036 and US 2006/0003408).

Transformants were isolated.

EXAMPLE 5

Screening Transformants for Expression of Glucoamylase Activity Driven by 1818A and 1818B Promoters Stable transformants were grown on Modified Vogels Lactose Agar plates with starch (9 cm diameter petri-plates). After about 4 days growth at 28° C., 10 ml of a 1 mg/ml solution of 4-methyl-umbelliferyl-α-D-glucose was poured over the grown colonies. After 30 minutes at room temperature, strains expressing glucoamylase were visualized as fluorescent blue colonies when viewed illuminated by a long wavelength UV lamp. The untransformed, parent *T. reesei* control strain did not show blue fluorescence.

Modified Vogels Lactose Agar Plates with starch is the same recipe as Modified Vogels Agar except that 25 ml/L of 20% α-lactose solution (added after autoclaving) is substituted for glucose solution and 20 g/L of Pure Food Powder cornstarch is added prior to autoclaving.

The glucoamylase substrate 4-methyl-umbelliferyl-α-D-glucose was prepared as follows: 200 mg of 4-methyl-umbelliferyl-α-D-glucose (Sigma-Aldrich Co.) is dissolved in 5 ml of DMSO and 195 ml of 75 mM Potassium Phosphate Buffer pH 6.3 is added.

EXAMPLE 6

Shake Flask Experiments with *Trichoderma reesei* Transformants

Individual fungal transformants will be grown up in shake flask culture to determine the level of glucoamylase protein expression. The experiments will be conducted essentially as described in example 1 of U.S. Pat. No. 5,874,276 with the following modification: 16 g/L of alpha-lactose was substituted for cellulose in TSF medium.

In general, the fermentation protocol as described in Foreman et al. (Foreman et al. (2003) *J. Biol. Chem.* 278:31988-31997) will be followed. Vogels minimal medium (Davis et al., (1970) Methods in Enzymology 17A, pg 79-143 and Davis, Rowland, NEUROSPORA, CONTRIBUTIONS OF A MODEL ORGANISM, Oxford University Press, (2000)) containing 5% glucose will be inoculated with 1.5 ml frozen spore suspension. After about 48 hours, each culture will be transferred to 6.2 L of the same medium in a 14 L Biolafitte fermenter. The fermenter will be run at 25° C., 750 RPM and 8 standard liters per minute airflow. About one hour after the initial glucose is exhausted, a 25% (w/w) lactose feed will be started and fed in a carbon limiting fashion to prevent lactose accumulation. The concentrations of glucose and lactose will be monitored. Samples will be obtained at regular intervals to monitor the progress of the fermentation. Collected samples will be spun in a 50 ml centrifuge tube at ¾ speed in an International Equipment Company (Needham Heights, Mass.) clinical centrifuge. Shake flask grown supernatant samples will be run on BIS-TRIS SDS-PAGE gels (Invitrogen), under reducing conditions with MOPS (morpholinepropanesulfonic acid) SDS running buffer and LDS sample buffer.

The invention claimed is:

1. An isolated polynucleotide encoding an acetolactate synthase protein that provides resistance to toxic sulphonylurea compounds, wherein the amino acid sequence of said acetolactate protein is at least 95% identical to SEQ ID NO:1.

2. The isolated polynucleotide of claim 1, wherein said protein contains an acidic amino acid at position 190.

3. The isolated polynucleotide of claim 1, wherein said protein contains a basic amino acid at position 241.

4. The isolated polynucleotide of claim 1, wherein said protein contains a basic amino acid at position 372.

5. The isolated polynucleotide of claim 1, wherein said isolated polynucleotide is operably linked to a promoter and a terminator.

6. The isolated polynucleotide of claim 1, wherein said isolated polynucleotide comprises introns.

7. The isolated polynucleotide of claim 6, wherein said isolated polynucleotide is at least 95% identical to SEQ ID NO:1.

8. The isolated polynucleotide of claim 1, wherein said isolated polynucleotide comprises a single open reading frame.

9. The isolated polynucleotide of claim 1, wherein said isolated polynucleotide is 95% identical to SEQ ID NO:2.

10. The isolated polynucleotide of claim 1, wherein said isolated polynucleotide is codon-optimized for expression of said acetolactate synthase protein in a particular host cell.

11. A vector comprising the isolated polynucleotide of claim 1.

12. The vector of claim 11, wherein said vector further comprises an expression cassette for expression of a recombinant protein.

13. A host cell comprising the isolated polynucleotide of claim 1, wherein said host cell is resistant to toxic sulphonylurea compounds.

14. The host cell of claim 13, wherein said host cell is a fungal host cell.

15. The host cell of claim 14, wherein said host cell is a filamentous fungal host cell.

16. The host cell of claim 15, wherein said host cell is a *Trichoderma reesei* host cell.

17. The host cell of claim 13, wherein said host cell is a plant cell.

18. The host cell of claim 13, wherein the isolated polynucleotide is present in the genome of said host cell.

19. The host cell of claim 13, wherein said isolated polynucleotide is present in a vector that autonomously replicates in said host cell.

20. A method of selecting a culture of cells resistant to a toxic sulphonylurea or imidazolinone compound, comprising the steps of:
    (a) introducing the isolated polynucleotide of claim 1 into a plurality of cells;
    (b) culturing said cells in the presence of an herbicidal amount of the toxic sulphonylurea or imidazolinone compound; and
    (c) determining the presence or absence of growth of said cells, wherein the growth of said cells indicates that said cells are resistant to the sulphonylurea or imidazolinone compound.

21. The method of claim 20, wherein said cells are fungal cells.

22. The method of claim 21, wherein said cells are *Trichoderma reesei* cells.

23. The method of claim 20, wherein said cells are plant cells.

24. The method of claim 20, wherein the cells are cultured in a liquid medium.

* * * * *

SEQUENCE LISTING

<160> NUMBER OF SEQ ID NOS: 10

<210> SEQ ID NO 1
<211> LENGTH: 683
<212> TYPE: PRT
<213> ORGANISM: Trichoderma reesei

<400> SEQUENCE: 1

Met Leu Arg Ser Arg Gln Val Thr Ala Arg Ala Val Arg Ala Leu Gly
 1               5                  10                  15

Gln Ala Arg Ala Phe Thr Ser Thr Thr Lys Pro Val Met Ile Gln Ser
                20                  25                  30

Ser Gln Arg Lys Gln Ala Asn Ala Ser Ala Ala Pro Gln Val Arg Pro
            35                  40                  45

Val Pro Ser Pro Ala Phe Asn Ala Glu Asp Lys Asp Arg Ser His Val
        50                  55                  60

Gln Pro Leu Val Asn Pro Ser Lys Pro Asp Met Asp Glu Ser Phe Ile
65                  70                  75                  80

Gly Lys Thr Gly Gly Glu Ile Phe His Glu Met Met Leu Arg Gln Gly
                85                  90                  95

Val Lys His Ile Phe Gly Tyr Pro Gly Gly Ala Ile Leu Pro Val Phe
            100                 105                 110

Asp Ala Ile Tyr Asn Ser Lys His Phe Asp Phe Ile Leu Pro Arg His
        115                 120                 125

Glu Gln Gly Ala Gly His Met Ala Glu Gly Tyr Ala Arg Ala Ser Gly
    130                 135                 140

Lys Pro Gly Val Val Leu Val Thr Ser Gly Pro Gly Ala Thr Asn Val
145                 150                 155                 160

Ile Thr Pro Met Gln Asp Ala Leu Ser Asp Gly Thr Pro Leu Val Val
                165                 170                 175

Phe Cys Gly Gln Val Pro Thr Thr Ala Ile Gly Ser Asp Ala Phe Gln
            180                 185                 190

Glu Ala Asp Val Val Gly Ile Ser Arg Ala Cys Thr Lys Trp Asn Val
        195                 200                 205

Met Val Lys Ser Val Ala Glu Leu Pro Arg Arg Ile Asn Glu Ala Phe
    210                 215                 220

```
Glu Ile Ala Thr Ser Gly Arg Pro Gly Pro Val Leu Val Asp Leu Pro
225                 230                 235                 240

Lys Asp Val Thr Ala Gly Ile Leu Arg Arg Ala Ile Pro Thr Glu Thr
                245                 250                 255

Ala Leu Pro Ser Leu Pro Ser Ala Ala Ser Arg Ala Ala Met Glu Leu
            260                 265                 270

Ser Ser Lys Gln Leu Asn Ala Ser Ile Lys Arg Ala Ala Asp Leu Ile
        275                 280                 285

Asn Ile Ala Lys Lys Pro Val Ile Tyr Ala Gly Gln Gly Val Ile Gln
290                 295                 300

Ser Glu Gly Gly Val Glu Leu Leu Lys Gln Leu Ala Asp Lys Ala Ser
305                 310                 315                 320

Ile Pro Val Thr Thr Thr Leu His Gly Leu Gly Ala Phe Asp Glu Leu
                325                 330                 335

Asp Glu Lys Ser Leu His Met Leu Gly Met His Gly Ser Ala Tyr Ala
            340                 345                 350

Asn Met Ala Met Gln Gln Ala Asp Leu Ile Ile Ala Leu Gly Ser Arg
        355                 360                 365

Phe Asp Asp Arg Val Thr Leu Asn Val Ser Lys Phe Ala Pro Ala Ala
370                 375                 380

Arg Gln Ala Ala Ala Glu Gly Arg Gly Gly Ile Ile His Phe Glu Ile
385                 390                 395                 400

Met Pro Lys Asn Ile Asn Lys Val Ile Gln Ala Thr Glu Ala Val Glu
                405                 410                 415

Gly Asp Val Ala Thr Asn Leu Lys His Leu Ile Pro Gln Ile Ala Glu
            420                 425                 430

Lys Ser Met Ala Asp Arg Gly Glu Trp Phe Gly Leu Ile Asn Glu Trp
        435                 440                 445

Lys Lys Lys Trp Pro Leu Ser Asn Tyr Gln Arg Ala Glu Arg Ala Gly
450                 455                 460

Leu Ile Lys Pro Gln Thr Val Met Glu Glu Ile Ser Asn Leu Thr Ala
465                 470                 475                 480

Asn Arg Lys Asp Lys Thr Tyr Ile Ala Thr Gly Val Gly Gln His Gln
                485                 490                 495

Met Trp Val Ala Gln His Phe Arg Trp Arg His Pro Arg Ser Met Ile
            500                 505                 510

Thr Ser Gly Gly Leu Gly Thr Met Gly Tyr Gly Leu Pro Ala Ala Ile
        515                 520                 525

Gly Ala Lys Val Ala Gln Pro Asp Ala Leu Val Ile Asp Val Asp Gly
530                 535                 540

Asp Ala Ser Phe Asn Met Thr Leu Thr Glu Leu Ser Thr Ala Ala Gln
545                 550                 555                 560

Phe Asn Ile Gly Val Lys Val Val Leu Asn Asn Glu Glu Gln Gly
                565                 570                 575

Met Val Thr Gln Trp Gln Asn Leu Phe Tyr Glu Asp Arg Tyr Ala His
            580                 585                 590

Thr His Gln Lys Asn Pro Asp Phe Met Lys Leu Ala Asp Ala Met Gly
        595                 600                 605

Val Gln His Gln Arg Val Thr Glu Pro Glu Lys Leu Val Asp Ala Leu
610                 615                 620

Thr Trp Leu Ile Asn Thr Asp Gly Pro Ala Leu Leu Glu Val Val Thr
625                 630                 635                 640

Asp Lys Lys Val Pro Val Leu Pro Met Val Pro Ala Gly Ser Ala Leu
                645                 650                 655
```

His Glu Phe Leu Val Phe Glu Pro Glu Lys Asp Lys Gln Arg Arg Glu
                660                 665                 670

Leu Met Lys Glu Arg Thr Lys Gly Val His Ser
        675                 680

<210> SEQ ID NO 2
<211> LENGTH: 2052
<212> TYPE: DNA
<213> ORGANISM: Trichoderma reesei

<400> SEQUENCE: 2

| | | | | | |
|---|---|---|---|---|---|
| atgctccgaa | gtcgccaagt | cacagccagg | gccgtccggg | ctctgggcca | ggcgcgcgcc | 60 |
| tttacctcga | cgaccaagcc | tgtcatgatc | agagcagcc | agaggaaaca | ggccaacgcc | 120 |
| agcgctgctc | cacaagtccg | ccctgtaccg | agccctgctt | tcaacgctga | agacaaagac | 180 |
| cgcagccatg | tgcagcctct | ggtcaacccg | tcgaagcccg | acatggatga | atcattcatt | 240 |
| ggcaaaaccg | gaggcgaaat | cttccacgag | atgatgctgc | gacagggtgt | caagcacatt | 300 |
| ttcggatacc | tggcggcgc | tatcctgccc | gtcttcgacg | ccatctacaa | ctcaaaacac | 360 |
| ttcgacttca | tcctgccccg | tcatgagcag | ggagctggcc | atatggccga | gggctatgcc | 420 |
| cgtgcctcgg | gcaaacccgg | tgtcgtcctg | gtgacttccg | gccccggtgc | taccaatgtc | 480 |
| atcacgccca | tgcaggatgc | cctgtcggac | ggaacgccct | tggtcgtctt | ctgcggccag | 540 |
| gtccccacca | cggccatcgg | cagcgatgcc | ttccagagg | ccgacgtcgt | gggcatctcg | 600 |
| cgggcctgca | ccaagtggaa | cgtcatggtc | aagagcgttg | ctgagctgcc | gcggagaatc | 660 |
| aacgaggcct | ttgagattgc | caccagcggc | cgccctggcc | ccgtcctcgt | cgacctgccc | 720 |
| aaggatgtca | cggctggtat | cctgaggaga | gccatcccta | cggagactgc | tctgccgtct | 780 |
| ctgcccagtg | ccgcctcccg | cgccgccatg | gagctgagct | ccaagcagct | caacgcctcc | 840 |
| atcaagcgtg | ccgccgacct | catcaacatc | gccaagaagc | ccgtcatcta | cgccggtcag | 900 |
| ggtgtcatcc | agtccgaggg | cggcgttgag | ctcctgaagc | agctggcgga | caaggcctcc | 960 |
| atccccgtca | ccaccaccct | ccatggcctg | ggtgccttg | atgagctgga | cgagaagtcg | 1020 |
| ctgcacatgc | tgggcatgca | cggctcggcg | tatgccaaca | tggccatgca | gcaggccgac | 1080 |
| ctcatcatcg | ccctcggcag | ccgattcgac | gaccgtgtta | ctctgaatgt | ctccaaattt | 1140 |
| gcgcctgcag | ccaggcaagc | tgctgccgag | ggccgcggcg | gcatcattca | ctttgagatc | 1200 |
| atgcccaaga | acatcaacaa | ggtcatccag | gcgaccgagg | ccgtcgaggg | cgacgtcgcc | 1260 |
| accaacctga | agcacctcat | tccccagatt | gccgaaaagt | ccatggcgga | ccgaggagag | 1320 |
| tggttcggcc | tcatcaatga | gtggaagaag | aagtggcccc | tgtcaaacta | ccagcgcgcg | 1380 |
| gagcgggctg | gcctcatcaa | gccgcagacg | gtcatggagg | agattagcaa | cctgacggcc | 1440 |
| aaccgaaagg | acaagacgta | cattgccacg | ggtgtcggcc | agcaccagat | gtgggttgcc | 1500 |
| cagcacttcc | gctggaggca | ccctcgatcc | atgattacct | ctggtggtct | gggcaccatg | 1560 |
| ggctacggtc | tccccgcggc | cattggcgcc | aaggtggccc | agcccgacgc | tctcgtaatt | 1620 |
| gacgttgatg | gcgatgcctc | gtttaacatg | acgctgacgg | agctgtcgac | tgctgcacag | 1680 |
| ttcaacattg | gcgtcaaggt | ggttgtgctc | aacaacgagg | agcagggcat | ggtgacgcag | 1740 |
| tggcagaacc | tcttttacga | ggaccgatat | gcccacacgc | accagaagaa | ccccgacttc | 1800 |
| atgaagctgg | ccgacgccat | gggcgttcag | caccagcgcg | tgacggagcc | ggagaagctg | 1860 |
| gtcgatgccc | tgacgtggct | gatcaacacc | gatggcccgg | ccctgttgga | ggttgtcacg | 1920 |
| gacaagaagg | tgcctgtcct | gcccatggtg | cccgccggat | cggccctgca | cgagttcctc | 1980 |

```
gtctttgaac ctgaaaagga taagcagcgc cgtgagctga tgaaggagag aacaaagggt    2040
gtgcactcct aa                                                       2052

<210> SEQ ID NO 3
<211> LENGTH: 4093
<212> TYPE: DNA
<213> ORGANISM: Trichoderma  reesei

<400> SEQUENCE: 3
tgagacaatg gccggcaatg gtaaaaagga ccaagatgta ctaggtagtt gcaatgtggc      60
ttattaccta cctactacct ggtaggcacc tactaggtac ttgggtagac ggacaatgaa     120
atttgaagtc ggggttgcag gaaagcaggg cgctggacac attgtgcttc aggcggtacc     180
cgtcgtcatc gtcagccaat gtcgaggccc ggcagcccga ggagcgagac aaccttggcc     240
ggaggagccc gcaggtacct gccaaagcgc ggctggtacc tctcaaccct ctcaggcctg     300
ttggatgccc tatgacatgc cctgggggat gcagctgttg cccggccccc gcactttcgg     360
gtgaccgcga ggctgctgat tggctggttg ccacgggctg ggcggtccct gaagttgttg     420
ccatctgaac tctgtcggcg ctggcgtcgg ctgcgcccaa tgggaggcga gacaactcag     480
ggtactagaa tcactgacag aagaagagaa tcgaaagtag gtagacagcc aattcgttgc     540
atggcaggca accgcacagg agaaaaattg actaccccac aatcaggcac agtaagtagg     600
gcacagtacg tatgtacaga caaggcgcaa gcgatactgc gcgacccggt acctcgccgg     660
cttgacacgt gcgacaggct actttactag tattcgcagc ggcgggtcgc gcattattac     720
atgtactgtg ccgccatttg atgactgggc tgctgcagta ttagtagatc tgcccggcat     780
cgcccttcca tgggcgcgac ccgggactgg accctctgac tctacctaca tgtacctagg     840
ccgggccggg cttggtgact tttgtccgat caggtcgttc gcctggctac ctattatttc     900
tctttcttct tctccatcct gcttctggcc ttgcaattct tcttcgccac tcctccctct     960
tccccccgcg ataccttga attcgtcaga gaggaaaaga cgagaaaaaa aagggcagca    1020
gagacgtcgg tctggctcac gtgctgcatc tctgcgcact ctcatttttt ttattgtccg    1080 accccctccct caaccttctc cttcgttgac aggctaagcc ttgcttcgac gctctctctt    1140 tgaattttc tacttctacc ttctttttctt gcgtgttacc caccatagct cgattcacga    1200
tgctccgaag tcgccaagtc acagccaggg ccgtccgggc tctgggccag gcgcgcgcct    1260
ttacctcgac gaccaagcct gtcatgatcc agagcagcca gaggaaacag gccaacgcca    1320
gcgctgctcc gtaagtcgcc cattgccatt gcatcttctg tttgatatat acttcctgct    1380
gcttgcgtgg cgtcgtctct cggttatgcg tgtcaaggac caggtgtgtt cgcatcgtgg    1440
ttttccagcg ccgattaccg ggggacgaat ttttggctgc tcaactcgcg cgcgcgcatt    1500
ctgattcttc gttttcaatc ttgagcgaca actggctaac ataatggcca ttggcaattg    1560
cttcacacag acaagtccgc cctgtaccga gccctgcttt caacgctgaa gacaaagacc    1620
gcagccatgt gcagcctctg gtcaacccgt cgaagcccga catggatgaa tcgtatgtcc    1680
acgtcccctc gtcccgccct acaaaatgaa cacgattaca ccagaatttt tgcaacaatc    1740
gacacttcta taacagacca attgagcttt gttctgacca atcatgttgc tctagattca    1800
ttggcaaaac cggaggcgaa atcttccacg agatgatgct gcgacagggt gtcaagcaca    1860
tttgtaggtt ccgatgccgg ccgcccacac gggctccatc cttgctccat ctctccagct    1920
aggcaaatct cgctaacctt gagtcaccat ccagtcggat accctggcgg cgctatcctg    1980
cccgtcttcg acgccatcta caactcaaaa cacttcgact tcatcctgcc ccgtcatgag    2040
```

```
caggggagctg gccatatggc cgagggctat gcccgtgcct cgggcaaacc cggtgtcgtc    2100
ctggtgactt ccggccccgg tgctaccaat gtcatcacgc ccatgcagga tgccctgtcg    2160
gacggaacgc ccttggtcgt cttctgcggc caggtcccca ccacggccat cggcagcgat    2220
gccttccaag aggccgacgt cgtgggcatc tcgcgggcct gcaccaagtg gaacgtcatg    2280
gtcaagagcg ttgctgagct gccgcggaga atcaacgagg cctttgagat tgccaccagc    2340
ggccgccctg ccccgtcct cgtcgacctg cccaaggatg tcacggctgg tatcctgagg    2400
agagccatcc ctacggagac tgctctgccg tctctgccca gtgccgcctc ccgcgccgcc    2460
atggagctga gctccaagca gctcaacgcc tccatcaagc gtgccgccga cctcatcaac    2520
atcgccaaga agcccgtcat ctacgccggt cagggtgtca tccagtccga gggcggcgtt    2580
gagctcctga agcagctggc ggacaaggcc tccatccccg tcaccaccac cctccatggc    2640
ctgggtgcct ttgatgagct ggacgagaag tcgctgcaca tgctgggcat gcacggctcg    2700
gcgtatgcca acatggccat gcagcaggcc gacctcatca tcgccctcgg cagccgattc    2760
gacgaccgtg ttactctgaa tgtctccaaa tttgcgcctg cagccaggca agctgctgcc    2820
gagggccgcg gcggcatcat tcactttgag atcatgccca gaacatcaa caaggtcatc    2880
caggcgaccg aggccgtcga gggcgacgtc gccaccaacc tgaagcacct cattccccag    2940
attgccgaaa agtccatggc ggaccgagga gagtggttcg gcctcatcaa tgagtggaag    3000
aagaagtggc ccctgtcaaa ctaccagcgc gcggagcggg ctggcctcat caagccgcag    3060
acggtcatgg aggagattag caacctgacg gccaaccgaa aggacaagac gtacattgcc    3120
acgggtgtcg gccagcacca gatgtgggtt gcccagcact ccgctggag gcaccctcga    3180
tccatgatta cctctggtgg tctgggcacc atgggctacg gtctccccgc ggccattggc    3240
gccaaggtgg cccagcccga cgctctcgta attgacgttg atggcgatgc ctcgtttaac    3300
atgacgctga cggagctgtc gactgctgca cagttcaaca ttggcgtcaa ggtggttgtg    3360
ctcaacaacg aggagcaggg catggtgacg cagtggcaga acctctttta cgaggaccga    3420
tatgcccaca cgcaccagaa gaaccccgac ttcatgaagc tggccgacgc catgggcgtt    3480
cagcaccagc gcgtgacgga gccggagaag ctggtcgatg ccctgacgtg gctgatcaac    3540
accgatggcc cggccctgtt ggaggttgtc acggacaaga aggtgcctgt cctgcccatg    3600
gtgcccgccg gatcggccct gcacgagttc ctcgtctttg aacctggtga gtctacttca    3660
gacatattgc ttgcgcattg cagatactaa cactctcaca gaaaaggata agcagcgccg    3720
tgagctgatg aaggagagaa caaagggtgt gcactcctaa agcgatgatg tctgcgaggg    3780
gttcttcgtt gaaccctagt tcaggcacca tcttacccct cttatttttttc ccgtgggctt    3840
tcattttgtg tcatccgagc atgacgttgt agggttggag tttcttcctt tttatcttgt    3900
catttactgg tacccatagg cgcgagacta ggcttccatg ttttgttttg cgactttcaa    3960
aaagtacttt tagtggtttg gggcacgacg aggggggggca acctcttctg tcgaaaaagg    4020
tggctggatg gatgagatga gatgagatga gggtgaagat agatacctgc agtgttttttg    4080
acgcgacggg atg                                                       4093
```

<210> SEQ ID NO 4
<211> LENGTH: 2561
<212> TYPE: DNA
<213> ORGANISM: Trichoderma reesei

<400> SEQUENCE: 4

```
atgctccgaa gtcgccaagt cacagccagg gccgtccggg ctctgggcca ggcgcgcgcc    60
```

```
tttacctcga cgaccaagcc tgtcatgatc cagagcagcc agaggaaaca ggccaacgcc    120
agcgctgctc cgtaagtcgc ccattgccat tgcatcttct gtttgatata tacttcctgc    180
tgcttgcgtg gcgtcgtctc tcggttatgc gtgtcaagga ccaggtgtgt tcgcatcgtg    240
gttttccagc gccgattacc gggggacgaa ttttggctg ctcaactcgc gcgcgcgcat      300
tctgattctt cgttttcaat cttgagcgac aactggctaa cataatggcc attggcaatt    360
gcttcacaca gacaagtccg ccctgtaccg agccctgctt tcaacgctga agacaaagac    420
cgcagccatg tgcagcctct ggtcaacccg tcgaagcccg acatggatga atcgtatgtc    480
cacgtcccct cgtcccgccc tacaaaatga acacgattac accagaattt ttgcaacaat    540
cgacacttct ataacagacc aattgagctt tgttctgacc aatcatgttg ctctagattc    600
attggcaaaa ccggaggcga aatcttccac gagatgatgc tgcgacaggg tgtcaagcac    660
atttgtaggt tccgatgccg gccgcccaca cgggctccat ccttgctcca tctctccagc    720
taggcaaatc tcgctaacct tgagtcacca tccagtcgga tacccggcg gcgctatcct      780 gcccgtcttc gacgccatct acaactcaaa acacttcgac ttcatcctgc cccgtcatga    840
gcagggagct ggccatatgg ccgagggcta tgcccgtgcc tcgggcaaac ccggtgtcgt    900
cctggtgact tccggccccg gtgctaccaa tgtcatcacg cccatgcagg atgccctgtc    960
ggacggaacg cccttggtcg tcttctgcgg ccaggtcccc accacggcca tcggcagcga    1020
tgccttccaa gaggccgacg tcgtgggcat ctcgcgggcc tgcaccaagt ggaacgtcat    1080
ggtcaagagc gttgctgagc tgccgcggag aatcaacgag gcctttgaga ttgccaccag    1140
cggccgccct ggccccgtcc tcgtcgacct gcccaaggat gtcacggctg gtatcctgag    1200
gagagccatc cctacggaga ctgctctgcc gtctctgccc agtgccgcct cccgcgccgc    1260
catggagctg agctccaagc agctcaacgc ctccatcaag cgtgccgccg acctcatcaa    1320
catcgccaag aagcccgtca tctacgccgg tcagggtgtc atccagtccg agggcggcgt    1380
tgagctcctg aagcagctgg cggacaaggc ctccatcccc gtcaccacca ccctccatgg    1440
cctgggtgcc tttgatgagc tggacgagaa gtcgctgcac atgctgggca tgcacggctc    1500
ggcgtatgcc aacatggcca tgcagcaggc cgacctcatc atcgccctcg gcagccgatt    1560
cgacgaccgt gttactctga atgtctccaa atttgcgcct gcagccaggc aagctgctgc    1620
cgagggccgc ggcggcatca ttcactttga gatcatgccc aagaacatca acaaggtcat    1680
ccaggcgacc gaggccgtcg agggcgacgt cgccaccaac ctgaagcacc tcattcccca    1740
gattgccgaa aagtccatgg cggaccgagg agagtggttc ggcctcatca atgagtggaa    1800
gaagaagtgg cccctgtcaa ctaccagcg cgcggagcgg gctggcctca tcaagccgca      1860
gacggtcatg gaggagatta gcaacctgac ggccaaccga aaggacaaga cgtacattgc    1920
cacgggtgtc ggccagcacc agatgtgggt tgcccagcac ttccgctgga ggcaccctcg    1980
atccatgatt acctctggtg gtctgggcac catgggctac ggtctccccg cggccattgg    2040
cgccaaggtg gcccagcccg acgctctcgt aattgacgtt gatggcgatg cctcgtttaa    2100
catgacgctg acggagctgt cgactgctgc acagttcaac attggcgtca aggtggttgt    2160
gctcaacaac gaggagcagg gcatggtgac gcagtggcag aacctctttt acgaggaccg    2220
atatgcccac acgcaccaga gaacccccga cttcatgaag ctggccgacg ccatgggcgt    2280
tcagcaccag cgcgtgacgg agccggagaa gctggtcgat gccctgacgt ggctgatcaa    2340
caccgatggc ccgccctgt ggaggttgt cacggacaag aaggtgcctg tcctgcccat       2400
ggtgcccgcc ggatcggccc tgcacgagtt cctcgtcttt gaacctggtg agtctacttc    2460
```

```
agacatattg cttgcgcatt gcagatacta acactctcac agaaaaggat aagcagcgcc    2520
gtgagctgat gaaggagaga acaaagggtg tgcactccta a                       2561

<210> SEQ ID NO 5
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 5
ggcgcgcctg agacaatggc cggcaatggt aaaaa                               35

<210> SEQ ID NO 6
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 6
gcgatcgcca tcccgtcgcg tcaaaaacac tgc                                 33

<210> SEQ ID NO 7
<211> LENGTH: 868
<212> TYPE: DNA
<213> ORGANISM: Trichoderma reesei

<400> SEQUENCE: 7
taggctggcg ggttggtgct tttgcccttt gtctgccgcg acctcttggt gacgctgcat    60
cgtgttggct gtagctgcac gcccggcctc ttttctggca tctcgcacag actgtacgca   120
gaacatgtgt aagtgacttt ctattgtagg acttggatgg atgggagatg gctatagaca   180
acaagagcga caacaaggat tatagacagt tccattacct gggcgaccac catcgcactt   240
caccttgctc gcccggcagg actggcaggc gttggcaatc ttgagtcgct ccctgtacag   300
cgacaagggc gcctgagcct gcacctgagc ctgggcctga gtctgagcct gaagccgttg   360
atcctcgtct tgacgggcgg acatgacgct ttacgtgagc tgagtccagg gctgtcgtcg   420
gcaagtgatt cggcagccgg caggcacaga cgaaagataa gaagcggctc gttcaccaga   480
tccgaaggcg gaatgcaaga atgtccgatg atgtcgggga agagaaggcg atgcctcgtc   540
tatctgggag gcgagggaag aagggaaagc aactcccgcc tcggcacagc tactcattgg   600
tcagagcgga cttcggagta taaccacacg gctgacaaac ctgcatcgac cgtgatggcg   660
ttcttttggt ccaatcatgg ctgaatgcga cgttggttgt gtcggcccct gcagccaatg   720
agaagctggt ccgatcctgg ggacgaggga gaggcaagca tatcgtataa gtccaagctc   780
aagcttggcg gcaggtaccg gttgatgtgg tcgctgtata taagtaaaag aactcgattc   840
cgcttcggag ttttctctgt caccctttc                                     868

<210> SEQ ID NO 8
<211> LENGTH: 928
<212> TYPE: DNA
<213> ORGANISM: Trichoderma reesei

<400> SEQUENCE: 8
taggctggcg ggttggtgct tttgcccttt gtctgccgcg acctcttggt gacgctgcat    60
cgtgttggct gtagctgcac gcccggcctc ttttctggca tctcgcacag actgtacgca   120
gaacatgtgt aagtgacttt ctattgtagg acttggatgg atgggagatg gctatagaca   180
```

| | |
|---|---|
| acaagagcga caacaaggat tatagacagt tccattacct gggcgaccac catcgcactt | 240 |
| caccttgctc gcccggcagg actggcaggc gttggcaatc ttgagtcgct ccctgtacag | 300 |
| cgacaagggc gcctgagcct gcacctgagc ctgggcctga gtctgagcct gaagccgttg | 360 |
| atcctcgtct tgacgggcgg acatgacgct ttacgtgagc tgagtccagg gctgtcgtcg | 420 |
| gcaagtgatt cggcagccgg caggcacaga cgaaagataa gaagcggctc gttcaccaga | 480 |
| tccgaaggcg gaatgcaaga atgtccgatg atgtcgggga agagaaggcg atgcctcgtc | 540 |
| tatctgggag gcgagggaag aagggaaagc aactcccgcc tcggcacagc tactcattgg | 600 |
| tcagagcgga cttcggagta taaccacacg gctgacaaac ctgcatcgac cgtgatggcg | 660 |
| ttcttttggt ccaatcatgg ctgaatgcga cgttggttgt gtcggcccct gcagccaatg | 720 |
| agaagctggt ccgatcctgg ggacgaggga gaggcaagca tatcgtataa gtccaagctc | 780 |
| aagcttggcg gcaggtaccg gttgatgtgg tcgctgtata taagtaaaag aactcgattc | 840 |
| cgcttcggag ttttctctgt caccttcat ggacgaagag ctattgagcc gcatctttgc | 900 |
| ttcgttgtcc agcgtgaatt ctcctaca | 928 |

<210> SEQ ID NO 9
<211> LENGTH: 12229
<212> TYPE: DNA
<213> ORGANISM: Artificial Sequence
<220> FEATURE:
<223> OTHER INFORMATION: Synthetic construct

<400> SEQUENCE: 9

| | |
|---|---|
| aagcttacta gtacttctcg agctctgtac atgtccggtc gcgacgtacg cgtatcgatg | 60 |
| gcgccagctg caggcggccg cctgcagcca cttgcagtcc cgtggaattc tcacggtgaa | 120 |
| tgtaggcctt ttgtagggta ggaattgtca ctcaagcacc cccaacctcc attacgcctc | 180 |
| ccccatagag ttcccaatca gtgagtcatg gcactgttct caaatagatt ggggagaagt | 240 |
| tgacttccgc ccagagctga aggtcgcaca accgcatgat atagggtcgg caacggcaaa | 300 |
| aaagcacgtg gctcaccgaa agcaagatg tttgcgatct aacatccagg aacctggata | 360 |
| catccatcat cacgcacgac cactttgatc tgctggtaaa ctcgtattcg ccctaaaccg | 420 |
| aagtgcgtgg taaatctaca cgtgggcccc tttcggtata ctgcgtgtgt cttctctagg | 480 |
| tgccattctt ttcccttcct ctagtgttga attgtttgtg ttggagtccg agctgtaact | 540 |
| acctctgaat ctctggagaa tggtggacta cgactaccg tgcacctgca tcatgtatat | 600 |
| aatagtgatc ctgagaaggg gggttttggag caatgtggga ctttgatggt catcaaacaa | 660 |
| agaacgaaga cgcctctttt gcaaagtttt gtttcggcta cggtgaagaa ctggatactt | 720 |
| gttgtgtctt ctgtgtattt ttgtggcaac aagaggccag agacaatcta ttcaaacacc | 780 |
| aagcttgctc ttttgagcta caagaacctg tggggtatat atctagagtt gtgaagtcgg | 840 |
| taatcccgct gtatagtaat acgagtcgca tctaaatact ccgaagctgc tgcgaacccg | 900 |
| gagaatcgag atgtgctgga aagcttctag cgagcggcta aattagcatg aaaggctatg | 960 |
| agaaattctg gagacggctt gttgaatcat ggcgttccat tcttcgacaa gcaaagcgtt | 1020 |
| ccgtcgcagt agcaggcact cattcccgaa aaaactcgga gattcctaag tagcgatgga | 1080 |
| accggaataa tataataggc aatacattga gttgcctcga cggttgcaat gcaggggtac | 1140 |
| tgagcttgga cataactgtt ccgtacccca cctcttctca acctttggcg tttccctgat | 1200 |
| tcagcgtacc cgtacaagtc gtaatcacta ttaacccaga ctgaccggac gtgttttgcc | 1260 |
| cttcatttgg agaaataatg tcattgcgat gtgtaatttg cctgcttgac cgactggggc | 1320 |

```
tgttcgaagc ccgaatgtag gattgttatc cgaactctgc tcgtagaggc atgttgtgaa    1380
tctgtgtcgg gcaggacacg cctcgaaggt tcacggcaag ggaaaccacc gatagcagtg    1440
tctagtagca acctgtaaag ccgcaatgca gcatcactgg aaaatacaaa ccaatggcta    1500
aaagtacata agttaatgcc taaagaagtc atataccagc ggctaataat tgtacaatca    1560
agtggctaaa cgtaccgtaa tttgccaacg gcttgtgggg ttgcagaagc aacggcaaag    1620
ccccacttcc ccacgtttgt ttcttcactc agtccaatct cagctggtga tccccccaatt   1680
gggtcgcttg tttgttccgg tgaagtgaaa gaagacagag gtaagaatgt ctgactcgga    1740
gcgttttgca tacaaccaag ggcagtgatg gaagacagtg aaatgttgac attcaaggag    1800
tatttagcca gggatgcttg agtgtatcgt gtaaggaggt ttgtctgccg atacgacgaa    1860
tactgtatag tcacttctga tgaagtggtc catattgaaa tgtaaagtcg gcactgaaca    1920
ggcaaaagat tgagttgaaa ctgcctaaga tctcgggccc tcgggccttc ggcctttggg    1980
tgtacatgtt tgtgctccgg gcaaatgcaa agtgtggtag gatcgaacac actgctgcct    2040
ttaccaagca gctgagggta tgtgataggc aaatgttcag gggccactgc atggtttcga    2100
atagaaagag aagcttagcc aagaacaata gccgataaag atagcctcat taaacggaat    2160
gagctagtag gcaaagtcag cgaatgtgta tatataaagg ttcgaggtcc gtgcctccct    2220
catgctctcc ccatctactc atcaactcag atcctccagg agacttgtac accatctttt    2280
gaggcacaga aacccaatag tcaaccatca caagtttgta caaaaaagca ggctatgcac    2340
gtcctgtcga ctgcggtgct gctcggctcc gttgccgttc aaaaggtcct gggaagacca    2400
ggatcaagcg gtctgtccga cgtcaccaag aggtctgttg acgacttcat cagcaccgag    2460
acgcctattg cactgaacaa tcttctttgc aatgttggtc ctgatggatg ccgtgcattc    2520
ggcacatcag ctggtgcggt gattgcatct cccagcacaa ttgacccgga ctgtaagttg    2580
gccttgatga accatatcat atatcgccga gaagtggacc gcgtgctgag actgagacag    2640
actattacat gtggacgcga gatagcgctc ttgtcttcaa gaacctcatc gaccgcttca    2700
ccgaaacgta cgatgcgggc ctgcagcgcc gcatcgagca gtacattact gcccaggtca    2760
ctctccaggg cctctctaac ccctcgggct ccctcgcgga cggctctggt ctcggcgagc    2820
ccaagtttga gttgaccctg aagcctttca ccggcaactg gggtcgaccg cagcgggatg    2880
gcccagctct gcgagccatt gccttgattg gatactcaaa gtggctcatc aacaacaact    2940
atcagtcgac tgtgtccaac gtcatctggc ctattgtgcg caacgacctc aactatgttg    3000
cccagtactg gtcagtgctt gcttgctctt gaattacgtc tttgcttgtg tgtctaatgc    3060
ctccaccaca ggaaccaaac cggctttgac ctctgggaag aagtcaatgg gagctcattc    3120
tttactgttg ccaaccagca ccgaggtatg aagcaaatcc tcgacattcg ctgctactgc    3180
acatgagcat tgttactgac cagctctaca gcacttgtcg agggcgccac tcttgctgcc    3240
actcttggcc agtcgggaag cgcttattca tctgttgctc cccaggtttt gtgctttctc    3300
caacgattct gggtgtcgtc tggtggatac gtcgactcca acagtatgtc ttttcactgt    3360
ttatatgaga ttggccaata ctgatagctc gcctctagtc aacaccaacg agggcaggac    3420
tggcaaggat gtcaactccg tcctgacttc catccacacc ttcgatccca accttggctg    3480
tgacgcaggc accttccagc catgcagtga caaagcgctc tccaacctca aggttgttgt    3540
cgactccttc cgctccatct acggcgtgaa caagggcatt cctgccggtg ctgccgtcgc    3600
cattggccgg tatgcagagg atgtgtacta caacggcaac ccttggtatc ttgctacatt    3660
tgctgctgcc gagcagctgt acgatgccat ctacgtctgg aagaagacgg gctccatcac    3720
```

```
ggtgaccgcc acctccctgg ccttcttcca ggagcttgtt cctggcgtga cggccgggac    3780
ctactccagc agctcttcga cctttaccaa catcatcaac gccgtctcga catacgccga    3840
tggcttcctc agcgaggctg ccaagtacgt ccccgccgac ggttcgctgg ccgagcagtt    3900
tgaccgcaac agcggcactc cgctgtctgc gcttcacctg acgtggtcgt acgcctcgtt    3960
cttgacagcc acggcccgtc gggctggcat cgtgccccccc tcgtgggcca acagcagcgc   4020
tagcacgatc ccctcgacgt gctccggcgc gtccgtggtc ggatcctact cgcgtcccac    4080
cgccacgtca ttccctccgt cgcagacgcc caagcctggc gtgccttccg gtactcccta    4140
cacgcccctg ccctgcgcga ccccaacctc cgtggccgtc accttccacg agctcgtgtc    4200
gacacagttt ggccagacgg tcaaggtggc gggcaacgcc gcggccctgg caactggag     4260
cacgagcgcc gccgtggctc tggacgccgt caactatgcc gataaccacc ccctgtggat    4320
tgggacggtc aacctcgagg ctggagacgt cgtggagtac aagtacatca atgtgggcca    4380
agatggctcc gtgacctggg agagtgatcc caaccacact tacacggttc ctgcggtggc    4440
ttgtgtgacg caggttgtca aggaggacac ctggcagtcg taaacccagc tttcttgtac    4500
aaagtggtga tcgcgccagc tccgtgcgaa agcctgacgc accggtagat tcttggtgag    4560
cccgtatcat gacggcggcg ggagctacat ggccccgggt gatttatttt ttttgtatct    4620
acttctgacc ctttttcaaat atacggtcaa ctcatctttc actggagatg cggcctgctt    4680
ggtattgcga tgttgtcagc ttggcaaatt gtggctttcg aaaacacaaa acgattcctt    4740
agtagccatg cattttaaga taacggaata gaagaaagag gaaattaaaa aaaaaaaaa     4800
aacaaacatc ccgttcataa cccgtagaat cgccgctggc gcgcctgaga caatggccgg    4860
caatggtaaa aaggaccaag atgtactagg tagttgcaat gtggcttatt acctacctac    4920
tacctggtag gcacctacta ggtacttggg tagacggaca atgaaatttg aagtcggggt    4980
tgcaggaaag cagggcgctg gacacattgt gcttcaggcg gtacccgtcg tcatcgtcag    5040
ccaatgtcga ggcccggcag cccgaggagc gagacaacct tggccggagg agcccgcagg    5100
tacctgccaa agcgcggctg gtacctctca accctctcag gcctgttgga tgccctatga    5160
catgccctgg gggatgcagc tgttgccccg gccccgcact ttcgggtgac cgcgaggctg    5220
ctgattggct ggttgccacg ggctgggcgg tccctgaagt tgttgccatc tgaactctgt    5280
cggcgctggc gtcggctgcg cccaatggga ggcgagacaa ctcagggtac tagaatcact    5340
gacagaagaa gagaatcgaa agtaggtaga cagccaattc gttgcatggc aggcaaccgc    5400
acaggagaaa aattgactac cccacaatca ggcacagtaa gtagggcaca gtacgtatgt    5460
acagacaagg cgcaagcgat actgcgcgac ccggtacctc gccggcttga cacgtgcgac    5520
aggctacttt actagtattc gcagcggcgg gtcgcgcatt attacatgta ctgtgccgcc    5580
atttgatgac tgggctgctg cagtattagt agatctgccc ggcatcgccc ttccatgggc    5640
gcgacccggg actggaccct ctgactctac ctacatgtac ctaggccggg ccgggcttgg    5700
tgacttttgt ccgatcaggt cgttcgcctg gctacctatt atttctcttt cttcttctcc    5760
atcctgcttc tggccttgca attcttcttc gccactcctc cctcttcccc ccgcgatacc    5820
cttgaattcg tcagagagga aaagacgaga aaaaaaaggg cagcagagac gtcggtctgg    5880
ctcacgtgct gcatctctgc gcactctcat tttttttatt gtccgacccc tccctcaacc    5940
ttctccttcg ttgacaggct aagccttgct tcgacgctct ctctttgaat ttttctactt    6000
ctaccttctt ttcttgcgtg ttacccacca tagctcgatt cacgatgctc cgaagtcgcc    6060
aagtcacagc cagggccgtc cgggctctgg gccaggcgcg cgcctttacc tcgacgacca    6120
```

```
agcctgtcat gatccagagc agccagagga aacaggccaa cgccagcgct gctccgtaag      6180
tcgcccattg ccattgcatc ttctgtttga tatatacttc ctgctgcttg cgtggcgtcg      6240
tctctcggtt atgcgtgtca aggaccaggt gtgttcgcat cgtggttttc cagcgccgat      6300
taccggggga cgaattttg gctgctcaac tcgcgcgcgc gcattctgat tcttcgtttt       6360
caatcttgag cgacaactgg ctaacataat ggccattggc aattgcttca cacagacaag      6420
tccgccctgt accgagccct gctttcaacg ctgaagacaa agaccgcagc catgtgcagc      6480
ctctggtcaa cccgtcgaag cccgacatgg atgaatcgta tgtccacgtc ccctcgtccc      6540
gccctacaaa atgaacacga ttacaccaga atttttgcaa caatcgacac ttctataaca      6600
gaccaattga gctttgttct gaccaatcat gttgctctag attcattggc aaaaccggag      6660
gcgaaatctt ccacgagatg atgctgcgac agggtgtcaa gcacatttgt aggttccgat      6720
gccggccgcc cacacgggct ccatccttgc tccatctctc cagctaggca aatctcgcta      6780
accttgagtc accatccagt cggataccct ggcggcgcta tcctgcccgt cttcgacgcc      6840
atctacaact caaaacactt cgacttcatc ctgccccgtc atgagcaggg agctggccat      6900
atggccgagg gctatgcccg tgcctcgggc aaacccggtg tcgtcctggt gacttccggc      6960
cccggtgcta ccaatgtcat cacgcccatg caggatgccc tgtcggacgg aacgcccttg      7020
gtcgtcttct gcggccaggt ccccaccacg gccatcggca gcgatgactt ccaagaggcc      7080
gacgtcgtgg gcatctcgcg ggcctgcacc aagtggaacg tcatggtcaa gagcgttgct      7140
gagctgccgc ggagaatcaa cgaggccttt gagattgcca ccagcggccg ccctggcccc      7200
gtcctcgtcg acctgcccaa ggatgtcacg gctggtatcc tgaggagagc catccctacg      7260
gagactgctc tgccgtctct gcccagtgcc gcctcccgcg ccgccatgga gctgagctcc      7320
aagcagctca acgcctccat caagcgtgcc gccgacctca tcaacatcgc caagaagccc      7380
gtcatctacg ccgtcagggg tgtcatccag tccgagggcg gcgttgagct cctgaagcag      7440
ctggcggaca aggcctccat ccccgtcacc accaccctcc atggcctggg tgcctttgat      7500
gagctggacg agaagtcgct gcacatgctg ggcatgcacg gctcggcgta tgccaacatg      7560
gccatgcagc aggccgacct catcatcgcc ctcggcagcc gattcgacga ccgtgttact      7620
ctgaatgtct ccaaatttgc gcctgcagcc aggcaagctg ctgccgaggg ccgcggcggc      7680
atcattcact ttgagatcat gcccaagaac atcaacaagg tcatccaggc gaccgaggcc      7740
gtcgagggcg acgtcgccac caacctgaag cacctcattc cccagattgc cgaaaagtcc      7800
atggcggacc gaggagagtg gttcggcctc atcaatgagt ggaagaagaa gtggcccctg      7860
tcaaactacc agcgcgcgga gcgggctggc ctcatcaagc cgcagacggt catggaggag      7920
attagcaacc tgacgccaa ccgaaggac aagacgtaca ttgccacggg tgtcggccag        7980
caccagatgt gggttgccca gcacttccgc tggaggcacc ctcgatccat gattacctct      8040
ggtggtctgg gcaccatggg ctacggtctc cccgcggcca ttggcgccaa ggtggcccag      8100
cccgacgctc tcgtaattga cgttgatggc gatgcctcgt ttaacatgac gctgacggag      8160
ctgtcgactc tgcacagtt caacattggc gtcaaggtgg ttgtgctcaa caacgaggag       8220
cagggcatgg tgacgcagtg gcagaacctc ttttacgagg accgatatgc ccacacgcac      8280
cagaagaacc ccgacttcat gaagctggcc gacgccatgg gcgttcagca ccagcgcgtg      8340
acggagccgg agaagctggt cgatgccctg acgtggctga tcaacaccga tggccgggcc      8400
ctgttggagg ttgtcacgga caagaaggtg cctgtcctgc ccatggtgcc cgccggatcg      8460
gccctgcacg agttcctcgt ctttgaacct ggtgagtcta cttcagacat attgcttgcg      8520
```

```
cattgcagat actaacactc tcacagaaaa ggataagcag cgccgtgagc tgatgaagga    8580
gagaacaaag ggtgtgcact cctaaagcga tgatgtctgc gaggggttct tcgttgaacc    8640
ctagttcagg caccatctta ccctcttatt ttttcccgtg ggctttcatt ttgtgtcatc    8700
cgagcatgac gttgtagggt tggagtttct tccttttat cttgtcattt actggtaccc    8760
ataggcgcga gactaggctt ccatgttttg ttttgcgact ttcaaaaagt acttttagtg    8820
gtttggggca cgacgagggg gggcaacctc ttctgtcgaa aaaggtggct ggatggatga    8880
gatgagatga gatgagggtg aagatagata cctgcagtgt ttttgacgcg acgggatggc    8940
gatcgctcag ggttgcgttt ccagtctaga cacgtataac ggcacaagtg tctctcacca    9000
aatgggttat atctcaaatg tgatctaagg atggaaagcc cagaatatcg atcgcgcgca    9060
gatccatata tagggcccgg gttataatta cctcaggtcg acgtcccatg gccattcgaa    9120
ttcgtaatca tggtcatagc tgtttcctgt gtgaaattgt tatccgctca caattccaca    9180
caacatacga gccggaagca taaagtgtaa agcctgggt gcctaatgag tgagctaact    9240
cacattaatt gcgttgcgct cactgcccgc tttccagtcg gaaacctgt cgtgccagct    9300 gcattaatga atcggccaac gcgcggggag aggcggtttg cgtattgggc gctcttccgc    9360
ttcctcgctc actgactcgc tgcgctcggt cgttcggctg cggcgagcgg tatcagctca    9420
ctcaaaggcg gtaatacggt tatccacaga atcaggggat aacgcaggaa agaacatgtg    9480
agcaaaaggc cagcaaaagg ccaggaaccg taaaaaggcc gcgttgctgg cgttttttcca    9540 taggctccgc cccctgacg agcatcacaa aaatcgacgc tcaagtcaga ggtggcgaaa    9600
cccgacagga ctataaagat accaggcgtt tcccctgga agctccctcg tgcgctctcc    9660
tgttccgacc ctgccgctta ccggatacct gtccgccttt ctcccttcgg gaagcgtggc    9720
gctttctcat agctcacgct gtaggtatct cagttcggtg taggtcgttc gctccaagct    9780
gggctgtgtg cacgaacccc ccgttcagcc cgaccgctgc gccttatccg gtaactatcg    9840
tcttgagtcc aacccggtaa gacacgactt atcgccactg gcagcagcca ctggtaacag    9900
gattagcaga gcgaggtatg taggcggtgc tacagagttc ttgaagtggt ggcctaacta    9960
cggctacact agaagaacag tatttggtat ctgcgctctg ctgaagccag ttaccttcgg    10020
aaaaagagtt ggtagctctt gatccggcaa acaaaccacc gctggtagcg gtggtttttt    10080
tgtttgcaag cagcagatta cgcgcagaaa aaaaggatct caagaagatc ctttgatctt    10140
ttctacgggg tctgacgctc agtggaacga aaactcacgt taagggattt tggtcatgag    10200
attatcaaaa aggatcttca cctagatcct tttaaattaa aaatgaagtt ttaaatcaat    10260
ctaaagtata tatgagtaaa cttggtctga cagttaccaa tgcttaatca gtgaggcacc    10320
tatctcagcg atctgtctat ttcgttcatc catagttgcc tgactccccg tcgtgtagat    10380
aactacgata cgggagggct taccatctgg ccccagtgct gcaatgatac cgcgagaccc    10440
acgctcaccg gctccagatt tatcagcaat aaaccagcca gccggaaggg ccgagcgcag    10500
aagtggtcct gcaactttat ccgcctccat ccagtctatt aattgttgcc gggaagctag    10560
agtaagtagt tcgccagtta atagtttgcg caacgttgtt gccattgcta caggcatcgt    10620
ggtgtcacgc tcgtcgtttg gtatggcttc attcagctcc ggttcccaac gatcaaggcg    10680
agttacatga tcccccatgt tgtgcaaaaa agcggttagc tccttcggtc ctccgatcgt    10740
tgtcagaagt aagttggccg cagtgttatc actcatggtt atggcagcac tgcataattc    10800
tcttactgtc atgccatccg taagatgctt ttctgtgact ggtgagtact caaccaagtc    10860
attctgagaa tagtgtatgc ggcgaccgag ttgctcttgc ccggcgtcaa tacgggataa    10920
```

| | |
|---|---|
| taccgcgcca catagcagaa ctttaaaagt gctcatcatt ggaaaacgtt cttcggggcg | 10980 |
| aaaactctca aggatcttac cgctgttgag atccagttcg atgtaaccca ctcgtgcacc | 11040 |
| caactgatct tcagcatctt ttactttcac cagcgtttct gggtgagcaa aaacaggaag | 11100 |
| gcaaaatgcc gcaaaaaagg gaataagggc gacacggaaa tgttgaatac tcatactctt | 11160 |
| ccttttcaa tattattgaa gcatttatca gggttattgt ctcatgagcg gatacatatt | 11220 |
| tgaatgtatt tagaaaaata acaaataggg gttccgcgc acatttcccc gaaaagtgcc | 11280 |
| acctgacgtc taagaaacca ttattatcat gacattaacc tataaaaata ggcgtatcac | 11340 |
| gaggcccttt cgtctcgcgc gtttcggtga tgacggtgaa aacctctgac acatgcagct | 11400 |
| cccggagacg gtcacagctt gtctgtaagc ggatgccggg agcagacaag cccgtcaggg | 11460 |
| cgcgtcagcg ggtgttggcg ggtgtcgggg ctggcttaac tatgcggcat cagagcagat | 11520 |
| tgtactgaga gtgcaccata aaattgtaaa cgttaatatt ttgttaaaat tcgcgttaaa | 11580 |
| tttttgttaa atcagctcat tttttaacca ataggccgaa atcggcaaaa tcccttataa | 11640 |
| atcaaaagaa tagcccgaga tagggttgag tgttgttcca gtttggaaca agagtccact | 11700 |
| attaaagaac gtggactcca acgtcaaagg gcgaaaaacc gtctatcagg gcgatggccc | 11760 |
| actacgtgaa ccatcaccca aatcaagttt tttggggtcg aggtgccgta aagcactaaa | 11820 |
| tcggaaccct aaagggagcc cccgatttag agcttgacgg ggaaagccgg cgaacgtggc | 11880 |
| gagaaaggaa gggaagaaag cgaaaggagc gggcgctagg gcgctggcaa gtgtagcggt | 11940 |
| cacgctgcgc gtaaccacca cacccgccgc gcttaatgcg ccgctacagg gcgcgtacta | 12000 |
| tggttgcttt gacgtatgcg gtgtgaaata ccgcacagat gcgtaaggag aaaataccgc | 12060 |
| atcaggcgcc attcgccatt caggctgcgc aactgttggg aagggcgatc ggtgcgggcc | 12120 |
| tcttcgctat tacgccagct ggcgaaaggg ggatgtgctg caaggcgatt aagttgggta | 12180 |
| acgccagggt tttcccagtc acgacgttgt aaaacgacgg ccagtgccc | 12229 |

<210> SEQ ID NO 10
<211> LENGTH: 7531
<212> TYPE: DNA
<213> ORGANISM: Artificial Sequence
<220> FEATURE:
<223> OTHER INFORMATION: Synthetic construct

<400> SEQUENCE: 10

| | |
|---|---|
| cattacgcct cccccataga taggtctagg ctggcgggtt ggtgcttttg ccctttgtct | 60 |
| gccgcgacct cttggtgacg ctgcatcgtg ttggctgtag ctgcacgccc ggcctctttt | 120 |
| ctggcatctc gcacagactg tacgcagaac atgtgtaagt gactttctat tgtaggactt | 180 |
| ggatggatgg gagatggcta tagacaacaa gagcgacaac aaggattata gacagttcca | 240 |
| ttacctgggc gaccaccatc gcacttcacc ttgctcgccc ggcaggactg gcaggcgttg | 300 |
| gcaatcttga gtcgctccct gtacagcgac aaggggcgcct gagcctgcac ctgagcctgg | 360 |
| gcctgagtct gagcctgaag ccgttgatcc tcgtcttgac gggcggacat gacgctttac | 420 |
| gtgagctgag tccagggctg tcgtcggcaa gtgattcggc agccggcagg cacagacgaa | 480 |
| agataagaag cggctcgttc accagatccg aaggcggaat gcaagaatgt ccgatgatgt | 540 |
| cggggaagag aaggcgatgc ctcgtctatc tgggaggcga gggaagaagg gaaagcaact | 600 |
| cccgcctcgg cacagctact cattggtcag agcggacttc ggagtataac cacacggctg | 660 |
| acaaacctgc atcgacgtg atggcgttct tttggtccaa tcatggctga atgcgacgtt | 720 |
| ggttgtgtcg gcccctgcag ccaatgagaa gctggtccga tcctggggac gagggagagg | 780 |

```
caagcatatc gtataagtcc aagctcaagc ttggcggcag gtaccggttg atgtggtcgc    840
tgtatataag taaaagaact cgattccgct tcggagtttt ctctgtcacc cttcacaagt    900
ttgtacaaaa aagcaggcta tgcacgtcct gtcgactgcg gtgctgctcg gctccgttgc    960
cgttcaaaag gtcctgggaa gaccaggatc aagcggtctg tccgacgtca ccaagaggtc   1020
tgttgacgac ttcatcagca ccgagacgcc tattgcactg aacaatcttc tttgcaatgt   1080
tggtcctgat ggatgccgtg cattcggcac atcagctggt gcggtgattg catctcccag   1140
cacaattgac ccggactgta agttggcctt gatgaaccat atcatatatc gccgagaagt   1200
ggaccgcgtg ctgagactga gacagactat tacatgtgga cgcgagatag cgctcttgtc   1260
ttcaagaacc tcatcgaccg cttcaccgaa acgtacgatg cgggcctgca gcgccgcatc   1320
gagcagtaca ttactgccca ggtcactctc cagggcctct ctaaccccgc gggctccctc   1380
gcggacggct ctggtctcgg cgagcccaag tttgagttga ccctgaagcc tttcaccggc   1440
aactggggtc gaccgcagcg ggatggccca gctctgcgag ccattgcctt gattggatac   1500
tcaaagtggc tcatcaacaa caactatcag tcgactgtgt ccaacgtcat ctggcctatt   1560
gtgcgcaacg acctcaacta tgttgccag tactggtcag tgcttgcttg ctcttgaatt    1620
acgtctttgc ttgtgtgtct aatgcctcca ccacaggaac caaaccggct ttgacctctg   1680
ggaagaagtc aatgggagct cattctttac tgttgccaac cagcaccgag gtatgaagca   1740
aatcctcgac attcgctgct actgcacatg agcattgtta ctgaccagct ctacagcact   1800
tgtcgagggc gccactcttg ctgccactct tggccagtcg ggaagcgctt attcatctgt   1860
tgctccccag gttttgtgct ttctccaacg attctgggtg tcgtctggtg gatacgtcga   1920
ctccaacagt atgtcttttc actgtttata tgagattggc caatactgat agctcgcctc   1980
tagtcaacac caacgagggc aggactggca aggatgtcaa ctccgtcctg acttccatcc   2040
acaccttcga tcccaacctt ggctgtgacg caggcacctt ccagccatgc agtgacaaag   2100
cgctctccaa cctcaaggtt gttgtcgact ccttccgctc catctacggc gtgaacaagg   2160
gcattcctgc cggtgctgcc gtcgccattg ccggtatgc agaggatgtg tactacaacg    2220
gcaacccttg gtatcttgct acatttgctg ctgccgagca gctgtacgat gccatctacg   2280
tctggaagaa gacgggctcc atcacggtga ccgccacctc cctggccttc ttccaggagc   2340
ttgttcctgg cgtgacggcc gggacctact ccagcagctc ttcgaccttt accaacatca   2400
tcaacgccgt ctcgacatac gccgatggct cctcagcga ggctgccaag tacgtccccg    2460
ccgacggttc gctggccgag cagtttgacc gcaacagcgg cactccgctg tctgcgcttc   2520
acctgacgtg gtcgtacgcc tcgttcttga cagccacggc ccgtcgggct ggcatcgtgc   2580 cccccctcgtg ggccaacagc agcgctagca cgatcccctc gacgtgctcc ggcgcgtccg   2640
tggtcggatc ctactcgcgt cccaccgcca cgtcattccc tccgtcgcag acgcccaagc   2700
ctggcgtgcc ttccggtact ccctacacgc ccctgccctg cgcgaccca acctccgtgg    2760 ccgtcacctt ccacgagctc gtgtcgacac agtttggcca gacggtcaag gtggcgggca   2820
acgccgcggc cctgggcaac tggagcacga gcgccgccgt ggctctggac gccgtcaact   2880
atgccgataa ccaccccctg tggattggga cggtcaacct cgaggctgga gacgtcgtgg   2940
agtacaagta catcaatgtg ggccaagatg gctccgtgac ctgggagagt gatcccaacc   3000
acacttacac ggttcctgcg gtggcttgtg tgacgcaggt tgtcaaggag gacacctggc   3060
agtcgtaaac ccagctttct tgtacaaagt ggtgatcgcg ccagctccgt gcgaaagcct   3120
gacgcaccgg tagattcttg gtgagcccgt atcatgacgg cggcgggagc tacatggccc   3180
```

```
cgggtgattt attttttttg tatctacttc tgaccctttt caaatatacg gtcaactcat    3240 cttteactgg agatgcggcc tgcttggtat tgcgatgttg tcagcttggc aaattgtggc    3300
tttcgaaaac acaaaacgat tccttagtag ccatgcattt taagataacg gaatagaaga    3360
aagaggaaat taaaaaaaaa aaaaaaacaa acatcccgtt cataacccgt agaatcgccg    3420
ctggcgcgcc tgagacaatg gccggcaatg gtaaaaagga ccaagatgta ctaggtagtt    3480
gcaatgtggc ttattaccta cctactacct ggtaggcacc tactaggtac ttgggtagac    3540
ggacaatgaa atttgaagtc ggggttgcag gaaagcaggg cgctggacac attgtgcttc    3600
aggcggtacc cgtcgtcatc gtcagccaat gtcgaggccc ggcagccgga ggagcgagac    3660
aaccttggcc ggaggagccc gcaggtacct gccaaagcgc ggctggtacc tctcaaccct    3720
ctcaggcctg ttggatgccc tatgacatgc cctgggggat gcagctgttg ccccggcccc    3780
gcactttcgg gtgaccgcga ggctgctgat tggctggttg ccacgggctg ggcggtccct    3840
gaagttgttg ccatctgaac tctgtcggcg ctggcgtcgg ctgcgcccaa tgggaggcga    3900
gacaactcag ggtactagaa tcactgacag aagaagagaa tcgaaagtag gtagacagcc    3960
aattcgttgc atggcaggca accgcacagg agaaaaattg actacccac  aatcaggcac    4020 agtaagtagg gcacagtacg tatgtacaga caaggcgcaa gcgatactgc gcgacccggt    4080
acctcgccgg cttgacacgt gcgacaggct actttactag tattcgcagc ggcgggtcgc    4140
gcattattac atgtactgtg ccgccatttg atgactgggc tgctgcagta ttagtagatc    4200
tgcccggcat cgcccttcca tgggcgcgac ccgggactgg accctctgac tctacctaca    4260
tgtacctagg ccgggccggg cttggtgact tttgtccgat caggtcgttc gcctggctac    4320
ctattatttc tctttcttct tctccatcct gcttctggcc ttgcaattct tcttcgccac    4380
tcctccctct tcccccgcg  atacccttga attcgtcaga gaggaaaaga cgagaaaaaa    4440
aagggcagca gagacgtcgg tctggctcac gtgctgcatc tctgcgcact ctcattttt     4500 ttattgtccg accoctccct caaccttctc cttcgttgac aggctaagcc ttgcttcgac    4560
gctctctctt tgaattttc  tacttctacc ttcttttctt gcgtgttacc caccatagct    4620
cgattcacga tgctccgaag tcgccaagtc acagccaggg ccgtccgggc tctgggccag    4680
gcgcgcgcct ttacctcgac gaccaagcct gtcatgatcc agagcagcca gaggaaacag    4740
gccaacgcca gcgctgctcc gtaagtcgcc cattgccatt gcatcttctg tttgatatat    4800
acttcctgct gcttgcgtgg cgtcgtctct cggttatgcg tgtcaaggac caggtgtgtt    4860
cgcatcgtgt ttttccagcg ccgattaccg ggggacgaat ttttggctgc tcaactcgcg    4920
cgcgcgcatt ctgattcttc gttttcaatc ttgagcgaca actggctaac ataatggcca    4980
ttggcaattg cttcacacag acaagtccgc cctgtaccga gccctgcttt caacgctgaa    5040
gacaaagacc gcagccatgt gcagcctctg gtcaacccgt cgaagcccga catggatgaa    5100
tcgtatgtcc acgtccctc  gtcccgccct acaaaatgaa cacgattaca ccagaatttt    5160
tgcaacaatc gacacttcta taacagacca attgagcttt gttctgacca atcatgttgc    5220
tctagattca ttggcaaaac cggaggcgaa atcttccacg agatgatgct gcgacagggt    5280
gtcaagcaca tttgtaggtt ccgatgccgg ccgcccacac gggctccatc cttgctccat    5340
ctctccagct aggcaaatct cgctaacctt gagtcaccat ccagtcggat accctggcgg    5400
cgctatcctg cccgtcttcg acgccatcta caactcaaaa cacttcgact tcatcctgcc    5460
ccgtcatgag cagggagctg gccatatggc cgagggctat gcccgtgcct cgggcaaacc    5520
cggtgtcgtc ctggtgactt ccggcccggg tgctaccaat gtcatcacgc ccatgcagga    5580
```

```
tgccctgtcg gacggaacgc ccttggtcgt cttctgcggc caggtcccca ccacggccat    5640
cggcagcgat gacttccaag aggccgacgt cgtgggcatc tcgcgggcct gcaccaagtg    5700
gaacgtcatg gtcaagagcg ttgctgagct gccgcggaga atcaacgagg cctttgagat    5760
tgccaccagc ggccgccctg gccccgtcct cgtcgacctg cccaaggatg tcacggctgg    5820
tatcctgagg agagccatcc ctacggagac tgctctgccg tctctgccca gtgccgcctc    5880
ccgcgccgcc atggagctga gctccaagca gctcaacgcc tccatcaagc gtgccgccga    5940
cctcatcaac atcgccaaga agcccgtcat ctacgccggt cagggtgtca tccagtccga    6000
gggcggcgtt gagctcctga agcagctggc ggacaaggcc tccatccccg tcaccaccac    6060
cctccatggc ctgggtgcct ttgatgagct ggacgagaag tcgctgcaca tgctgggcat    6120
gcacggctcg gcgtatgcca acatggccat gcagcaggcc gacctcatca tcgccctcgg    6180
cagccgattc gacgaccgtg ttactctgaa tgtctccaaa tttgcgcctg cagccaggca    6240
agctgctgcc gagggccgcg gcggcatcat tcactttgag atcatgccca agaacatcaa    6300
caaggtcatc caggcgaccg aggccgtcga gggcgacgtc gccaccaacc tgaagcacct    6360
cattccccag attgccgaaa agtccatggc ggaccgagga gagtggttcg gcctcatcaa    6420
tgagtggaag aagaagtggc ccctgtcaaa ctaccagcgc gcggagcggg ctggcctcat    6480
caagccgcag acggtcatgg aggagattag caacctgacg gccaaccgaa aggacaagac    6540
gtacattgcc acgggtgtcg gccagcacca gatgtgggtt gcccagcact ccgctggag    6600 gcaccctcga tccatgatta cctctggtgg tctgggcacc atgggctacg gtctccccgc    6660
ggccattggc gccaaggtgg cccagcccga cgctctcgta attgacgttg atggcgatgc    6720
ctcgtttaac atgacgctga cggagctgtc gactgctgca cagttcaaca ttggcgtcaa    6780
ggtggttgtg ctcaacaacg aggagcaggg catggtgacg cagtggcaga acctcttta    6840 cgaggaccga tatgcccaca cgcaccagaa gaaccccgac ttcatgaagc tggccgacgc    6900
catgggcgtt cagcaccagc gcgtgacgga gccgagaag ctggtcgatg ccctgacgtg    6960
gctgatcaac accgatggcc cggccctgtt ggaggttgtc acggacaaga aggtgcctgt    7020
cctgcccatg gtgcccgccg gatcggccct gcacgagttc ctcgtctttg aacctggtga    7080
gtctacttca gacatattgc ttgcgcattg cagatactaa cactctcaca gaaaaggata    7140
agcagcgccg tgagctgatg aaggagagaa caaagggtgt gcactcctaa agcgatgatg    7200
tctgcgaggg gttcttcgtt gaaccctagt tcaggcacca tcttaccctc ttattttttc    7260
ccgtgggctt tcattttgtg tcatccgagc atgacgttgt aggggttggag tttcttcctt    7320 tttatcttgt catttactgg tacccatagg cgcgagacta ggcttccatg ttttgttttg    7380
cgactttcaa aaagtacttt tagtggtttg ggcacgacg agggggggca acctcttctg    7440
tcgaaaaagg tggctggatg gatgagatga gatgagatga gggtgaagat agatacctgc    7500 agtgttttg acgcgacggg atggcgatcg                                     7531
```